United States Patent
Collins et al.

(10) Patent No.: US 7,290,882 B2
(45) Date of Patent: Nov. 6, 2007

(54) HAND HELD DEVICE AND METHODS FOR EXAMINING A PATIENT'S RETINA

(75) Inventors: William J. Collins, Arvada, CO (US); Robert E. Levine, Los Angeles, CA (US)

(73) Assignee: Ocutronics, LLC, Denver, CO (US)

( * ) Notice: Subject to any disclaimer, the term of this patent is extended or adjusted under 35 U.S.C. 154(b) by 303 days.

(21) Appl. No.: 11/053,491

(22) Filed: Feb. 7, 2005

(65) Prior Publication Data
US 2006/0146284 A1    Jul. 6, 2006

(51) Int. Cl.
*A61B 3/10*    (2006.01)
(52) U.S. Cl. ............................... 351/218; 351/215
(58) Field of Classification Search ............. 351/215, 351/218
See application file for complete search history.

(56) References Cited

U.S. PATENT DOCUMENTS

| | | | | |
|---|---|---|---|---|
| 4,208,107 A | * | 6/1980 | Oharek | 351/206 |
| 4,265,518 A | * | 5/1981 | Matsumura | 351/206 |
| 4,938,584 A | * | 7/1990 | Suematsu et al. | 351/211 |
| 6,112,114 A | * | 8/2000 | Dreher | 600/476 |
| 2003/0156259 A1 | * | 8/2003 | Shibutani et al. | 351/211 |

* cited by examiner

*Primary Examiner*—Jordan Schwartz
*Assistant Examiner*—James C. Jones
(74) *Attorney, Agent, or Firm*—Greenberg Traurig, LLP

(57) ABSTRACT

A hand held device for examining a patient's retina. In one example, the device generates visible or non-visible illuminating beams having desired spectral content. The illuminating beams are then polarized to generate polarized light beam(s) that are directed towards the patient's retina. At the patient's eye, a portion of the polarized beam is partially reflected by the cornea and travels back to the device, and another portion of the polarized beam enters the eye through the undilated pupil, illuminates the patient's retina, and generates a reflected retinal image (generally de-polarized) which also travels back to the device. The device receives the retinal image and transmits certain portions of the retinal image on through to an image detector (i.e., CCD or CMOS); and the device deflects the received polarized corneal reflections away from the image capture device. Hence, the image capture device receives retinal images but does not receive the polarized corneal reflected light.

17 Claims, 34 Drawing Sheets

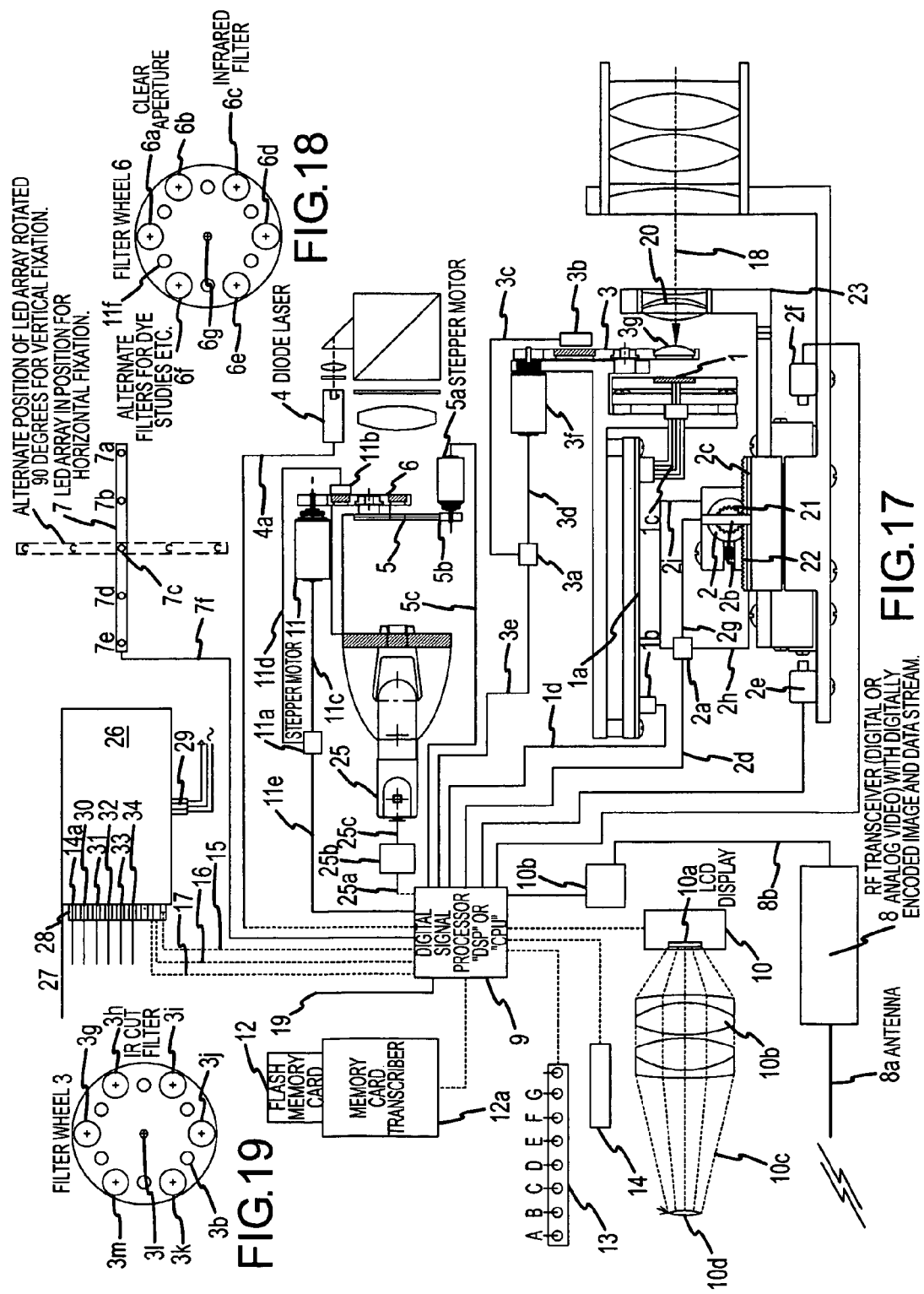

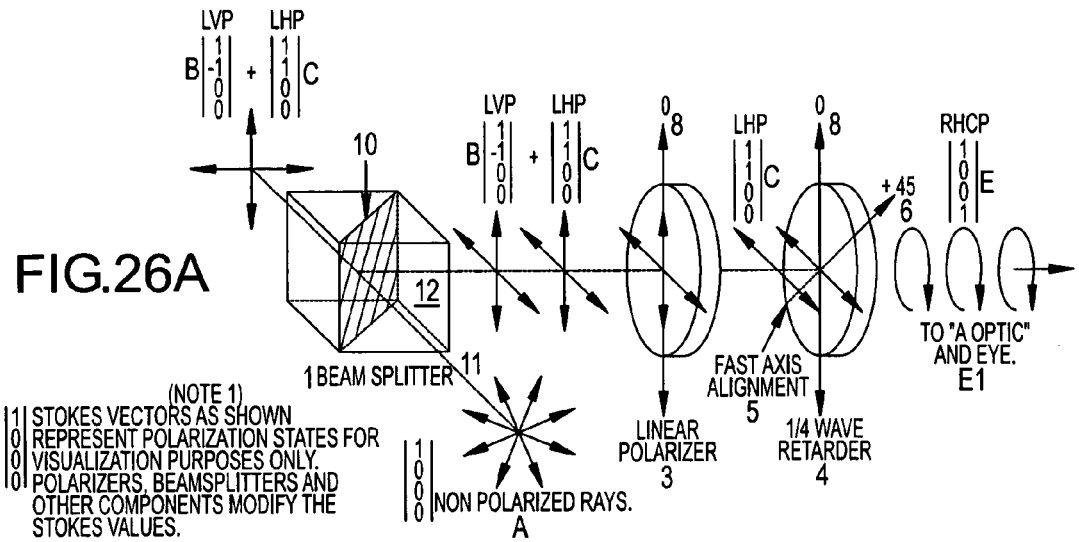

FIG.26A (NOTE 1) Stokes vectors as shown represent polarization states for visualization purposes only. Polarizers, beamsplitters and other components modify the Stokes values.

(NOTE 2) In theory, the unpolarized rays from the halogen lamp are a mixed distribution of all possible states of polarization, linear, elliptical etc. The linear P magnetic waves and linear S electric waves are specifically represented for understanding of the working states of polarization that are of functional interest.

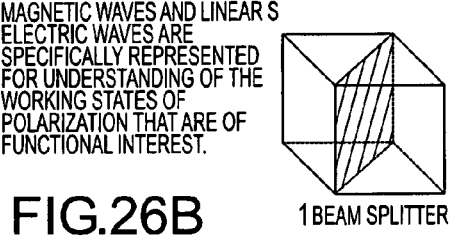

FIG.26B

ACRONYM DEFINITIONS:
(B) LVP-LINEAR VERTICAL POLARIZATION (S PLANE)
(C) LHP-LINEAR HORIZONTAL POLARIZATION (P PLANE)
(D) LHCP-LEFT HAND CIRCULAR POLARIZATION
(E) RHCP-RIGHT HAND CIRCULAR POLARIZATION

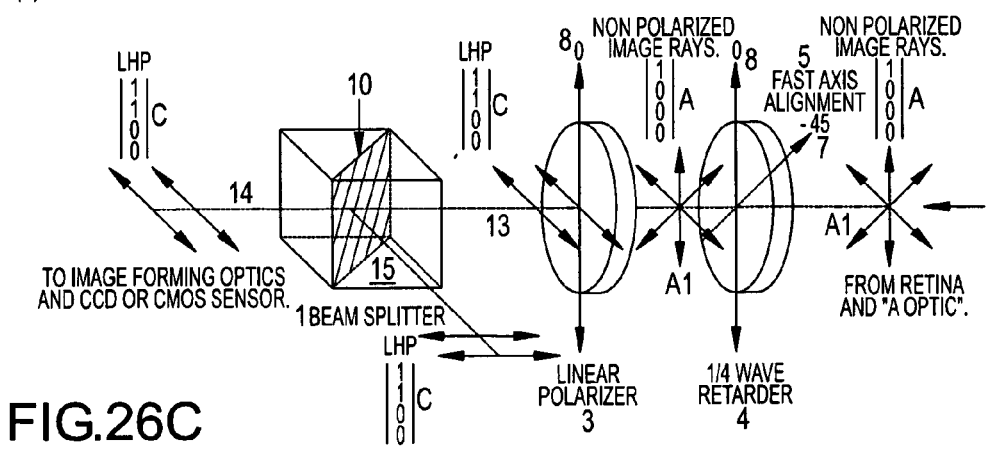

FIG.26C

HAND HELD DEVICE AND METHODS FOR
EXAMINING A PATIENT'S RETINA

FIELD OF THE INVENTION

This invention relates, in general, to methods and devices for performing an examination of the eye, and more particularly, for performing an examination of the retina of a patient's eye.

BACKGROUND OF THE INVENTION

Many conventional retinal eye examinations involve the use of eye drops which are given to a patient to force the patient's iris open (dilates the pupils). These drops are known as mydriatic eye drops. After the patient's pupils are dilated, the eye doctor then examines the patient's retina, also known as the "fundus," with a conventional ophthalmoscope, which typically uses white light. Once a conventional eye exam is completed, the patient's pupils remain dilated for possibly hours, which may be very inconvenient for the patient and may prevent the patient from being able to drive, work, etc.

Viewing the retina and optic nerve is a basic part of both general medical exams (as performed by family practitioners, pediatricians, internists and other medical professionals) and eye exams (as performed by ophthalmologists and optometrists). As part of a general exam, the retina is the only place in the body where the practitioner can view blood vessels directly. Diseases that affect blood vessels, such as diabetes mellitus and hypertension, among others, can be diagnosed on the basis of changes in retinal blood vessels. Studies have shown that the blood vessel changes in the eye in these diseases correlate well with similar changes in other parts of the body, such as the kidney. Therefore the amount to which the vascular changes associated with these diseases has progressed can also be ascertained.

The optic nerve, which is actually a part of the brain, can also be visualized. Increased intracranial pressure (e.g., as caused by brain tumors) can often be diagnosed by seeing the resultant swelling of the optic nerve.

From the standpoint of the eye professional, specific important potentially blinding diseases, such diabetic retinopathy, glaucoma, and macular degeneration, among others, can both be diagnosed and followed by viewing the retina and optic nerve.

An instrument used to view the retina and optic nerve is called an ophthalmoscope. It may be either battery operated or powered from a transformer. In either case, only visible light is available for viewing the patient. Even with the use of filters, the light is uncomfortable to the patient, sometimes to the point of making the examination difficult or impossible. Opacities to visible light located in the lens of the eye (e.g., cataract) or in the vitreous (e.g., blood) also limit the ability to see the retina and optic nerve, sometimes totally precluding such examination.

In order to better study, document, share and record the changes seen in the retina and optic nerve, photographs of the back of the eye (called fundus photos) are frequently taken. The standard camera for doing this is a large table mounted instrument which generally uses photographic film (although digital variants have recently become available) and flash photography. Some smaller variants have been developed, but still require cables hooked to large power supplies, resulting in cumbersome units.

The large camera units generally may require the services of a professional photographer to operate, and the units may be priced in the range from $35,000 to $100,000, both of which factors limit their availability. The table mountings can make them inaccessible to wheel-chair patients, unless special table extensions are available. The cameras are rarely available for bed patients, in some instances. Also, such cameras are difficult to move from office to office, except by van.

As recognized by the present inventors, what is needed is a hand held device and method for examining a patient's retina without the need for mydriatic eye drops, so that retinal examinations can be performed quickly, accurately, and comfortably without dilation of the patient's pupils.

It is against this background that various embodiments of the present invention were developed.

SUMMARY OF THE INVENTION

In light of the above and according to one broad aspect of one embodiment of the invention, disclosed herein is a hand held device for examining a patient's retina. In one example, the device generates visible or non-visible light beams or light rays having desired spectral content that can be used, after polarization, for illuminating the patient's retina during the examination. The illuminating beams may include infrared (IR) or visible light. IR light can be used to perform the examination through the patient's undilated pupil, without the need for mydriatic drops, and the images received and processed by the hand held device can be real-time, dynamic video images of the retina. Visible light can be used for short time periods (i.e., approximately 0.1 to 0.008 seconds or other time periods) to image the retina for static or still images. Further, the hand held device may generate light selectively having two or more spectral ranges, and alternatively couple light of different spectral ranges into the optical path of the device. For instance, the illuminating beam section can provide IR light to view the retina in real-time (i.e., dynamic real time video images), then be controllably switched to provide a pulse of visible light to take a still image (i.e., a high resolution static image), then be controllably switched to again provide IR light. Hence, a hand held device according to an embodiment of the present invention can provide both video and high quality still photographic capabilities. Furthermore, in another example, the illuminating beam section can provide IR light to view the retina in real-time (i.e., dynamic real time video images), then be controllably switched to provide light with an appropriate exitation wavelength to excite fluorescein dye or other conventional dyes to perform dye studies of the retina.

In one embodiment, the illuminating beams generated by the device are polarized to generate polarized light beam(s) that are used to illuminate the patient's retina. A specific polarization state is imparted on the light directed towards the patient's eye. In one example, the polarized light beam travels towards the patient's retina along an optical path that is disposed at an angle (such as 90 degrees) relative to the generated illuminated light beam.

At the patient's eye, a portion of the polarized beam is then partially reflected by the patient's cornea. This corneal reflection (which is polarized) travels back in the direction of the device. Another portion of the polarized beam enters the eye through the pupil, illuminates the patient's retina, and this generates a reflected retinal image (generally depolarized) which travels back in the direction of the device.

In one example, the device receives the retinal image as well as the polarized corneal reflections. The device transmits (i.e., does not reflect or block) certain portions of the retinal image, defined by their polarization states, on through to an image capture detector (such as a CCD or CMOS detector or capture device, or other digital or non-digital image capture device). The image capture portion of the device may include optics to process the retinal image.

As to the polarized corneal reflections, in one example, the device receives the polarized corneal reflections and does not materially transmit these polarized corneal reflections to the image detector (i.e., the corneal reflections are diverted, reflected, or otherwise extinguished). Hence, the image detector receives retinal images having certain states of depolarized light but does not materially receive the polarized corneal reflected light.

According to another broad aspect of one embodiment of the present invention, disclosed herein is a hand held device for examining a retina through a pupil. In one example, the hand held device may include a light source generating light (visible or non-visible); a first lens refracting the light to form a refracted beam; a first polarizer receiving the refracted beam and forming a linear polarized beam; a second polarizer for reflecting linearly polarized light, the second polarizer receiving the linear polarized beam and reflecting the linear polarized beam; and a second lens refracting the linear polarized beam from the second polarizer, the second lens converging the linear polarized beam for passage through the pupil to illuminate the retina. This illumination of the retina can produce a retinal image that is received and processed by the hand held device. Further, the device can be used to examine the patient's retina through an undilated pupil, without the need for mydriatic drops.

In one example, the light generated by the light source includes infrared (IR) light, and the light source may include a first lamp in series with an infrared (IR) filter to generate the IR light. In another example, the light generated by the light source includes visible light.

The light source may include two or more discrete light sources providing different spectral ranges of illumination, for example, a first lamp in series with an infrared (IR) bandpass filter to generate IR light, a second lamp in series with an visible light bandpass filter to generate visible light, wherein when the first lamp is on, the second lamp is off. A simple electronic switch may be used to provide power to the first lamp and not the second, and then to provide power to the second lamp and not the first. In this manner, the device can switch between two different spectral ranges of illumination, without the need for moving parts.

In another example, the device may also include a reflector reflecting the light to form a reflected converging beam for coupling into the first lens. The device may also include a variable diaphragm located between the light source and the first lens for controlling the intensity of the light. The device may also include a beam splitter positioned between the first lens and the first polarizer, the beam splitter receiving the refracted beam, the beam splitter reflecting the refracted beam to the first polarizer.

In one example, the first polarizer may be a wire grid polarizer, and the second polarizer may be a wire grid polarizer, wherein the second polarizer can be substantially disposed at an angle of 45 degrees relative to linear polarized beam.

According to another broad aspect of another embodiment of the present invention, disclosed herein is a hand held device for examining a retina through a pupil. In one example, the device may include a light source generating light; a reflector reflecting the light to form a reflected converging beam; a polarizer receiving the reflected converging beam and forming a linear polarized converging beam; and a second polarizer for reflecting linearly polarized light, the second polarizer receiving the linear polarized converging beam and reflecting the linear polarized converging beam for passage through the pupil to illuminate the retina.

In another example, the device may include a lens refracting the linear polarized converging beam from the second polarizer, the lens converging the linear polarized converging beam for passage through the pupil.

According to another broad aspect of another embodiment of the present invention, disclosed herein is a hand held device for examining a retina through a pupil. In one embodiment, the device may include a light source generating light; a reflector reflecting the light to form a reflected converging beam; a polarizer receiving the reflected converging beam and forming a linear polarized converging beam; and a second polarizer for reflecting linearly polarized light, the second polarizer receiving the linear polarized converging beam and reflecting the linear polarized converging beam through the pupil to illuminate the retina and thereby creating a reflected image of the retina, a portion of said reflected image passing through the second polarizer.

In another example, the device may also include a lens refracting said portion of the reflected image of the retina to create a real image of the retina, and a detector receiving the real image of the retina. The detector may be a charged coupled device (CCD) or CMOS image detector or other image capture device.

In another embodiment, a hand held device can be integrated with an ophthalmoscope, allowing practitioners to record images contemporaneously as they see them, without making special arrangements to have photos taken. Being portable, the hand held device can be taken from office to office, and can be used for wheel-chair and bed patients. Further, images may be captured in electronic format, and can be transmitted to other locations for review (telemedicine), and could be computer processed for analysis, integrated with other images, and stored for years if desired.

Other embodiments of the invention are disclosed herein. The foregoing and other features, utilities and advantages of various embodiments of the invention will be apparent from the following more particular description of the various embodiments of the invention as illustrated in the accompanying drawings and claims.

BRIEF DESCRIPTION OF THE DRAWINGS

FIG. 17 illustrates an example of a block diagram of a hand held device having a rotatable filter wheel for examining a patient's retina, in accordance with one embodiment of the present invention.

FIG. 18 illustrates an example of a filter wheel, in accordance with one embodiment of the present invention.

FIG. 19 illustrates another example of a filter wheel, in accordance with one embodiment of the present invention.

FIGS. 26A-C illustrate examples of various polarization states created by the example of the hand held device of FIGS. 8-10 and 11-13, in accordance with one embodiment of the present invention.

DETAILED DESCRIPTION

According to one embodiment of the present invention, disclosed herein is a hand held device for examination of a patient's retina. Embodiments of the present invention permit a doctor to examine the retina of a patient without the use of mydriatic eye drops and therefore without dilating the pupils. As will be described below, some embodiments of the present invention use a combination of infrared (IR) and visible light, along with various optical techniques, to capture images (such as static still images and dynamic video images) of a patient's retina. Embodiments of the device and methods may be used to examine patient's eyes, such as the retina of a human or an animal.

Figure 1:
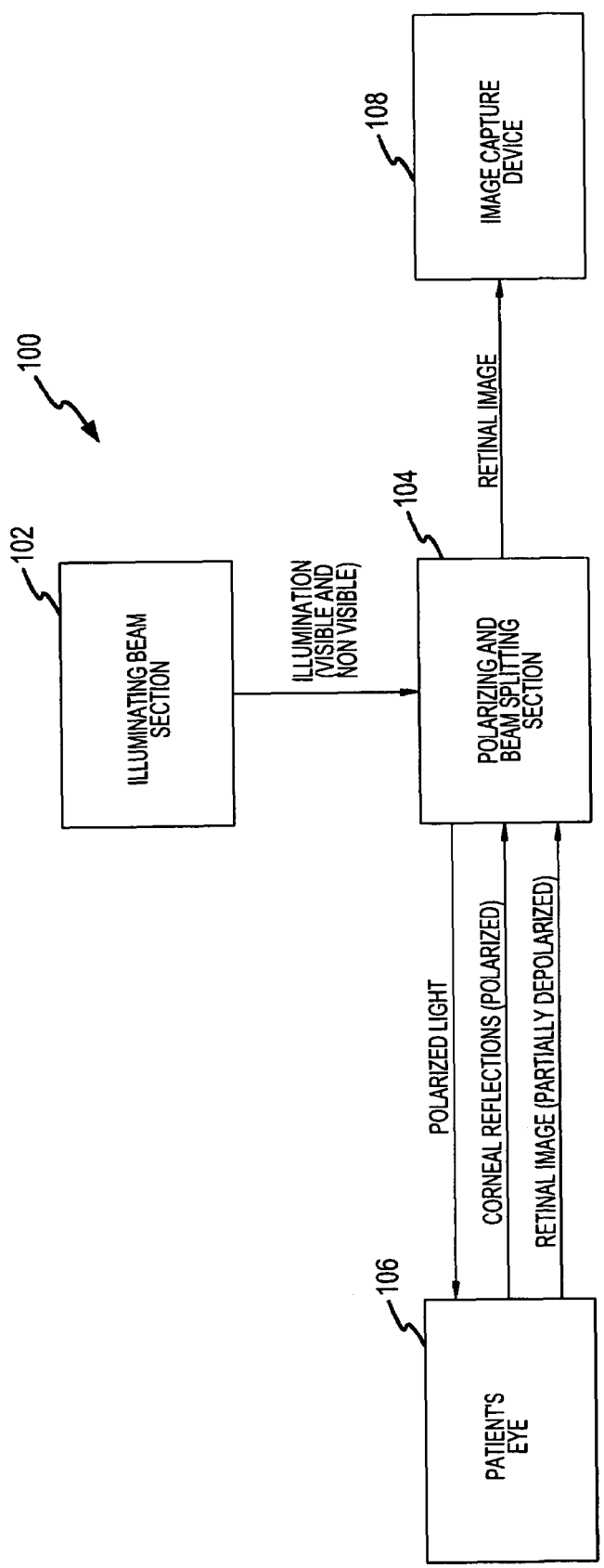
FIG. 1 illustrates a block diagram of a hand held device for examining a patient's retina, in accordance with one embodiment of the present invention.

FIG. 1 illustrates a block diagram of an example of hand held device (100) for examining a patient's retina, in accordance with one embodiment of the present invention. An illuminating beam section (102) generates visible or non-visible light beams or light rays having desired spectral content that can be used, after processing by the polarizing and beam splitting section (104), for illuminating the patient's retina (106) during the examination. For instance, the illuminating beams may include infrared (IR) or visible light. As described below, IR light can be used to perform the examination through the patient's undilated pupil, without the need for mydriatic drops, and the images received and processed by the hand held device can be real-time, dynamic video images of the retina. Visible light can be used for short time periods (i.e., approximately 0.1 to 0.008 seconds or other time periods) to image the retina for static or still images. As used herein, the terms light, light beam(s), light ray(s) are used interchangeably, and the term light can include visible and non-visible illumination such as IR light.

The illuminating beam section, in some embodiments, can generate light selectively having two or more spectral ranges, and alternatively couple light of different spectral ranges into the polarizing and beam splitting section. For instance, the illuminating beam section can provide IR light to view the retina in real-time (i.e., dynamic real time video images), then be controllably switched to provide a pulse of visible light to take a still image (i.e., a high resolution static image), then be controllably switched to again provide IR light. Hence, a hand held device according to an embodiment of the present invention can provide both video and high quality still photographic capabilities.

Furthermore, in another example, the illuminating beam section can provide IR light to view the retina in real-time (i.e., dynamic real time video images), then be controllably switched to provide light with an appropriate exitation wavelength to excite fluorescein dye to perform a fluorescein dye study.

In another example, the illuminating beam section can provide IR light to view the retina in real-time (i.e., dynamic real time video images), then be controllably switched to provide light with an appropriate exitation wavelength to excite indocyanin green dye to perform an indocyanin green dye study.

In another example, the illuminating beam section can provide light with an appropriate exitation wavelength to excite fluorescein dye to view the retina in real-time (i.e., dynamic real time video images), then be controllably switched to provide light with an appropriate exitation wavelength to excite indocyanin green dye to perform an indocyanin green dye study. This example provides a device that can perform both fluorescein and indocyanin dye studies, nearly simultaneously, to provide images of retinal circulation and choroidal circulation, for example.

The polarizing and beam splitting section of the hand held device receives the light beam(s) from the illuminating beam section. The polarizing and beam splitting section generates polarized light beam(s) to illuminate the patient's retina. Generally, the polarizing and beam splitting section imparts a specific polarization state on the light directed towards the patient's eye, and does not transmit (i.e., diverts, reflects, or otherwise extinguishes) light received from the cornea (rather than from the retina) that has a specific polarization state.

Generally, the polarized light beam travels towards the patient's retina along an optical path that is disposed at an angle (such as 90 degrees) relative to the light beam from the illuminating beam section. At the patient's eye, a portion of the polarized beam is then partially reflected by the patient's cornea, represented in FIG. 1 as the corneal reflections (polarized), back in the direction of the polarizing and beam splitting section. Another portion of the polarized beam enters the eye through the pupil, illuminates the patient's retina, and this generates a reflected retinal image (generally de-polarized) which travels in the direction of the polarizing and beam splitting section.

The polarizing and beam splitting section transmits (i.e., does not reflect or block) certain portions of the retinal image, defined by their polarization states, on through to an image capture device (108) (such as a CCD or CMOS capture device, or other digital or non-digital image capture device). The image capture device may include optics to process the retinal image.

As to the polarized corneal reflections, the polarizing and beam splitting section receives the polarized corneal reflections and does not substantially transmit these polarized corneal reflections to the image capture device (i.e., the corneal reflections are diverted, reflected, or otherwise extinguished). Hence, the image capture device receives retinal images having certain states of depolarized light but does not substantially receive the polarized corneal reflected light.

Various embodiments of the present invention are disclosed herein, including various features of a hand held device for examining a patient's retina. It is understood that a hand held device could be formed that includes one or more, but not all, features disclosed herein.

Figure 2:
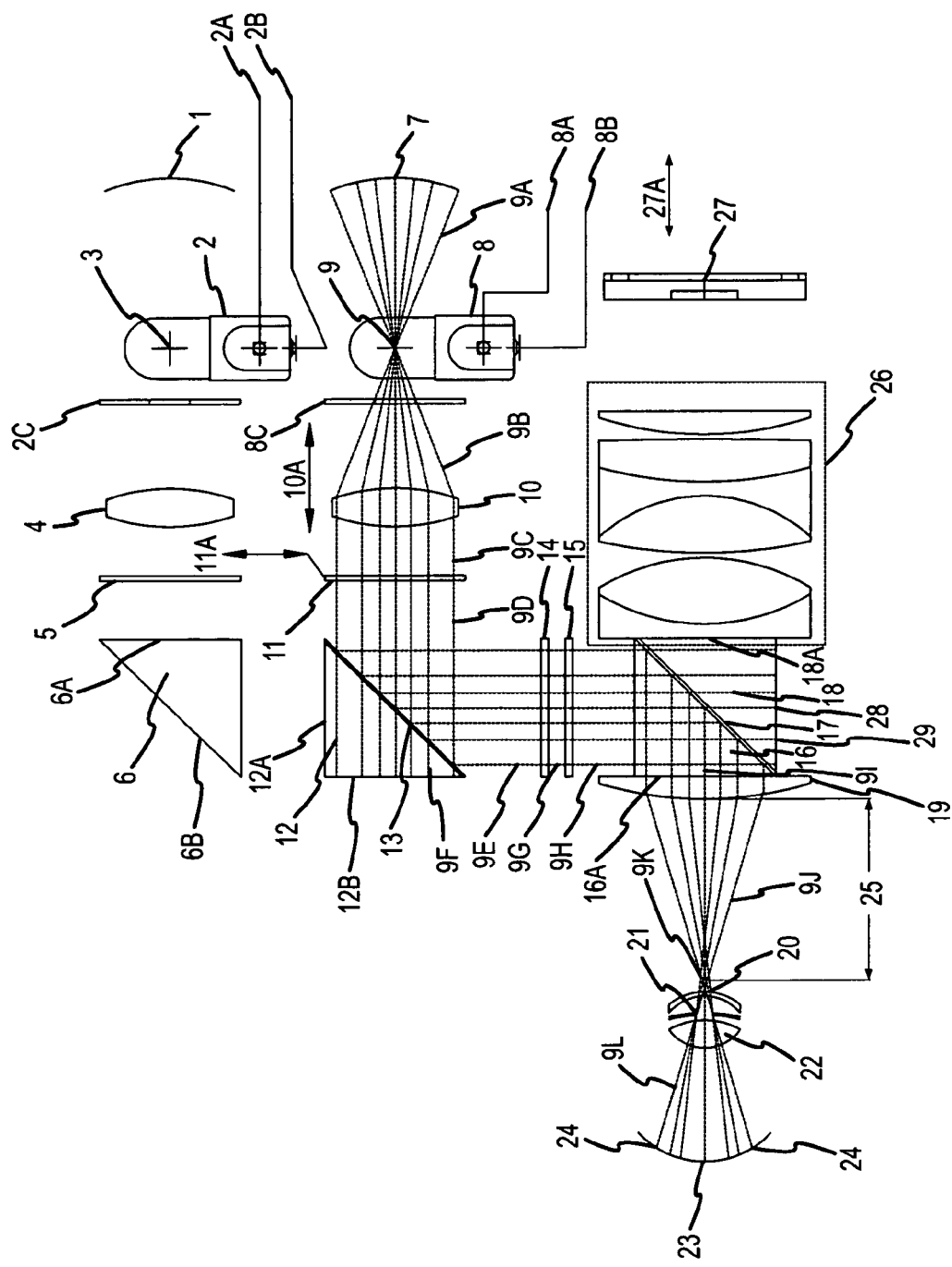
FIG. 2 illustrates an example of a hand held device having various optical elements for generating an illumination beam to illuminate a patient's retina with illumination of a first spectral range, in accordance with one embodiment of the present invention.

FIGS. 2-7 illustrate examples of optical components for optically processing light within a hand held device, in accordance with one embodiment of the present invention. In FIG. 2, two light paths are provided for illuminating a patient's retina. A first path is created through light source 8, variable diaphragm 8C, lens 10, filter 11 and is incident on prism 12; and a second path is created through light source 2, variable diaphragm 2C, lens 4, filter 5 and is incident on prism 6. The first and second paths then each pass through a common path after passing through at beam splitter 13. Each light source/filter combination provides light of different wavelengths, for instance IR light and visible light. Alternatively, a single light source may be used with a two-mode selectable filter as will be described below with reference to FIGS. 8-17 for example.

In one example, the IR light source is the default light source that is normally on and used during examination (while the visible light source is off) in order to provide real-time, dynamic images (such as real-time video or streaming video) of the patient's retina; and the visible light source is turned on (while the IR light source is preferably off) for a brief period of time (i.e., 0.1 seconds to 0.008 seconds or other ranges) in order to provide high resolution static images that may be captured as digital images that may be stored, processed, and analyzed.

In one example, a device may provide far red, near IR, and regions of the visible spectrum between 380 and 760 nm. In one embodiment, the far red and near IR spectral bandwidths between 700 and 850 nm are used as one illuminating beam source, and the visible spectral bandwidth between 580 nm and 740 nm is used for a second illuminating beam source. The use of two discrete bandwidths of illumination is advantageous in allowing a specific amount of visible illumination (the far red from 700 to 760 nm) to be mixed with near IR illumination between 760 and 850 nm. This creates a visible red illuminating circle for purposes of fixation by the patient being examined while not being visually intrusive and uncomfortable for the patient. The bulk of the illumination from the IR portion of the band, while not visible to the patient, provides sufficient illumination to the image detector, which has response to the IR bandwidth described based on it's quantum efficiency vs. wavelength. The intensity of the Far Red/IR band may also be controlled with a variable iris diaphragm and/or a lamp intensity control. This allows the operator to allow more or less visible illumination to fall on the subject's retina to create a pupil response contraction, allowing the operator to optimize the patient's pupil size for maximum image resolution of the patient retina. The second bandwidth between 580 and 740 nm falls within the spectral range of interest for retinal features and disease pathologies and is more transparent to the lens of the eye. The bandwidth spread of 580 to 850 nm (270 nm) in combination with the optics described above, may result in a high resolution broadband image of the retina at a single plane of focus at the detector. This provides an instrument capable of illuminating the retina with the two afore mentioned bandwidths and creating high resolution, broadband images without compensating focus adjustment for the two bandwidths.

In this example of FIGS. 2-7, lamp 8 and lamp 2 are selectively turned on/off (through wires 8A/B and 2A/B) so that one lamp provides the light source. In the first optical path of light source 8, a spherical reflector 7 is provided. An iris diaphragm 8C provides a selectively variable aperture for the light source, and the variable aperture can be selectively adjusted if desired to control stray illumination from the light source. The voltage applied to the light source may be adjusted to control the light source intensity.

From the variable diaphragm 8C, light enters lens 10 then passes through filter 11. In one example, light source 8 is positioned at the focal point of lens 10. Filter 11 may transmit or pass infra-red (IR) light with wavelengths between approximately 760 and 850 nm, although other wavelengths may be used depending upon the implementation. Light from the filter 11 then is incident upon a beam splitter 13 which may be bonded to the surface of the prism 12.

Prism 12 has a beam splitter 13 attached or applied to its front angled surface. An anti-reflective coating may be provided on top surface of the prism and a non-reflective coating may be applied to its rear surface.

In one example, the beam splitter 13 is a polka-dot beam splitter with approximately a 50/50 reflection/transmission ratio over a wide spectral range (including visible and IR light) and accepting of incidence angles of approximately 0 to 45 degrees on either surface of the beam splitter.

When light from lamp 8 is active, it strikes beam splitter 13 and a portion (i.e., approximately 50 percent) of the light passes, without reflection, through the beam splitter and enters the prism and strikes the non-reflective surface of the prism and is extinguished there; while another portion (i.e., approximately 50 percent) of the incident light is reflected at a 90 degree angle by the beam splitter 13 and does not enter prism 12. The reflected light is represented as light 9E in FIG. 2.

In the second optical path of light source 2, a spherical reflector 1 is provided. An iris diaphragm 2C provides a selectively variable aperture for the light source, and the variable aperture can be selectively adjusted if desired to control stray light from the light source. The voltage applied to light source 2 may also be adjusted to control the light source intensity.

From the variable diaphragm 2C, light enters lens 4 then passes through filter 5. In one example, filter 5 transmits or passes visible light of wavelengths between approximately 600-750 nm, although other wavelengths may be used depending upon the implementation. Light from the filter 5 is incident upon a prism 6 which acts as an angled mirror. In one example, the prism 6 may have an anti-reflective coating 6A on its front surface and a reflective surface 6B on its angled surface. An anti-reflective coating may be provided on its exit surface if desired.

Figure 3:
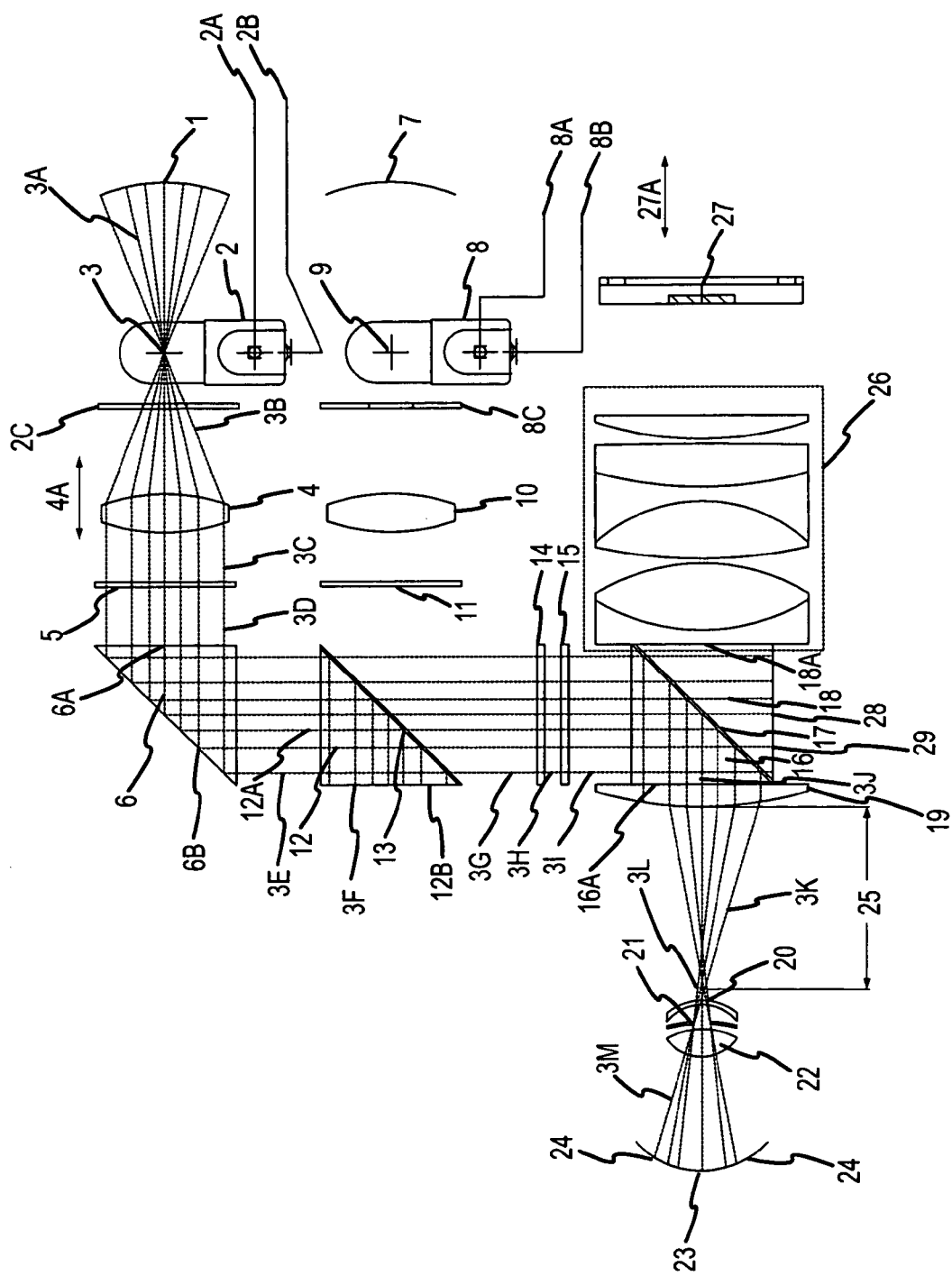
FIG. 3 illustrates an example of various optical elements for generating an illumination beam to illuminate a patient's retina with illumination of a second spectral range, in accordance with one embodiment of the present invention.

When light from lamp 2 is active and after reflecting from prism 6, the light enters through the top surface of prism 12 (see FIG. 3) and strikes the beam splitter 13. As shown in FIG. 3, a portion (i.e., approximately 50 percent) of the light is reflected by beam splitter 13 and then strikes the non-reflective rear surface 12B of the prism 12 and is extinguished there. Another portion (i.e., approximately 50 percent) of the light passes, without reflection, through the beam splitter 13 as is represented in FIG. 3 as light 3G.

The rays 9E of FIG. 2 (and rays 3E of FIG. 3) are incident upon diffusing element 14 to produce a generally uniform illumination. Conventional diffusers may be used as diffuser 14 depending upon the implementation. In one example, diffuser 14 is a holographic diffuser with a 90 percent transmission efficiency over a wide spectral range (including visible and IR light) and provides homogeneous light distribution (shown as rays 9G in FIG. 2 and 3H in FIG. 3) on its output surface.

The output light from the diffuser 14 is incident upon polarizer 15 which transmits rays 9H. The polarizer transmits a desired polarization state of light (i.e., linear S electric vector). Conventional polarizers may be used as polarizer 15 depending upon the implementation. In one example, polarizer 15 is a wire grid polarizer having a parallel grid of microwires capable of processing light over a wide spectral range (including visible and IR light), with high efficiency in maintaining polarization states. In one example, a wire grid polarizer will reflect a portion of light with its electric field vector parallel to the grid wires, and will transmit light with its electric field vector perpendicular to the grid wires. In one example, a wire grid polarizer may be used as described in U.S. Pat. No. 6,122,103 assigned to Moxtek of Orem, Utah, the disclosure of which is hereby incorporated by reference in its entirety.

The rays 9H are incident upon prism 16. Prism 16 may have a antireflective coating on its top surface and a polarizing beam splitter 17 may be optically bonded to its angled surface. A lens may be optically bonded using optical adhesive to provide an index of refraction match) to the front surface 16A, in one example. Another prism 18 may be optically bonded to the polarizing beam splitter 17, so that prisms 16, 18 form a cube beamsplitter. Prism 18 may be provided with a non-reflective bottom surface in order to extinguish any light incident upon bottom surface.

Conventional beam splitting polarizers may be used as polarizing beam splitter 17 depending upon the implementation. In one example, polarizing beam splitter 17 is a wire grid polarizing beam splitter having a parallel grid of microwires capable of processing light over a wide spectral range (including visible and IR light), with high efficiency in maintaining polarization states. In one example, a polarizing beam splitter could include a polarizing wire grid as described in U.S. Pat. No. 6,122,103, referenced above. In one example, a wire grid polarizing beam splitter will reflect a portion of light with its electric field vector parallel to the grid wires, and will transmit light with its electric field vector perpendicular to the grid wires.

In one example, polarizing beam splitter 17 reflects linear-S polarized light, but allows light of other polarization states to pass through without reflection.

As shown in FIG. 2, light 9H enters prism 16 and some portion of light is reflected by polarizing beam splitter 17 towards the patent's eye, while a portion of light 9H is not reflected by polarizing beam splitter 17 and is extinguished when it strikes bottom surface of prism 18.

Rays 9H, by virtue of their polarization state, are reflected at 90° by polarizing beam splitter 17 and travel through prism 16 and are represented by rays 9I, and those rays pass through objective lens element 19 which has a plano surface at 16A optically bonded to prism 16 and has a convex forward surface. Lens element 19 is a positive element.

The rays (9I), upon refraction at the front surface of lens (19), are shown as rays (9J) and converge at the convergence point (9K). Convergence point (9K) can be located by the user (when controlling the distance of the instrument from the eye) so that point (9K) is just forward, axially, to corneal surface (20), in one example. These rays then pass through the cornea (20) and through the patient's pupil (21), where they are refracted by the patient's lens (22) and form rays (9L). Rays (9L) coming out of the patient's lens (22) are incident upon the surface of the retina (23) in a circle of illumination shown as bundle (24) in FIG. 2.

Stated differently, in one example lamps (2) and (8) may be alternately illuminated by applying power through wires (2A) and (2B) or (8A) and (8B). Lamp (8) has its filament (9) located near the primary focal point of lens (10). Spherical reflector (7) is located such that its radius of curvature is coincident with lamp filament (9). Variable aperture (8C) restricts the rays emitted by (9) to fall on the maximum clear diameter of lens (10). Lens (10) may be a condenser lens utilizing conventional spherical surfaces or aspheric surfaces. Rays (9B), after undergoing refraction by lens (10), are generally parallel, indicated by (9C). Spherical reflector (7) redirects rays from the filament back through their axis, thereby improving the captured illumination flux density emitted by (9). Lens (10) may be displaced axially, indicated by arrows (10A). Filter (11) may be interchangeable. Interchanging filter (11) allows selective bandwidths of illumination to be transmitted, indicated by (9D). Transmitted rays (9D) are reflected through 90 degrees by beam splitter (13). Beam splitter (13) may be mounted to 90 degree prism (12) by means of clear optical adhesive, allowing transmission through prism (12). Beam splitter (13) is a "polka-dot style" beam splitter. A polka-dot beam splitter has equal areas of miniature reflective surfaces and transmission windows via a clear substrate. The reflective and transmitting elements of the beam splitter each represent 50 percent of its surface area. Polka-dot beam splitters exhibit broadband characteristics for both transmission and reflection and have a much greater acceptance angle than thin film beam splitters. In one example, 50 percent of rays (9D) are reflected through 90 degrees by beam splitter (13), becoming rays (9E). The remaining 50 percent of rays (9D) are transmitted through beam splitter (13) and prism (12) and are incident upon surface (12B) which may be a black, non-reflective coating applied to prism (12). Rays (9E) are incident upon diffuser (14) which may be a holographic diffuser to improve the beam transmission efficiency. After passage through diffuser (14) the diffused rays (9G) are incident upon polarizing filter (15), represented by (3) in FIG. 6A-6C. Transmitted rays (9H) are represented by (4A) and (4B) in FIG. 6A. Rays (9H) are incident upon polarizing beam splitter (17), defined by (5) in FIG. 6A-6C. Polarizing beam splitter (17) is optically mounted between 90 degree prisms (16) and (18), using clear optical adhesive. Rays (9H) are reflected through 90 degrees by polarizing beam splitter (17) indicated by rays (9I) and ray (6) in FIG. 6A. In FIG. 2, rays 29 which represent rays (4C) in FIG. 6A that are incident on surface 28 which is a black, non reflective surface. Rays (9I) are refracted by lens elements (19) which are conjugate with lens elements (10) and (4). Refracted rays (9J) converge at point (9K). Convergence point (9K) may be moved axially, indicated by (25) by the axial movement of (10) indicated by (10A). The adjustability of this convergence angle allows for maximum retinal illumination area (24), based on pupil diameter (21). At its point of maximum convergence (9K), the small beam diameter facilitates maximal retinal illumination area through a small pupil.

FIG. 3 illustrates an alternative illumination path by illuminating lamp 2, as opposed to illuminating lamp 8. The spherical reflector 1, variable diaphragm 2C, and lens 4 may be identical to components 7, 8C, and 10 described with reference to FIG. 2. In one example, light source 2 is positioned at the focal point of lens 4.

Selectively illuminating lamp (2) or lamp (8) allows rapid alternation of the illumination wavelengths/spectrum. Lamp (2) can have a similar optical arrangement as lamp (8). Filter (5) may be interchangeable. For example, by placing an infrared transmitting filter (5) and a green filter as filter (11), one may rapidly alternate between infrared and green illumination. The timing of the alternate illumination sources is based on the filament rise and fall time between maximum and minimum output, the minimum output being the threshold of illumination able to be sensed by a detector in the system. Alternatively, lamps (2) and (8) may be short-arc discharge lamps with rapid rise and fall time when compared to the aforementioned filament lamps. Alternately, one lamp may be a xenon or other flash tube, allowing the device to alternate between a filament or discharge lamp and short duration flash lamp pulse.

The rays 3C exit lens 4 and are incident upon filter 5, and the light 3D output from filter 5 enters the front surface 6A of prism 6 which may have a thin film antireflective coating applied thereto. These rays are incident upon angled surface 6B, which may be a reflective metalized surface applied to prism 6. Alternatively, prism 6 may not have a reflective surface at 6B and may instead rely on total internal reflection defined by Snell's Law and create a 90° reflection of rays 3D upon surface 6B which are then the emergent rays 3E. Rays 3E are incident upon surface 12A of prism 12, as described above. Fifty percent of rays (3E) pass through beam splitter (13), becoming rays (3G). Fifty percent of rays (3E) are reflected through 90 degrees, becoming rays (3F) which are incident on surface (12B). Rays (3G) pass through (14) in identical fashion to rays (9E) in FIG. B2 Rays (3H) through (3M) behave in the same manner as those described by (9G) through (9L) in FIG. 2.

Figure 4:
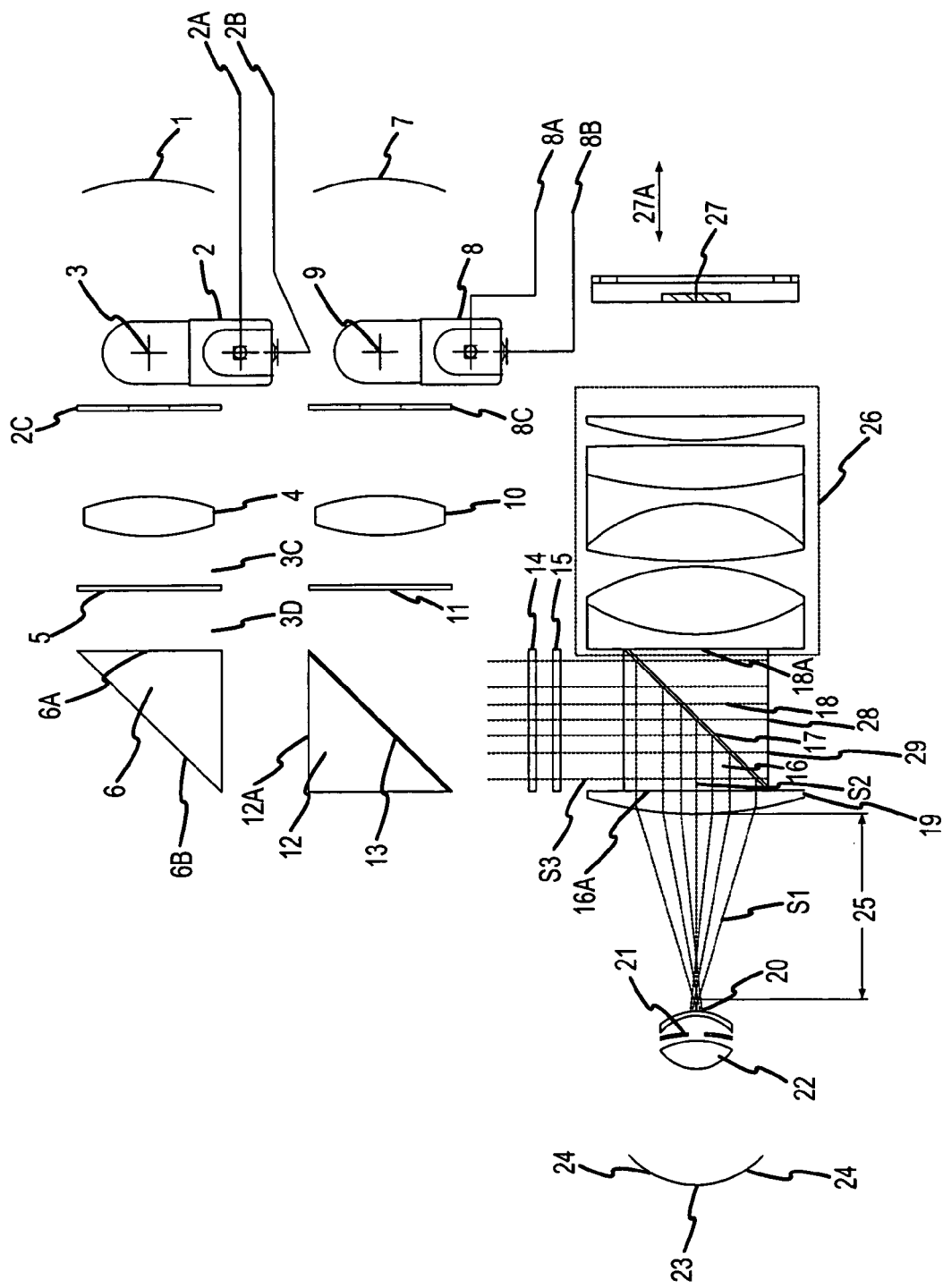
FIG. 4 illustrates an example of diversion of corneal reflections by a hand held optical device, in accordance with one embodiment of the present invention.

FIG. 4 illustrates how corneal reflections are diverted from the image capture device/detector, in accordance with one embodiment of the present invention. Corneal reflections are shown as rays (S1) and correspond to rays (9), Stokes vector (10), and (10A) in FIG. 6B. Rays (S1) are refracted by lens (19), becoming rays (S2) and are incident on polarizing beam splitter (17) as indicated by ray (11) in FIG. 6B. In FIG. 4, rays (S2) are reflected by 90 degrees by polarizing beam splitter (17) becoming rays (S3), represented by ray (12) in FIG. 6B. In FIG. 4, rays (S3) are incident on polarizer (15). Hence, corneal reflections S1 are diverted away from the optics 26 and imager 27.

Figure 5:
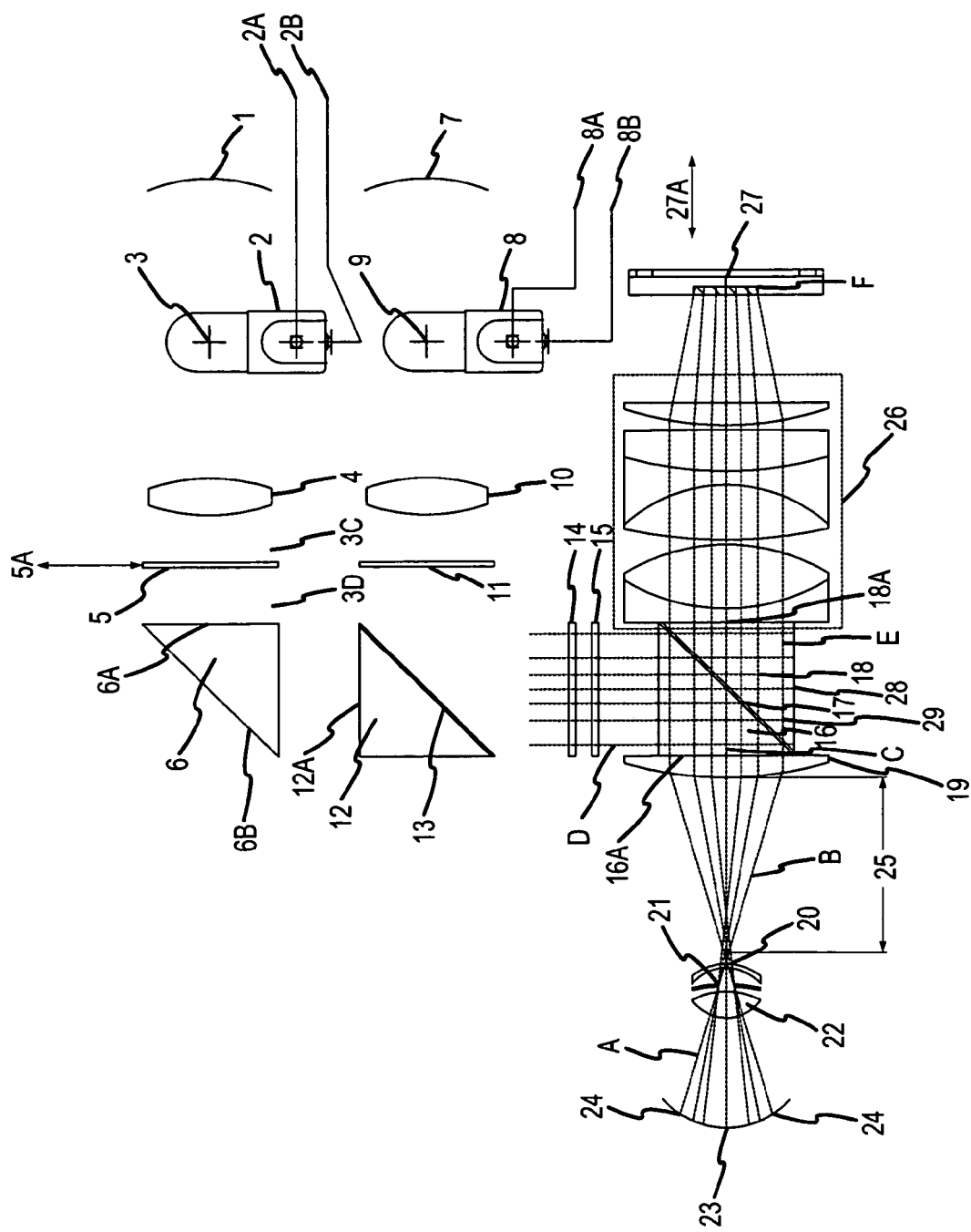
FIG. 5 illustrates an example of receiving an image of a patient's retina and passing that image to a surface of a detector, in accordance with one embodiment of the present invention.

FIG. 5 illustrates optical processing of the retinal image, in accordance with one embodiment of the present invention. Rays (A) are reflected by the fundus or retinal surface (23) and pass through the patient's crystalline lens (22), pupil (21), and cornea (20), becoming rays (B). Rays (B) are refracted by lens (19), becoming rays (C) which are represented by rays 15, 16 in FIG. 6C. In FIG. 5, rays (C) are incident upon polarizing beam splitter (17) and are reflected by 90 degrees, becoming rays (D), represented by rays (19) in FIG. 6C. In FIG. 5, rays (D) are transmitted through polarizing beam splitter (17), becoming rays (E), represented by rays (17) in FIG. 6C. In FIG. 5, lens (19) and the first element of lens group (26) may have plano surfaces, which are optically bonded to prism faces (16A) and (18A). The lens 19, 26 may have an index of refraction similar to prisms (16) and (18). Optically bonding the lenses and prisms reduces the number of glass/air interfaces, helping to minimize internal reflections and ghosting. Rays (E), which form a virtual image of retina (23) are refracted by lens elements (26), forming a real image of retina (23) at surface (F) of detector (27). Detector (27) can be a CCD or CMOS image sensor. Focus compensation for eyes of varying diopter range is achieved by axial adjustment of detector (27), indicated by (27A). Hence, certain depolarized components of the retinal image are passed through to the image capture device/detector 27.

Figure 6A:
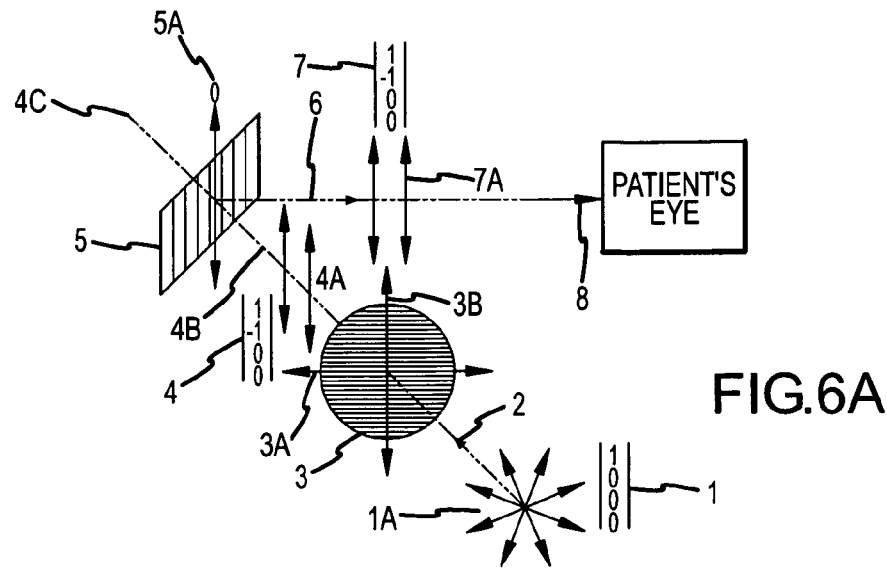
FIGS. 6A-6C illustrate various polarization states of light as light is processed by polarizers 15, 17 of FIGS. 2-5, in accordance with one embodiment of the present invention.
Figure 6B:
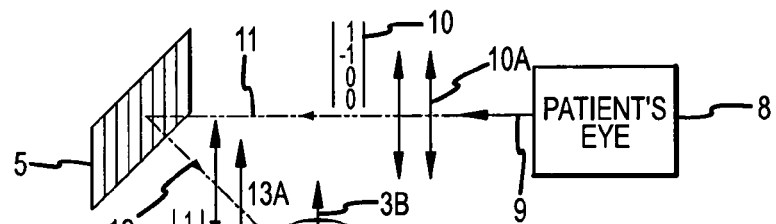
Figure 6C:
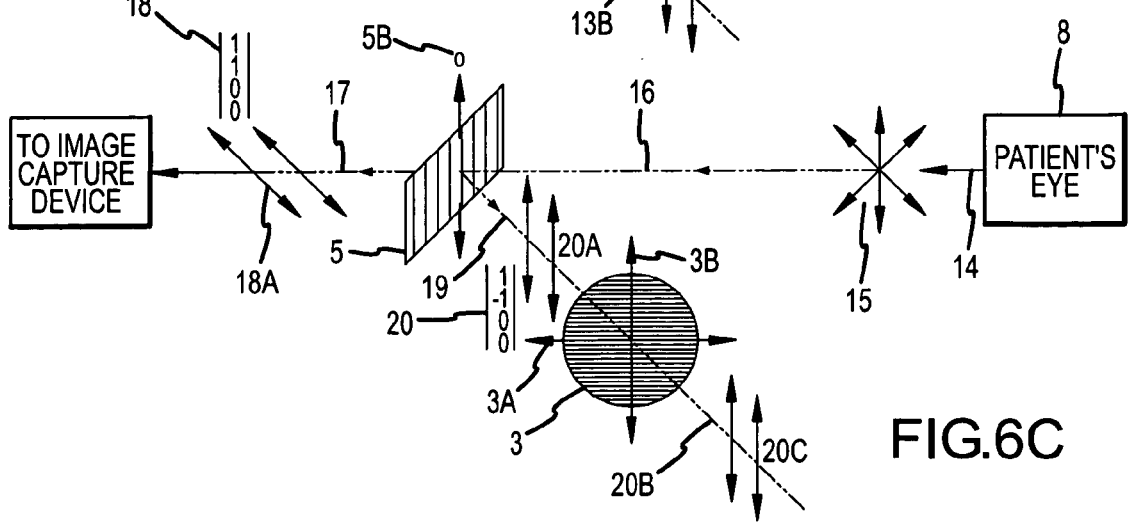

FIGS. 6A-C illustrate various states of polarization of light as light is processed within the optics shown in FIGS. 2-5. FIG. 6A illustrates a process wherein illumination 1A from a light source is polarized and transmitted to the patient's eye 8, in accordance with one embodiment of the present invention.

In FIG. 6A, randomly polarized illumination, represented by bundle (1A), ray (2), and Stokes vector (1), is incident upon wire grid polarizing element (3) the wire grid axis being parallel to axis (3A). Note that wire grid polarizing element (3) in FIGS. 6A-6C corresponds to polarizer (15) in FIGS. 2-5. Polarizing element (3) transmits linear, vertical radiation (4A) defined by Stokes vector (4) which is S plane when viewed in the plane of reference as shown, relative to polarizing beam splitter (5). Note that polarizing beam splitter (5) in FIGS. 6A-6C corresponds to splitter (17) in FIGS. 2-5. Vertically oriented radiation (4B) is incident upon the wire grid polarizing beam splitter element (5) oriented at 45 degrees relative to the beam axis (4B) and the surface plane of polarizer (3) The wire grid orientation of polarizing beam-splitter (5), whose wire grid axis is represented by (5A), is transverse (90 degrees) to the wire orientation axis of polarizer (3). It reflects light (4B) through 90 degrees, becoming ray (6) which is linearly and vertically polarized S plane radiation (7A) having Stokes vector (7). Ray (4C) represents a small percentage of non-vertically polarized radiation present in ray (4B) which is transmitted by polarizing beam splitter (5). Wire grid polarizers, when arranged in the spatial orientation shown, will selectively reflect vertical linear radiation and if polarizer (3) were rotated by 90 degrees, making the wire grid axis parallel to (3B), horizontally oriented linear radiation would be produced, which would be transmitted by polarizing beam splitter (5). This allows the selective transmission or reflection of polarized radiation, based on the wire grid orientation relationship between the polarizers (3), (5). A linearly polarized beam parallel to the axis of the wire grid will be reflected by the wire grid and a linearly polarized beam transverse to the orientation of the wire grid will be transmitted. Polarized light (8) is incident upon the eye.

FIG. 6B illustrates a process for diverting polarized corneal reflections 9 from the patient's eye received by a hand held device, in accordance with one embodiment of the present invention. Being linearly polarized, the corneal specular reflection (9) is returned from the eye. This reflection (9) is also referred to as Purkinjie 1. The reflected S plane polarized wave is represented by (10A), Stokes vector (10) and ray (11). Ray (11) is incident upon the polarized beam splitter (5) and is reflected through 90 degrees, represented by ray (12) back to (3) and transmitted through polarizer (3) due to its polarization orientation. Therefore, reflected ray (11) has minimal transmission through beam splitter (5) because the corneal reflection (9) is polarized and because the polarized beam splitter (5) is disposed at an angle and reflects the polarized corneal reflection 9 out of the optical path of the imaging detector.

FIG. 6C illustrates a process for transmitting the partially depolarized retinal image from the patient's eye towards the image capture device/imaging detector. Illumination (14) is the retinal image partly depolarized by reflection from the retina. This is represented by bundle (15A) and ray (16). Although experimental models frequently represent the eye fundus as an ideal depolarizer, other data demonstrates that illumination reflected from the fundus varies in its state of polarization. Longer wavelength illumination, particularly in the near infrared region between 760 and 900 nanometers, exhibits a greater level of depolarization than shorter wavelengths. Bundle (15) therefore represents states of varying polarization intensities. Ray (16) is incident upon polarizing beam splitter (5). P plane magnetic polarized rays represented by rays (17), (18A) and Stokes vector (18) are transmitted through polarizing beam splitter (5). S plane electric vector radiation is reflected through 90 degrees by polarizing beam splitter (5), represented by rays (19), (20B) and (20A), (20C) and Stokes vector (20). Hence, a portion of the retinal image is passed through polarizing beam splitter (5) towards the image capture device/detector.

Figure 7:
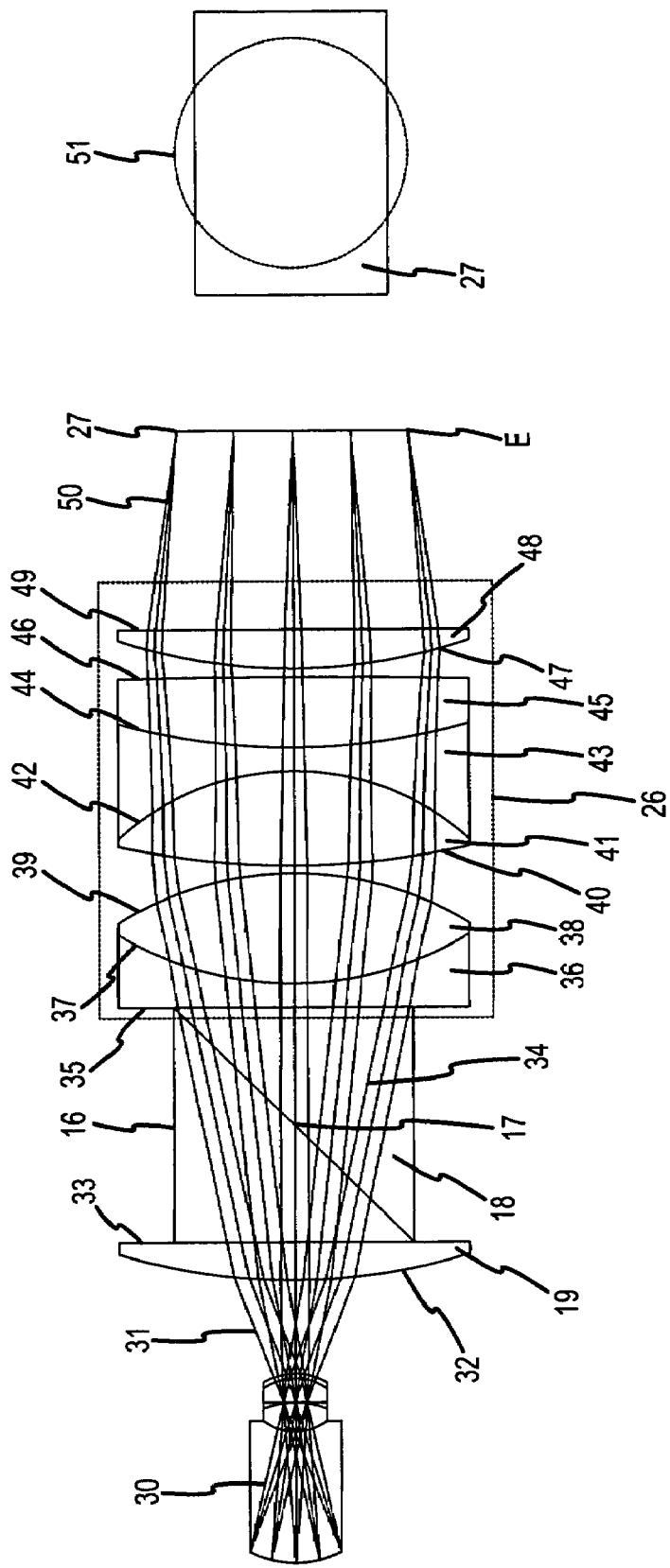
FIG. 7 illustrates an exploded view of optic 26 of FIGS. 2-5, in accordance with one embodiment of the present invention.

FIG. 7 illustrates an exploded view of optics 19, 16, 18, and 26 in FIGS. 2-5 in accordance with one embodiment of the present invention. It is understood that FIG. 7 describes a specific implementation and that various parameters described can be changed or altered depending upon the particular implementation. Rays (30) illustrate the reflected image of the retina which is refracted by the eye, thereby creating rays (31) which are incident on plano convex lens (19) which is 44 millimeters (mm) in diameter and produced from BK7 glass, with a radius (32) of 74.35 mm, a center thickness of 4.8 mm and a plano surface (33) in one example. Rays (31) are refracted by lens (19) resulting in rays (34). Note that additional lens prescription information will be defined in the following sequence: [(Lens number), Lens diameter in mm, Glass type description based on standardized glass nomenclature, (ray entry surface radius in mm), Lens center thickness in mm, (ray exit surface radius in mm), followed by air space (if present) measured at the lens center axis in mm]. Note that standard convention for a ray originating from the left and passing through the optical train from left to right as shown, lens surface radii are defined as positive for surfaces which are convex facing left and radii are negative for lens surfaces that are concave facing right, both relative to the ray origin and that a radius value of 0 represents an infinite radius described as a plano (optically flat) surface. Note that "no air space" following a lens surface indicates an optically cemented surface forming a doublet or triplet lens configuration, also indicated by shared surface radii between two adjacent lenses. In one example, after passing through 90 degree prism 16, wire grid polarizing beam splitter 17, and 90 degree prism 18, rays (34) are incident on plano surface (35) of plano concave lens [(36)-44, SF10], [(35) 0, 3], [(37) 41.55296] and pass sequentially through and are refracted by the following lenses and air spaces: [(38)-44, SSKN8], [(37) 41.55296, 14], [(39)-41.54719, 1 mm air space], [(41)-44, SSKN8], [(40) 99.56286, 12], [(42)-32.29801 no air space], [(43)-44, SF10], [(42)-32.29801, 2.99], [(44) 80.00000 no air space], [(45)-44, SSKN8], [(44) 80.00000, 9], [(46)-1055.58300 1 mm air space], [(48)-44, SF10], [(47) 68.40001, 5], [(49) 0]. After refraction at surface 49, rays (34) become rays (50) which converge at focal plane (E). The circle (51) inscribed on CCD detector active area (27), represents the real image of the retina after passing through and being refracted by the aforementioned optics. The CCD detector may be, in one example, a Kodak KAI-11000CM, with 11 million active image forming pixels, a full frame 35 mm diagonal CCD.

Figure 8:
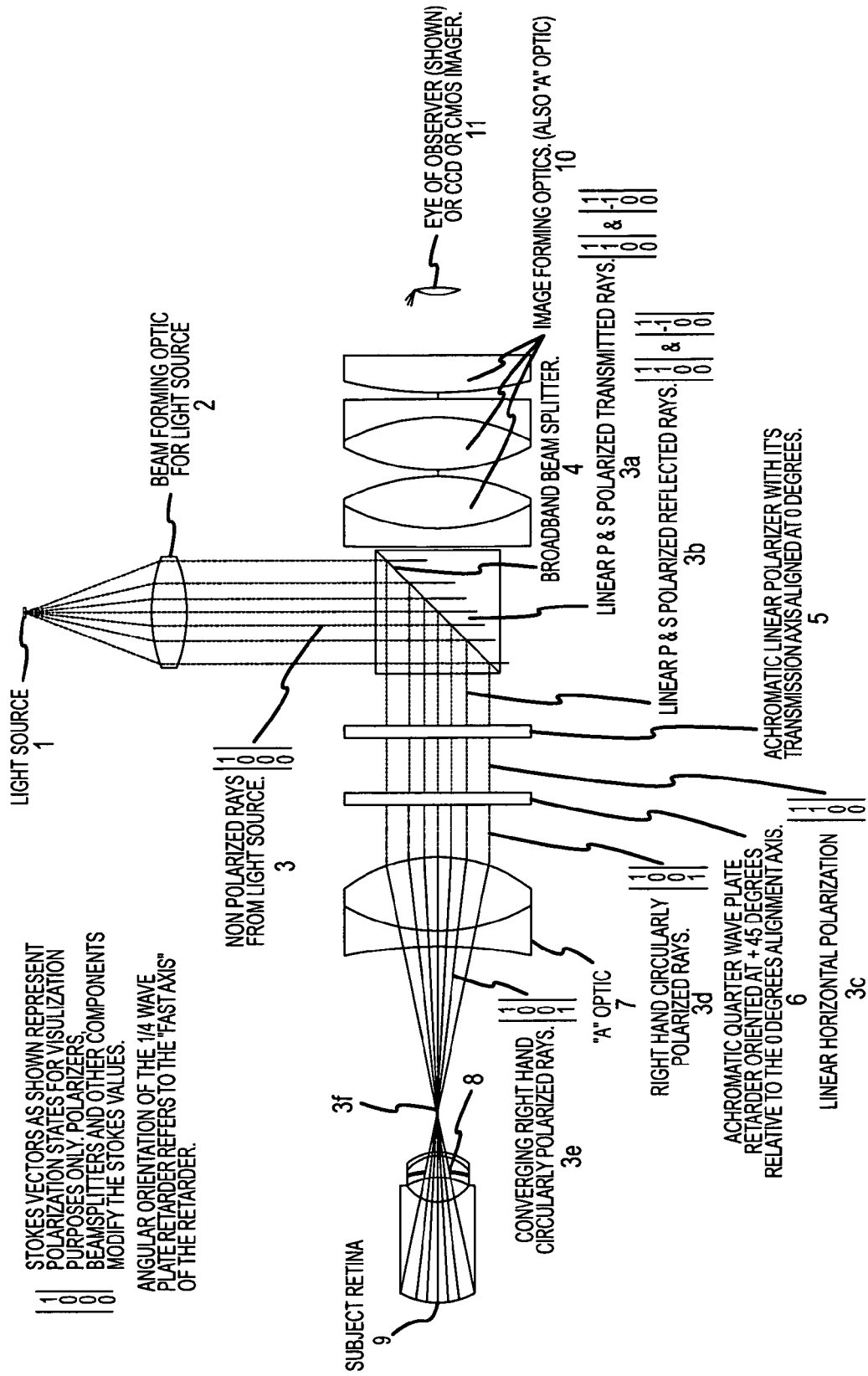
FIG. 8 illustrates another example of a hand held device having various optical elements for generating an illuminating beam for examination of a patient's retina, in accordance with one embodiment of the present invention.

FIG. 8 shows a polarization method relating to Ray path sequence with polarization states. Light source (1) is located at the focal point of beam forming optic (2). Light source (1) may be a filament lamp or arc-type discharge lamp with a spectral distribution range between 380 nanometers and 900 nanometers (NM). This comprises the visible through very near infrared spectrum. After refraction by (2) the generally parallel non-polarized rays reach broad band beam splitter (4). The non-polarized rays (3) are represented by the Stokes vector as shown. Rays (3) are transmitted through (4). Rays (3) are also reflected at a 90 degree angle by the thin film coating present in (4). The P and S wave rays are transmitted and reflected as shown by (3A) and (3B) based on the specific transmission and reflection characteristics of (4) which are generally wavelength and polarization state specific. P and S rays (3b) are transmitted through achromatic linear polarizer (5). The transmission axis of (5) is aligned at 0 degrees (which may best be visualized in FIG. 26A as alignment (8)). After transmission through (5) the rays become linearly, horizontally polarized (P plane). Rays (3c) are transmitted through achromatic quarter wave plate retarder oriented at plus 45 degrees (as visualized in FIG. 26A as axis alignment (5)). The quarter wave plate (6) causes rays (3c) to become right hand circularly polarized (3d). This can be visualized in FIG. 26A as (E1). Rays (3d) are refracted by optic (7) becoming converging RHCP rays (3e). Rays (3e) converge at point (3f) and pass through the subject pupil (8) illuminating subject retina (9).

Figure 9:
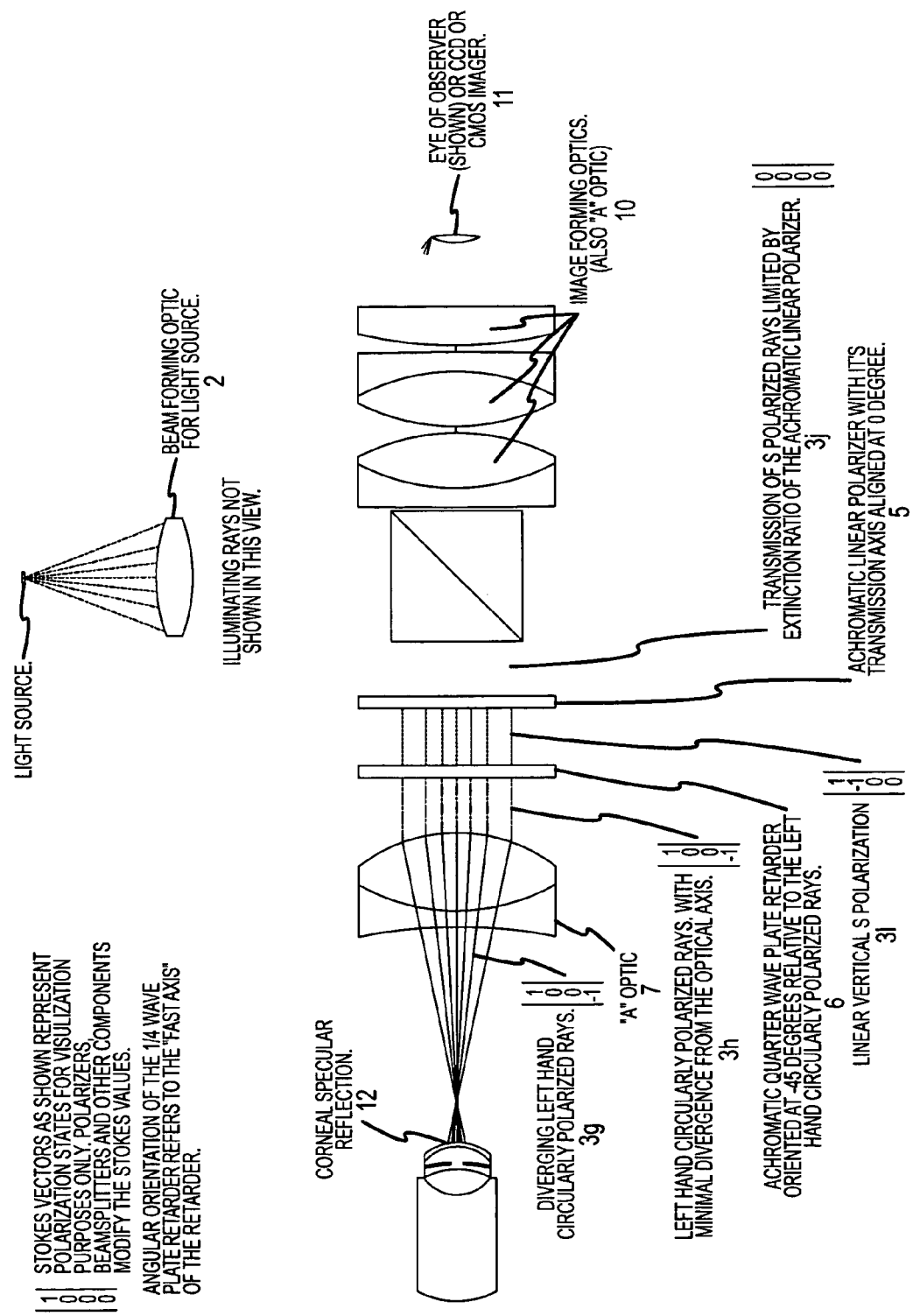
FIG. 9 illustrates an example of extinguishing the corneal reflection associated with the polarized beam of FIG. 8, in accordance with one embodiment of the present invention.

In FIG. 9, the RHCP rays undergo corneal specular reflection at (12) and become diverging left hand circularly polarized rays (3g). Rays (3g) are refracted by optic (7) becoming generally parallel LHCP rays (3h). Rays (3h) can be visualized in FIG. 26B as (D1). Rays (3h) pass through (6) whose fast axis is oriented at minus 45 degrees relative to rays (3h) and can be visualized in FIG. 26B as (7). The passage of rays (3h through 6) causes the LHCP rays to become linearly, vertically S polarized (3i) (as visualized in FIG. 26B as alignment (8) and Stokes vector (B)). Rays (3i) are perpendicular to the transmission axis of (5). This precludes transmission of the S polarized rays limited by the extinction ratio of (5), typically 1000:1 or greater, and can be visualized in FIG. 26B as represented by the 0 Stokes vector (F).

Figure 10:
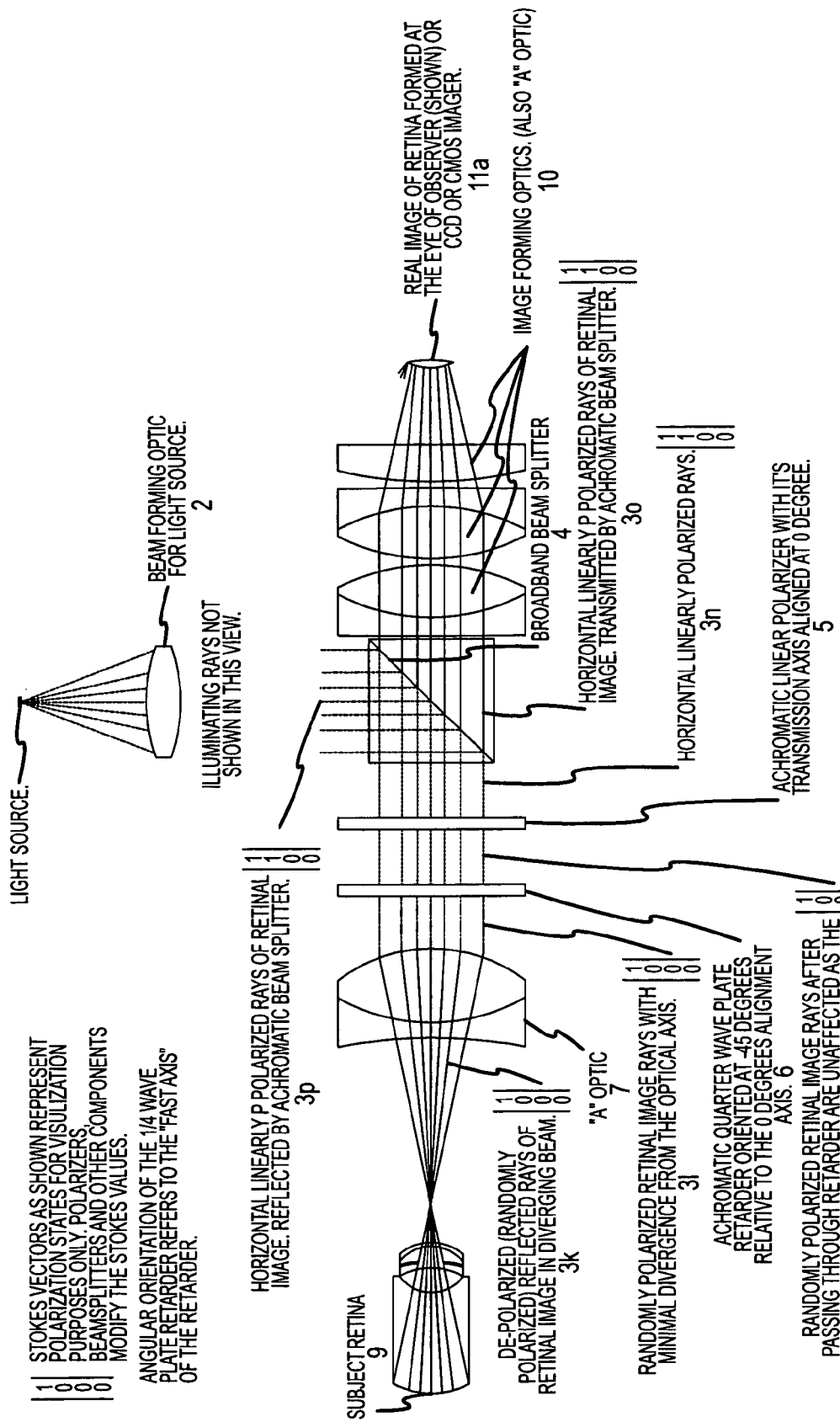
FIG. 10 illustrates an example of transmitting a retinal image to a detector within a hand held device, in accordance with one embodiment of the present invention.

In FIG. 10, the reflection of the rays from subject retina (9) causes de-polarization of the previously RHCP rays. The de-polarized rays exit the subject eye in a diverging beam (3k). Rays (3k) are refracted by optic (7) becoming generally parallel rays (31). Non-linearly polarized rays (31) pass through (6) unaffected as (6) acts as a polarization form converter on linearly polarized rays only. Non-linearly polarized rays (3m) pass through (5) and become horizontal, linearly polarized P plane rays (3n). This polarization sequence can be visualized in FIG. 26C as (A1) through (13). Rays (3n) are reflected by broad band beam splitter (4) becoming rays (3p), which can be visualized in FIG. 26C as rays (15). Rays (3n) are also transmitted by (4) becoming rays (3o) as visualized in FIG. 26C as rays (14). Rays (3o) are refracted by image forming optics (10), forming a real image of the retina at (11A).

Figure 11:
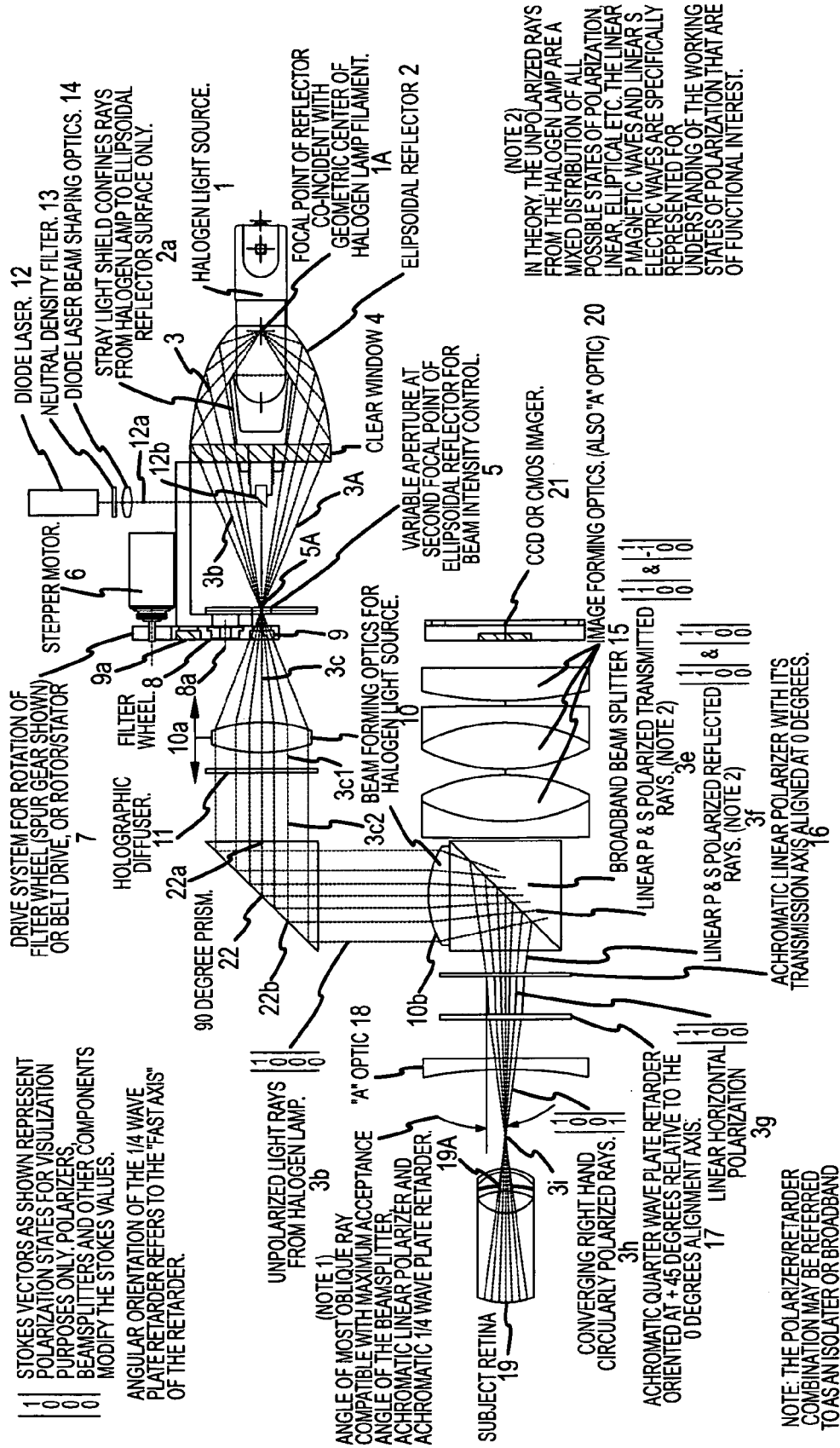
FIG. 11 illustrates another embodiment of a hand held optical device, including a rotatable optical filter for selectively producing illumination beams having different desired spectral content, in accordance with one embodiment of the present invention.
Figure 34:
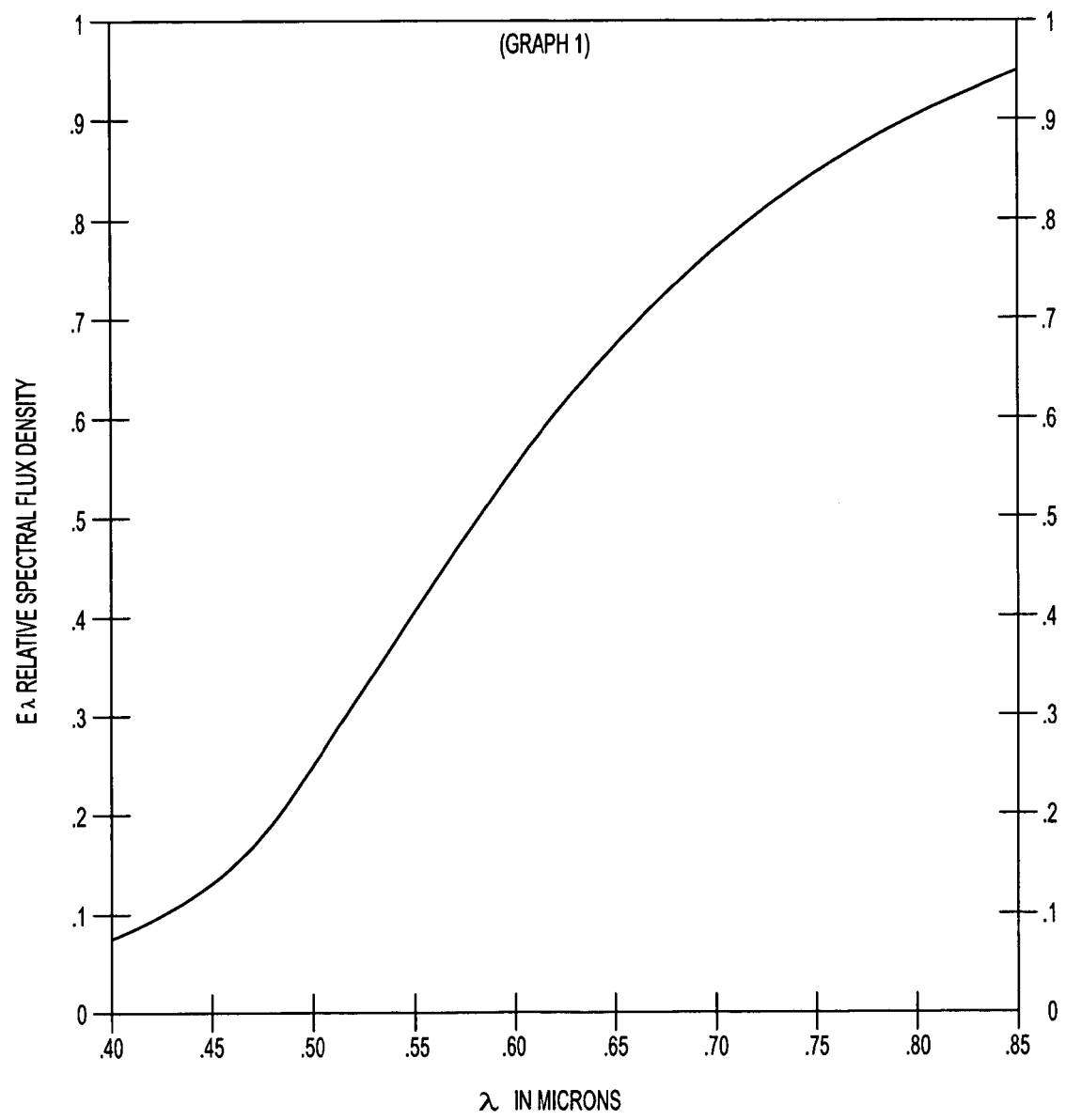
FIG. 34 illustrates a graph of an example of the spectral content of a tungsten filament, in accordance with one embodiment of the present invention.

In FIG. 11, another Polarization Method is shown with a Ray path sequence with polarization states. The filament (1A) of Halogen light source (1) is located at the focal point of ellipsoidal reflector (2) Halogen lamp (1) contains a tungsten filament (1A) which possesses certain "black body" emission characteristics based on the emissive properties of tungsten at specific temperatures when electrically energized. The spectral distribution of energy flux from a blackbody may be expressed by Planck's law. A plot of the energy distribution curve for tungsten at 3000 degrees Kelvin is shown in FIG. 34 (typical for halogen lamps) which shows the utility of a halogen lamp as a spectral source for visible light between 400 and 760 nanometers (nm) and particularly for near infrared radiation between 760 and 850 nm. Halogen lamp (1) may be a bayonet or insertable socket mount type.

In FIG. 11, the rays (3) emitting from halogen lamp (1) are reflected by ellipsoidal reflector (2) to form converging beam (3a)&(3b). Stray light shield (2a) confines rays (3) from halogen lamp to ellipsoidal reflector surface only. Rays (3a)&(3b) converge at second focal point (5a) of ellipsoidal reflector (2). Variable circular aperture (5) is located at second focal point (5a). The circular area of variable aperture (5) may be adjusted for beam intensity control and to limit the field angle of marginal ray (3a). Circular filter (9) is located forward and adjacent to second focal point (5a). The close proximity of (9) to (5a) allows a very small filter diameter to be fully illuminated by diverging beam (3c). Said filter (9) is part of and integral to filter wheel (8). Filter wheel (8) may contain two or more miniature circular filters. The outside diameter of filter wheel (8) is minimized by using small diameters for the circular filters I.e. (9). By virtue of the small diameter of filter wheel (8), the polar moment of inertia is minimized. This allows stepper motor (6) to be greatly reduced in size and torque output. Stepper motor (6) drives filter wheel (8) around its rotational axis (8a) by drive system (7) comprised of spur gears, belt drive or rotor/stator methods. Stepper motor (6) rapidly interchanges filters (9) into beam path (3b & 3a). In one embodiment of the invention, filter wheel (8) may contain a far red/near infrared filter at position (9) with a cut-on frequency of 700 to 750 NM. A clear aperture is present at position (9a). By rapidly interchanging the position of (9) and (9a) the practitioner can interchange far red/infrared and visible spectrum beams. This is advantageous from an examination standpoint in that the pupil (19a) exhibits less contraction response by far red and near infrared spectrum illumination. By then alternating a visible spectrum and infrared filter in rapid sequence, the real image formed at (21) can be alternately a far red/infrared image of subject retina (19) or a visible light image of (19). In a study of test subjects by Levine and Collins, it has been determined that a pulse of visible light not exceeding 10 milliseconds in duration and of sufficient intensity to illuminate the retina for image capture purposes has a minimal effect on pupillary response providing the frequency of visible light pulses is not greater than 1 per 2 to 4 seconds based on individual eye characteristics.

Beam forming optics (10) are conjugate with focal point (5a). Diverging rays (3c) become parallel rays (3c1) upon refraction by (10a). Parallel rays (3c1) are comprised of mixed states of polarization. Parallel rays (3c1) pass through holographic diffuser (11) (which increases beam transmission frequency compared to an ordinary diffuser) creating generally depolarized parallel rays (3c2).

Rays (3c2) pass through the face (22a) of prism (22). Face (22a) may be coated with an anti-reflection coating that improves the coupling efficiency for the wavelengths of operation. Prism face (22b) may be silvered or rely on total internal reflection by virtue of Snell's law to effect a 90 degree light path reflection of rays (3c2). Parallel, depolarized rays (3d) are refracted by second beam forming optic (10b) and are incident upon broad band beam splitter (15) which may have a non-reflective coating applied to its bottom surface to suppress rays 3e. The unpolarized rays (3d) are transmitted as polarized rays (3e) and as reflected polarized rays (3f). Reflected rays (3f) are transmitted through linear polarizer (16) and become linear horizontally polarized rays (3g). Rays (3g) are acted upon by (17)

becoming RHCP rays (3h). Rays (3h) converge at (3i) and illuminate subject retina (19) through pupil (19a). Convergence point (3i) can be shifted axially, I.e. nearer or further from the subject eye by axially varying the position of optic (10a) modifying the conjugate ratio and altering the convergence angle of (3h) which axially alters the convergence point (3i). This is advantageous as the diverging rays passing through subject pupil (19a) can be adjusted to fill the circular area created by the pupil diameter (19a) which may vary by individual eye and ambient illumination present. It should be noted that the states of polarization in FIG. 11 are identical to those in FIG. 8 and can be visualized in FIG. 26A.

Figure 12:
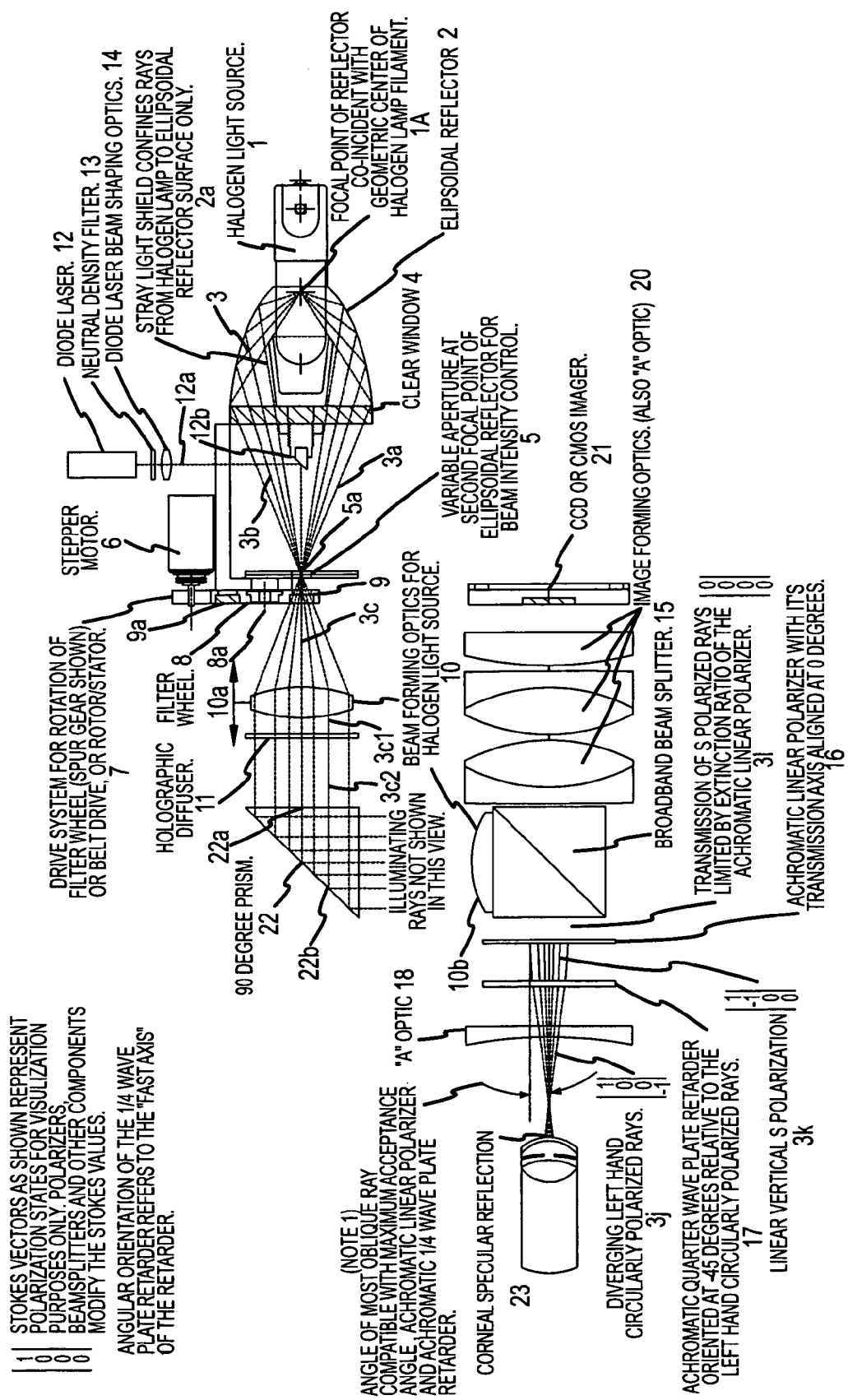
FIG. 12 illustrates an example of extinguishing corneal reflections generated by the polarized light of FIG. 11, in accordance with one embodiment of the present invention.

In FIG. 12, corneal specular reflection (23) creates diverging LHCP rays (3j) which are refracted by (18) acted upon by (17) becoming linearly vertically S Polarized (3k) and are extinguished by polarizer (16). As in FIG. 9 these polarization states can be visualized in FIG. 26B.

Figure 13:
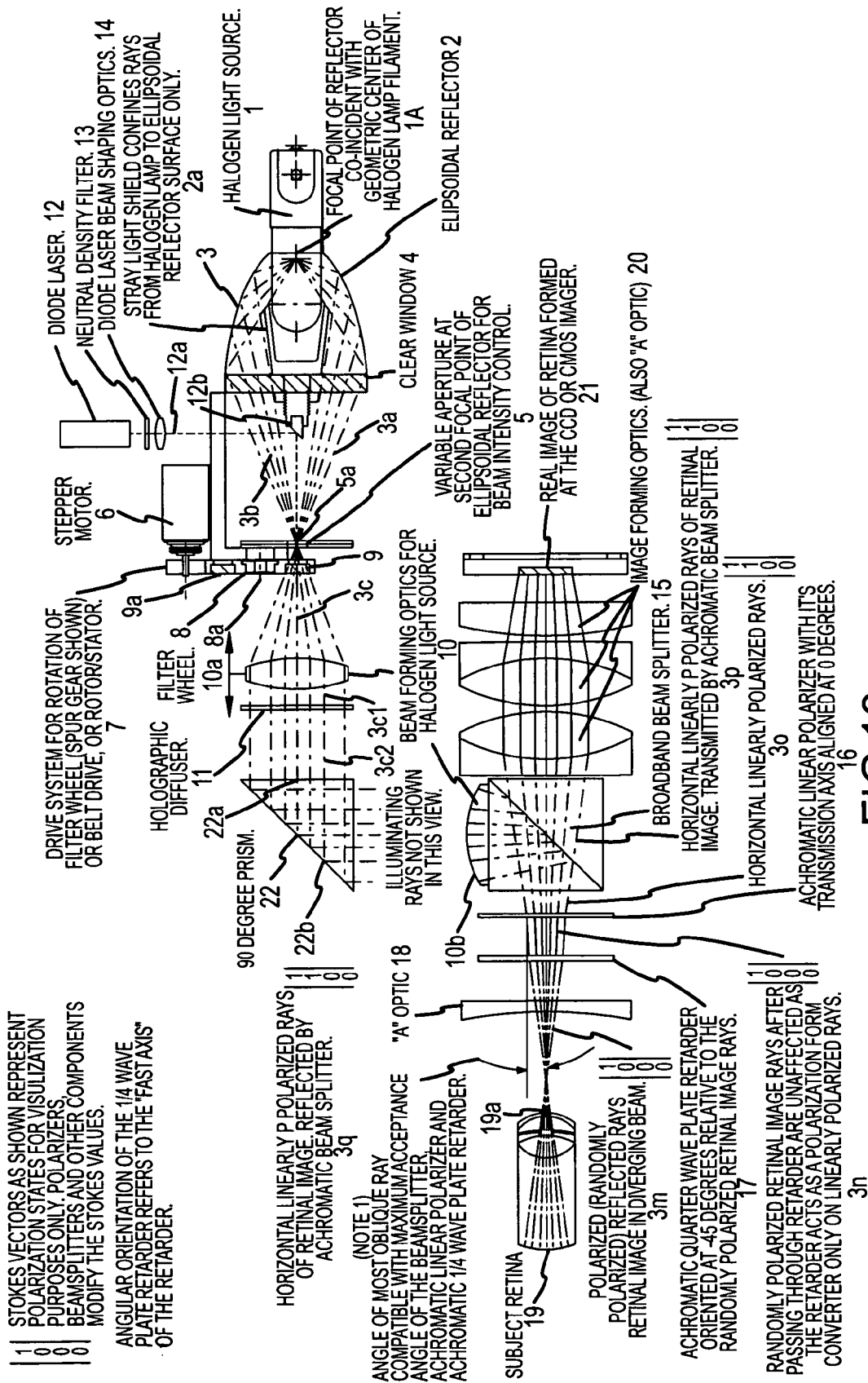
FIG. 13 illustrates an example of transmitting a retinal image to a detector within a hand held device, in accordance with one embodiment of the present invention.

In FIG. 13, the depolarized rays from subject retina (19) are acted upon by the optical and polarizing elements as in FIG. 10. The exception here being the real image of the retina is formed at (21) the CCD or CMOS imager. Direct observation of the real image in infrared examination mode is not possible by direct observation of the examiners eye. As in FIG. 10 visualization of the states of polarization in FIG. 13 are readily apparent by reference to FIG. 26C.

Figure 14:
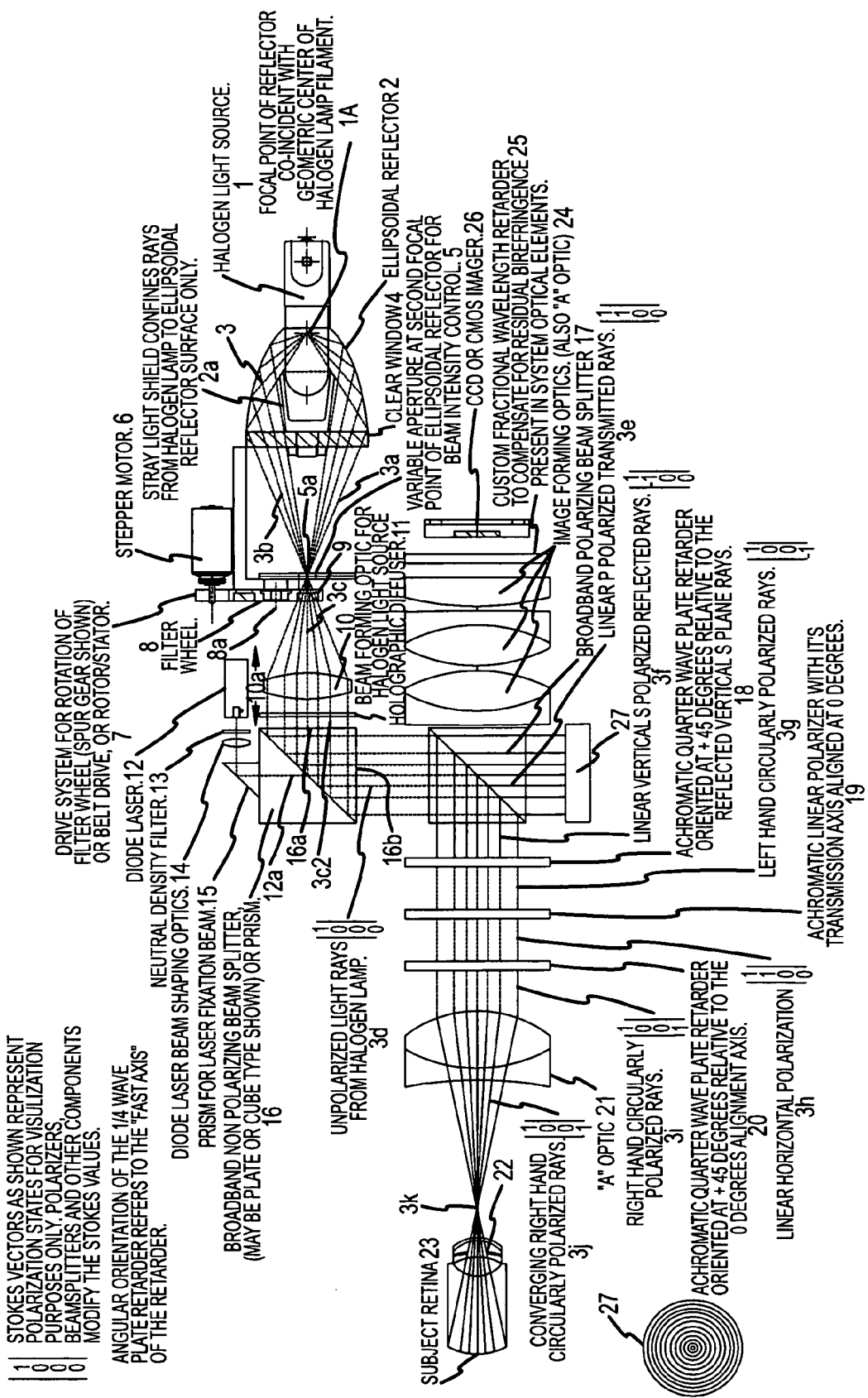
FIG. 14 illustrates another example of a hand held optical device for examining a patient's retina, in accordance with one embodiment of the present invention.

In FIG. 14, a third polarization method is shown having ray path sequence with polarization states. FIG. 14 uses a similar illumination system up to the position identified by holographic diffuser (11). Ray (3c2) enters face (16a) of broad band non-polarizing beam splitter. (16) may also be a 90 degree prism with rod mirror (FIG. 21) or may be a prism as in FIG. 11 as 22. The polarization methods represented provide a means to create a 90 degree change in ray path direction of (3c2) and are contingent on the fixation beam method which will be discussed in a later embodiment. The un-polarized rays (3d) are generally parallel after exiting face (16b). Rays (3d) may deviate from parallelism slightly depending on the conjugate ratio produced by the geometric relationship between beam forming optic (10) and focal point (5a). A small deviation from parallelism is acceptable provided that the angle of the most oblique ray falls within the acceptance angle of (16), (17), (18), (19) & (20). A ray angle of up to +/− several degrees falls within the acceptance angle of the identified components while still providing a greater or lesser angular component to converging RHCP rays (3j) and the associated axial position shift of (3k) which includes the conjugate relationship between optic (10) and optic (21) providing a wider or narrower illumination angle of subject retina (23) based on pupil diameter (22) and the proximity of convergence point (3k) to pupil (22). Therefore, by adjustment of (10) as represented by (10a) the maximum retinal area will be illuminated while operating within the limitations of angular acceptance pertaining to the aforementioned optical and polarizing components. The adjustment may be done manually or automatically, and may be based on signals from the image capture device. The control center of the instrument can also coordinate the beam intensity by adjusting the variable aperture. The prism (15) may also accommodate beams of wavelengths differing from the diode laser (12) shown.

Figure 23:
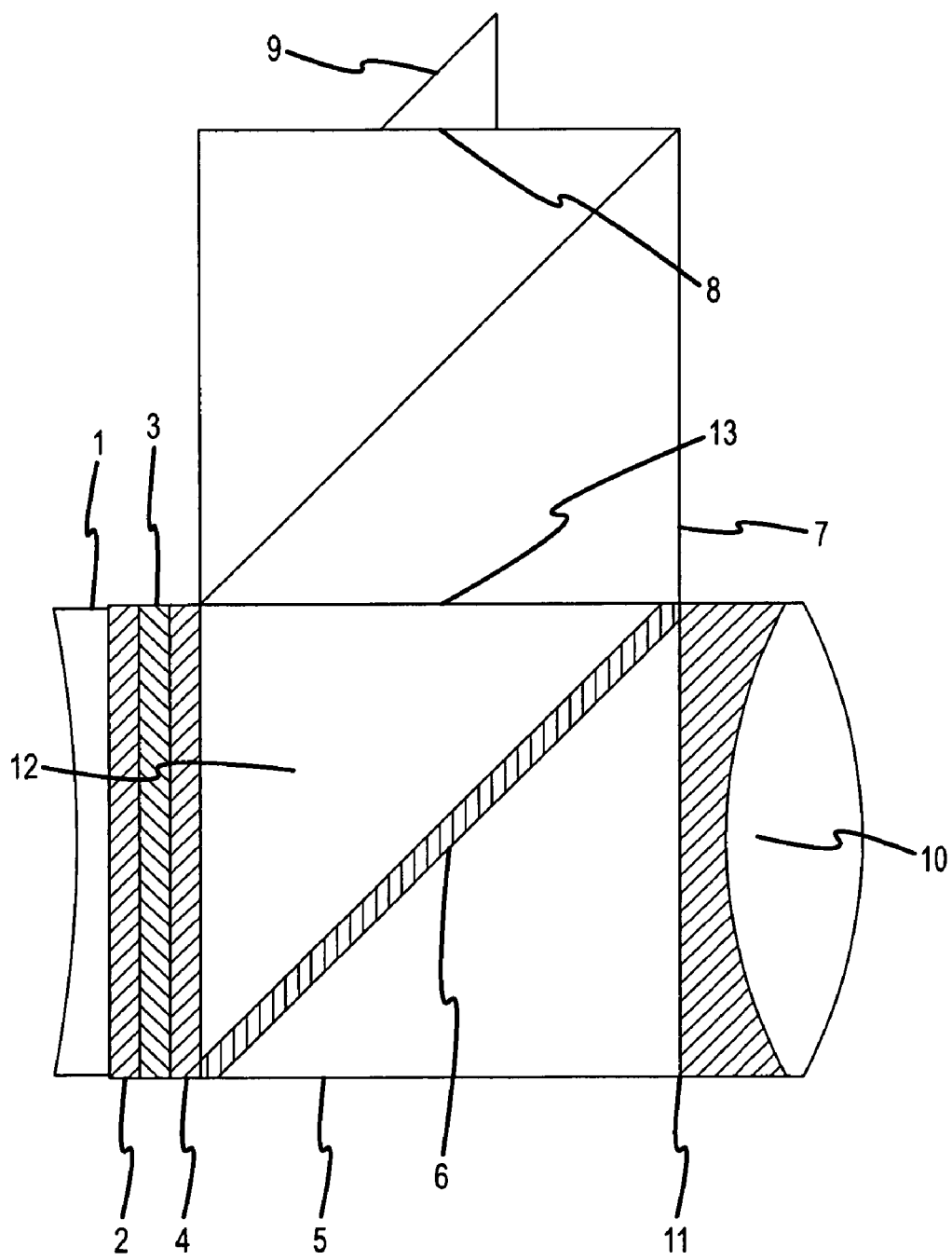
FIG. 23 illustrates an example of optical elements bonded together with optical cement, in accordance with one embodiment of the present invention.
Figure 25A:
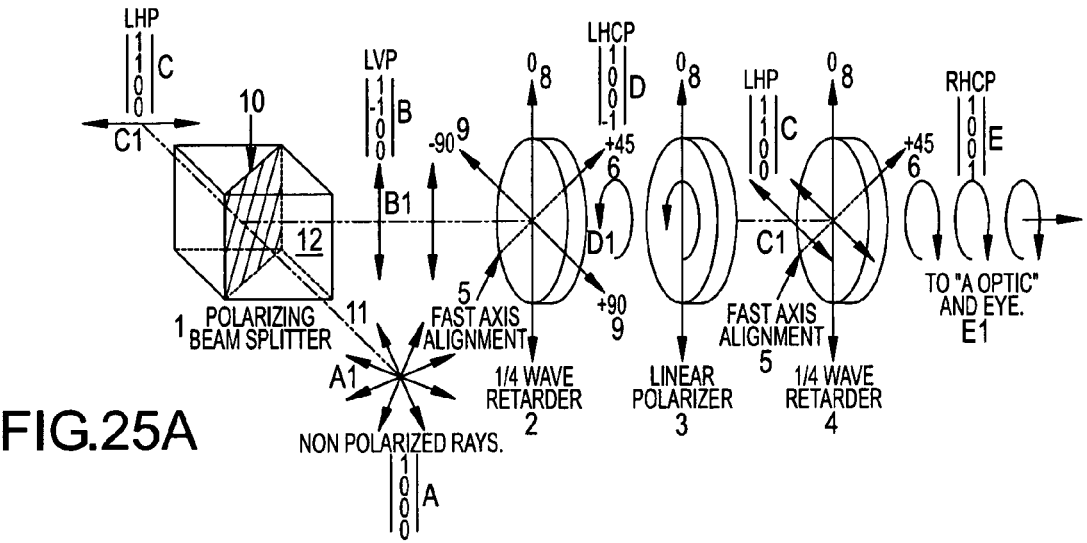
FIGS. 25A-C illustrate an example of various polarization states for the hand held optical device of FIGS. 14-16, in accordance with one embodiment of the present invention.
Figure 25B:
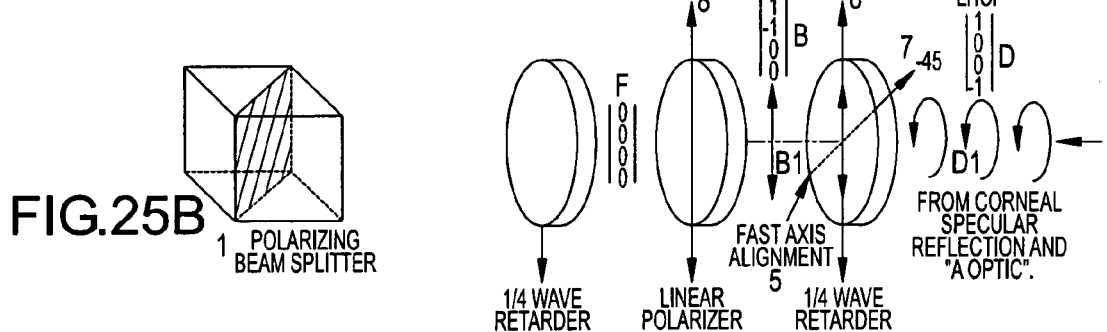
Figure 25C:
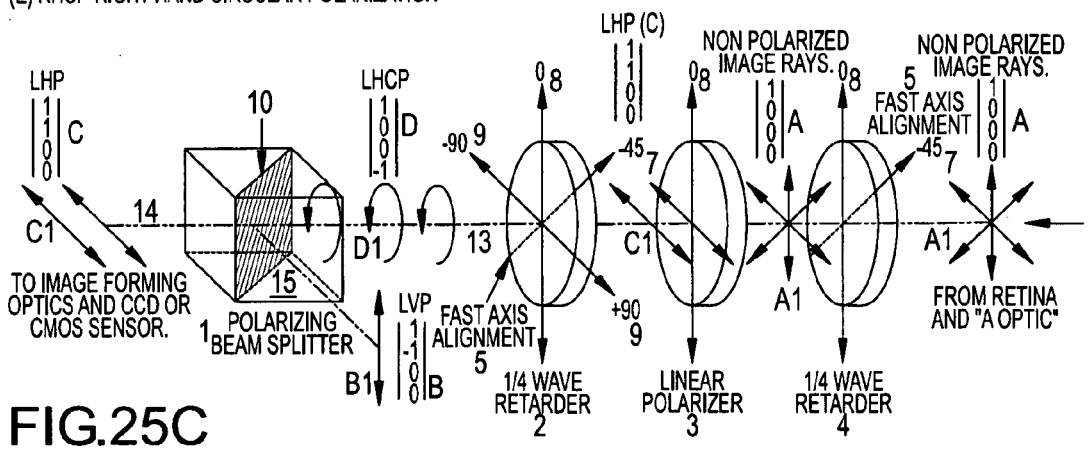

Broad band polarizing beam splitter (17) may be a conventional thin film, cube-type with a quarter wave resonant reflective multi-layer stack, designed for 45 degree incidence (or thereabouts), or as represented in FIG. 23 as 6 may be a wire grid polarizing beam splitter optically bonded between two right angle prisms. The polarization state of rays (3d) and their subsequent passage through (17) can be visualized in FIG. 25A. These un-polarized rays are internally incident on the multi-layer dielectric film of the cube beam splitter shown and are separated into 2 polarized beams with 90 degree deviation (3e&3f). The transmitted rays (3e) become linearly P polarized with the plane of the magnetic field vector parallel to the plane of incidence as represented by FIG. 25A as c1. Rays (3e) are incident on the AR coating (27) greatly reducing return reflection of (3e) back to the optical path or laterally towards the CCD or CMOS sensor (26). A similar coating may be used to reduce reflections from the non-utilized portion of the rays passing through beam splitters in other ray paths and other embodiments. Beam splitter (17) may produce an irradiance ratio of 1:1 that is 50% S polarized and 50% P polarized beams. The reflected rays (3f) are linearly vertically S polarized with the plane of the electric field vector orthogonal to the plane of incidence of the beam splitter. This polarization state can be visualized in FIG. 25A as b1. Rays (3f) are acted upon by achromatic quarter wave retarder (18) and become LHCP rays (3g). Rays (3g) are then transmitted through linear polarizer (19) and become linear horizontally polarized (3h). Rays (3h) are acted upon by a second achromatic retarder and become RHCP rays (3i). The states of polarization and fast axis orientation and polarizer transmission axis orientation can be readily visualized by all of FIG. 25A. RHCP rays (3i) are refracted by optic (21) and become converging RHCP rays (3j) whose most oblique ray angle is dependent on the conjugate relationship between (10), (5a) and (21). This geometric/optical relationship creates the convergence point location (3k) and the subsequent illumination of subject retina (23) through pupil (22) as previously discussed.

Figure 15:
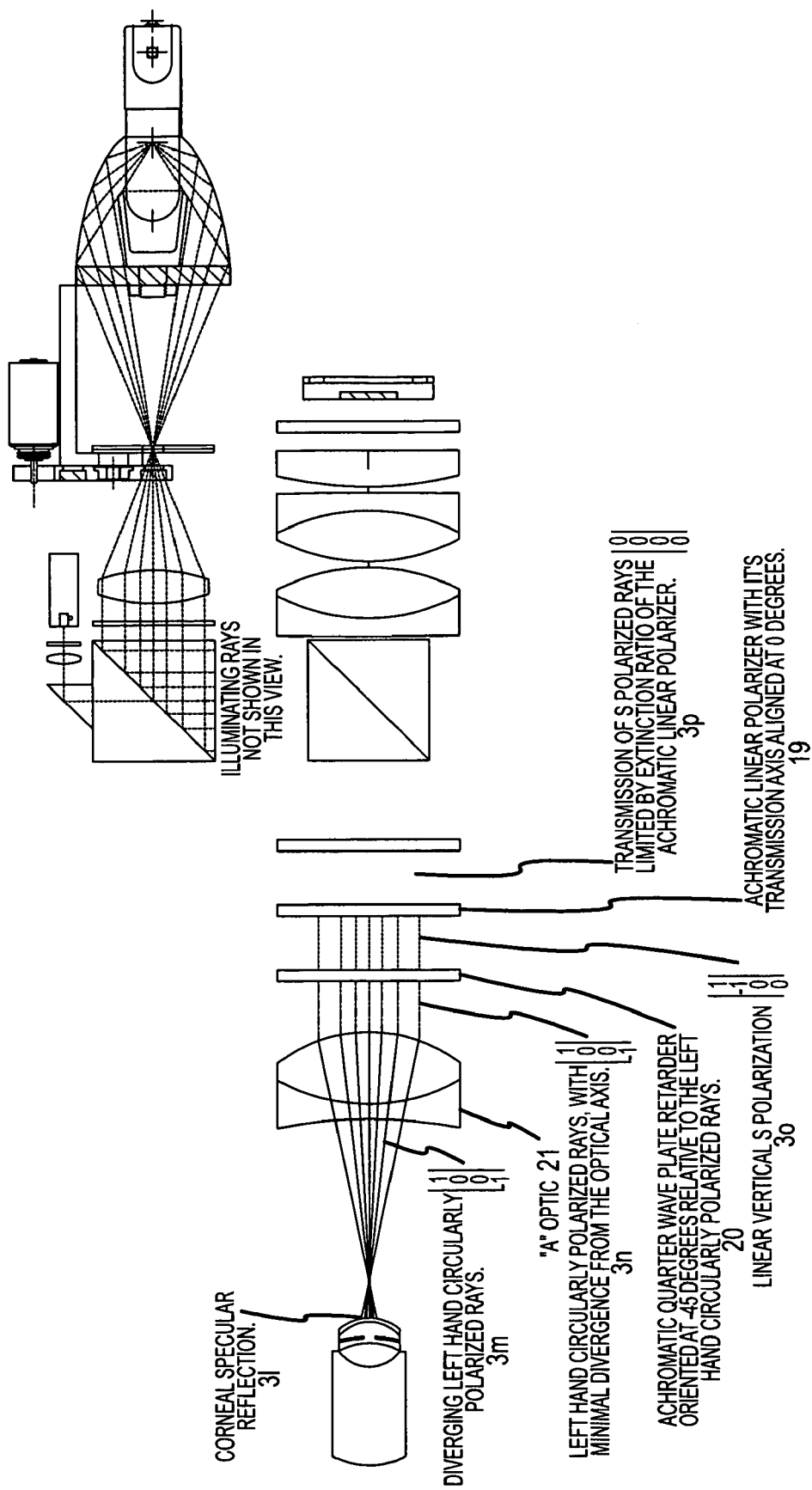
FIG. 15 illustrates an example of extinguishing corneal reflections generated by the polarized light of FIG. 14, in accordance with one embodiment of the present invention.

In FIG. 15, the corneal specular reflection (31) produces diverging LHCP rays (3m) with minimal divergence from the optical axis. Rays (3n) are acted upon by (20) producing linear vertically S Polarized rays (3o) which are extinguished by linear polarizer (19). The states of polarization of (3b) can be readily visualized by (10b) and the final Stokes vector intensity representation of zero as shown in (3p).

Figure 16:
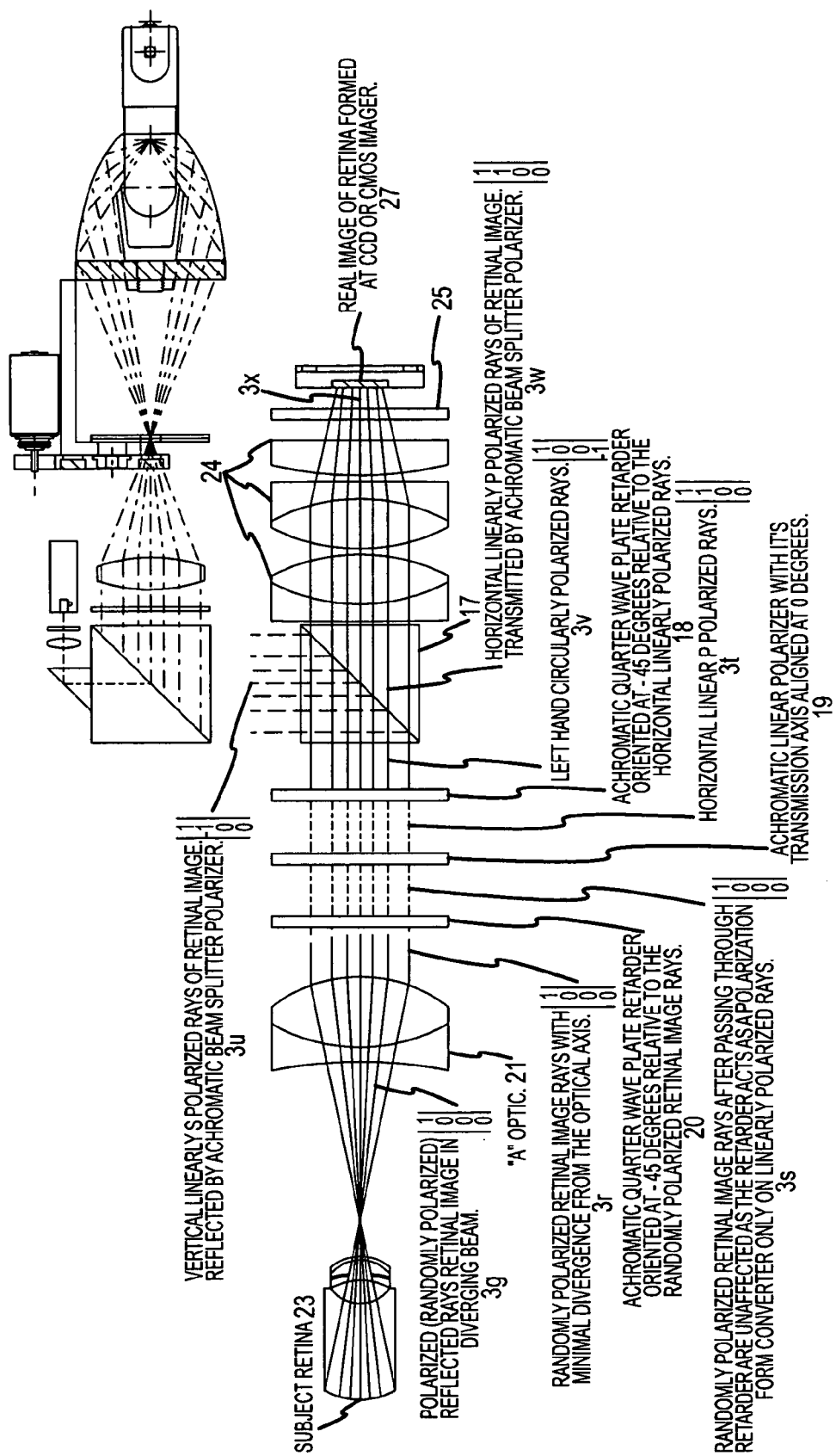
FIG. 16 illustrates an example of passing or transmitting a retinal image to an optical detector, in accordance with one embodiment of the present invention.

In FIG. 16, de-polarized rays (3q) are reflected by subject retina (23) and are image rays, which are refracted by (21) becoming generally parallel rays (3r). Rays (3r) are unaffected by their passage through (20) as (20) does not affect the state of polarization of randomly polarized rays. Rays (3s) are transmitted through polarizer (19) and become horizontal, linear P plane rays (3t). Rays (3t) are acted upon by the second quarter wave retarder (18) and become LHCP rays (3v). Rays (3v) are reflected by (17) and become vertical linear S Polarized rays (3u). Rays (3v) upon transmission through (17) become horizontal, linear P polarized rays (3w). Rays (3w) are refracted by optics (24). The real image of retina (23) may have a modified polarization state differing from (3w) created by birefringence within optics (24) and (17). Polarizing element (25) may be included which is a custom fractional wave plate retarder to compensate for de-polarization effects produced by the aforementioned components. Retinal image rays (3x) represent the corrected polarization state of linear P polarization effected by (25). The real image of retina (23) formed at CCD or CMOS sensor (27) is corrected for both depolarization and optical aberrations by (24) and (25).

FIG. 17 represents the control schema for operation of the various subsystems present within the various embodiments of the invention. A digital signal processor (9) provides control functions for the subsystems. For example, Halogen lamp (25) is controlled through (25a) and its timing function and pulse illumination duration is synchronized to filter position (6), circular aperture (5) and CCD or CMOS detector (1). In one example, switch (13c) is activated, causing (9) to send a control signal to actuate relay (25b), providing continuity of a continuous 6 volt, 2 amp current through (25c) to (25). This also sends a control signal through (11e)to (11a), the stepper motor driver, which sends step pulses through (11c) to (11) causing filter wheel (6) (see FIG. 18) to rotate till optical or magnetic Hall effect sensor (11b) detects the position of magnet or illumination present at(11f) placing infrared filter (6c) in the beam path illuminated through circular aperture (5). It should be noted that the "closed loop" operation of the stepper motors as described throughout this embodiment is advantageous from a "speed of rotational response" standpoint in that the filter wheels do not require a "return to home" function for pulse counting position location and may instead move between filter locations directly reducing the transit time necessary for alternating filters in the respective beam paths. It should be understood that a less sophisticated "open loop" control methodology may also be employed (not shown), that uses "pulse counting" with return to home function.

Figure 33:
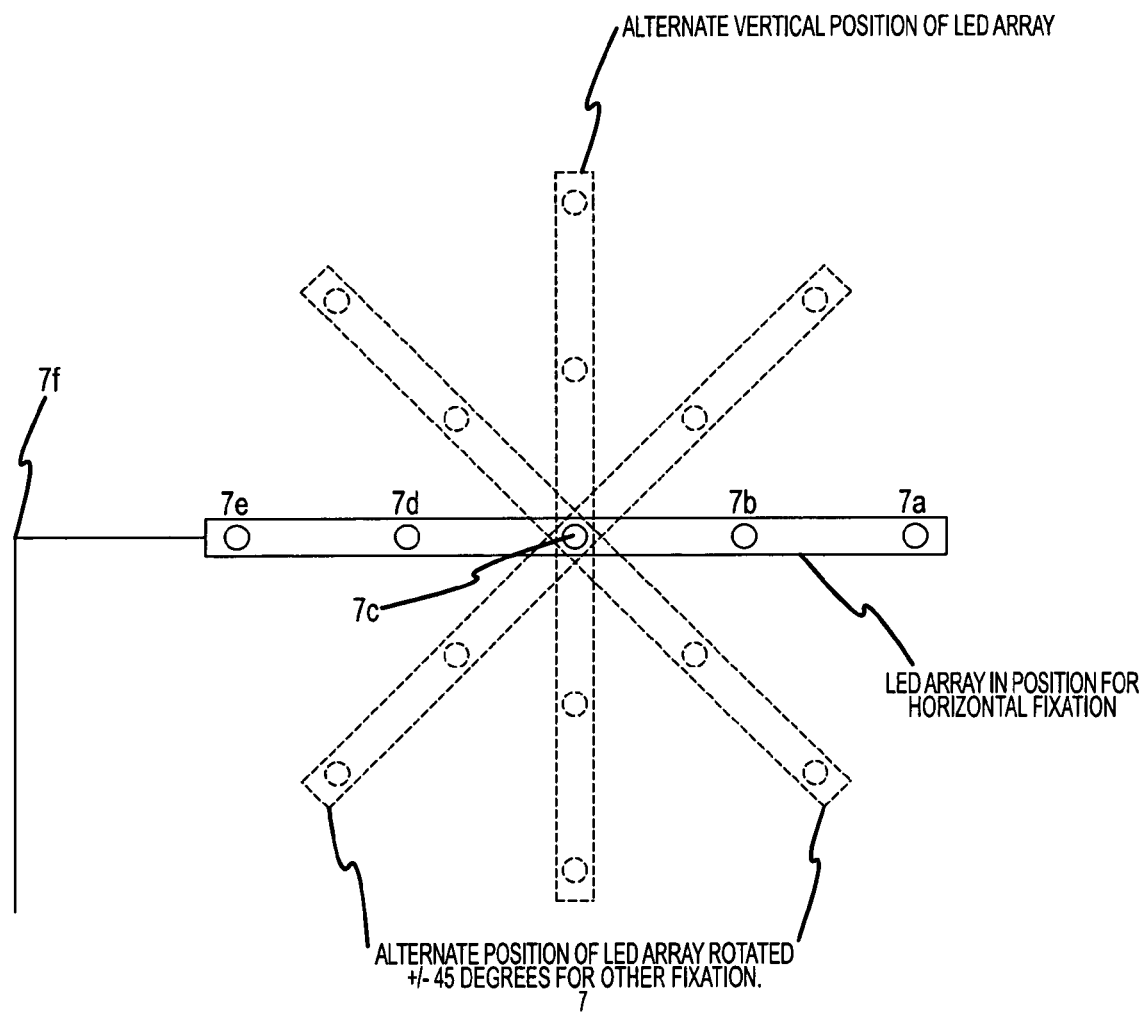
FIG. 33 illustrates an example of various positions of an LED array of FIG. 17, in accordance with one embodiment of the present invention.

The beam intensity may be manually controlled by rotary switch (13d) which sends a specific control signal through (5c) to (5a) causing rotation of (5b) varying aperture (5) dependent on the position of rotary switch (13d). Alternatively, the switch mat be activated in automatic mode, allowing a control signal from the image capture device to vary the aperture, modulating the intensity of the image ray path arriving at the image capture device so as to provide optimum illumination from an exposure standpoint of the image capture device. (5a) may include a tachometer and home position sensor for position tracking and return to home function. Switch (13e) may be manually actuated, sending a low voltage, continuous current through (4a) illuminating diode laser (4) which creates a fixation beam at the discretion of the practitioner/operator. Alternately, rotary switch (f) may be actuated sending control voltage through (7f) to selectively illuminate LED fixation array (7) and the specific illumination of individual diodes (7a) through (7e). LED fixation array may also be manually or automatically rotated to a position 90 degrees (shown) or some intermediate angle (FIG. 16) to allow fixation of the eye in a vertical or diagonal plane, providing a fixation point at numerous locations within the range of rotation of the eye. Multiple peripheral fixation points may also be automatically illuminated to create a virtual central fixation point for patients in whom there is a central scotoma (blind spot) in the contra lateral eye being referenced for fixation. These patients could otherwise not fixate on the array, since they could not see an actual fixation point at the center of their view. FIG. 33 shows details of the operation of (7). Rotary switch (13f) also includes an "automatic" position that will sequentially illuminate diodes (7a) through (7e) which are within the range of rotation of the eye, not under examination. This allows the practitioner to sequentially view and image, if desired, various retinal sections based on the fixation position of the opposite eye, and the angle of view of the instrument. By utilizing the available rotational movement of the eye and the fixation of the eye on the sequential illumination of LED's (7a) through (7e) in combination with rotational control of the array, it is possible to view, capture and catalog a large retinal area through a limited angle of view of the instrument. Images captured in this manner may be combined using an external software package to provide an integrated wide field retinal image.

During examination with infrared light and simultaneous to the positioning of infrared filter (6c) a control signal from (9) is sent through (3e) to stepper motor controller (3a). (3a) sends pulses to stepper motor (3f) and a control signal through (3c) to optical or magnetic sensor (3b) causing filter wheel (3) (shown in FIG. 19) to rotate until infrared correcting optic (3g) is placed central to optical path (18). Correcting lens (3g) may compensate for a shift in the plane of focus of retinal image rays (18) present during infrared illumination.

Rocker switch (13g) may be manually actuated by the practitioner to compensate for diopter correction of the eye under examination by operation of stepper motor (2). If the diopter correction is known prior to the examination the correction can be preset by referring to FIG. 24, the diopter correction pointer (20) from FIG. 27. Automatic setting of diopter correction may also be accomplished by downloading patient data from a PC through signal line (32) to (26), the device "Docking Station" and subsequently from (26) to (9) via (17) or from (26) by encoded radio frequency from antenna (27) to antenna (8a) of RF transceiver (8). Either method produces a control signal through (2d) to stepper motor controller (2a) causing a control signal to be sent through (2g)&(2h) to optical or magnetic sensor set(2b)& (2c) and a series of motor drive pulses through (2i) to stepper motor (2) causing pinion gear (21) to rotate causing carriage (23) to move along rack gear (22) pre-positioning diopter correction optic (20) to the proper correction setting based on the control pulse through (2g) &(2h)and feedback positioning of sensor (2b) in relation to optical or magnetic, position sensing scale (2c). Carriage (23) travel is limited by position switches (2e)&(2f).

The real image of the retina present at (1) is electronically transmitted through signal line (1c) through circuitry (1a), connector (1b) and signal line (1d) to CPU (9). This may be an NTSC analog video image signal or digital image data stream which after processing by (9) and image signal processor (10b) is relayed to (10) LCD electronic display and is presented as a real image on (10a) LCD display screen. Real image (10a) is optically relayed by (10b) creating an image ray path (10c) and is observed by the practitioners eye at (10d) which is the focal point of rays (10c). At any time during the examination the practitioner may actuate switch B, a momentary switch, causing CPU (9) to transmit digital image data to memory card transcriber (12a) causing the individual image to be stored on flash memory card (12) and or transmitted by antenna (8a) to the receiver of (26), by antenna (27), which relays the image data to a PC for drive storage by signal line (30). The PC may have a software program that creates an image of the retina that is comprised of smaller individual retinal images that are joined or "stitched" to form a continuous and seamless larger image comprising a greater angular section of the retina. The combination of hardware and software in this instance provides great utility in providing a means for the practitioner to capture a series of narrow angle images by having the patient fixate on the LED array in a sequential fashion. The individual images may then be combined to form a larger image for documentation or study by a retinal specialist.

By actuating switch A, also a momentary switch, a full spectrum visible light image of the retina may be captured as follows: CPU (9) sends a control signal through (11e) to (11a) which sends pulse and control signals through (11c) and (11d) causing (11) to rotate (6) to filter position (6a) which is a no filter position (clear aperture) on (6). The full spectrum, visible light rays created by (25) pass through the optics to the subject retina and are reflected as an image ray path as shown by (18) and previously described and shown in FIGS. 8-16. Simultaneous to the positioning of (6) a control signal is sent through (3e) to (3a) creating pulse and control signals through (3d) and (3c) to (3f) and (3b). This causes (3f) to rotate (3), placing filter (3h) centrally positioned in ray path (18). Filter (3h) is an IR cut filter limiting the image spectrum present at (1) to visible light only, blocking near IR rays thereby improving image detail. The rotation of (6) and (3) occur rapidly, transitioning between infrared light present for examination and visible light for the retinal image.

Figure 27:
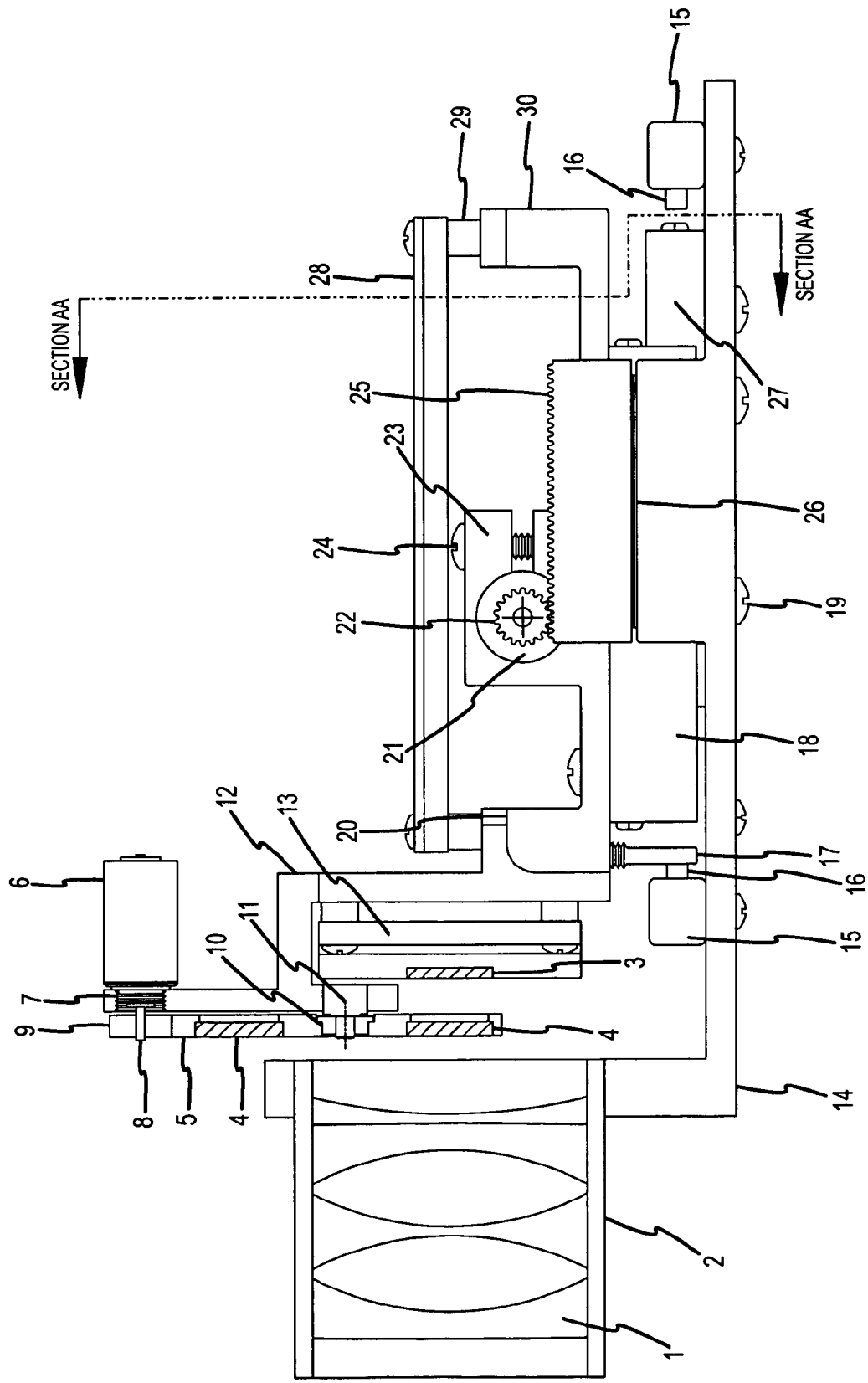
FIG. 27 illustrates an example of a hand held device having a selectable filtering element, in accordance with one embodiment of the present invention.

Beams of other wavelengths may also be incorporated as described in FIG. 14. In this case, the filter wheels would position other filter positions shown in FIGS. 18, 19 to facilitate dye studies of the retina using for example Indocyanine green dye and/or fluorescein dye, and then alternately exciting the dye(s) with the appropriate excitation wavelengths by rapidly positioning filters shown in (3) and (6). Optimal filters for the reception wavelengths of the excited dye(s) can be similarly placed in the image path as illustrated in FIGS. 17, 27.

The total time of filter wheel transit between IR, visible light and return to IR is 100 milliseconds or less. The visible light image is also stored on (12) as per the method previously mentioned. The IR or visible light image may alternatively be transmitted by (8) to the docking station (26) receiver or through RF cable (19) to an external monitor or through cable (16) to (26) and subsequently through (30) of (26) to an external PC. Cable (30) may be a "firewire" or other high speed interface.

In one example, block 26 is the power supply and can be in the form of a rechargeable battery for a compact, hand-held device that is entirely autonomous or an AC to DC converter for powering from an AC mains electrical supply. Connector (28) of (26) provides a means of electrical and signal interconnection between the hand held device and (26), including battery charger connection (14a) of (26) which provides "intelligent" battery charge control of the onboard battery pack of the hand-held instrument. Connection 15 is for external programming of the EPROM on CPU (9) through connection (31) of (26). Signal lines (33) & (34) are for future system expansion. The hand held device described by the embodiments may be designed to drop-in to the Docking Station (26) when recharging or data transfer functions are necessary. (26) is powered by connection (29) to an AC mains power source, typically 120 VAC @ 60 HZ in the United States. Signal lines (16) and (17) are for future system expansion.

Figure 20:
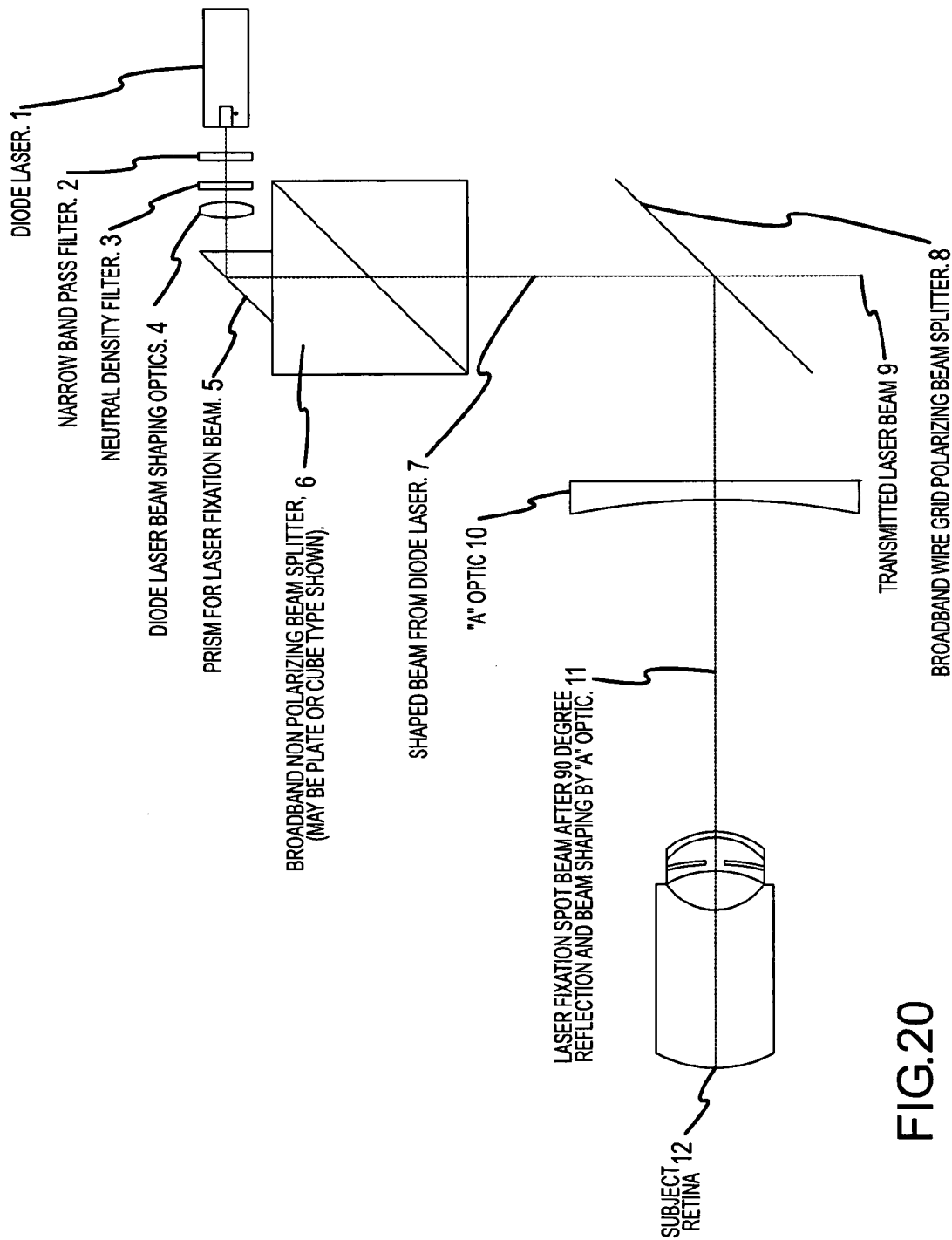
FIG. 20 illustrates a method for creating a fixation spot within the hand held device for a patient to look at during an eye examination, in accordance with one embodiment of the present invention.

In FIG. 20, a method for spot fixation is shown. Diode laser (1) utilizes a laser frequency in the far red band width and is of a very low power 1 miliwatt class. The narrow Gaussian beam produced by (1) may be limited in its spectral band width by narrow band pass filter (2). The laser frequency is based on its visibility by the eye and by the transmission curve of the aforementioned infrared filter whose half power band width is centered slightly past the visible spectrum providing transmission of frequencies in the far red spectrum I.e. the diode laser frequency. The beam may be further reduced in intensity by passing through ND filter (3). The beam may be shaped by optic (4) before entrance to prism (5). Prism (5) effects a 90 degree beam path change for passage through broad band, non-polarizing beam splitter (6). The beam emerges from (6) as shaped beam (7) and is coincident with the illumination rays not shown in this diagram. Beam (7) is further reflected at 90 degrees from wire grid polarizer (9) and is refracted by A optic which is conjugate with (4) creating a focused shaped beam (11) which is incident upon subject retina (12). It should be noted that the combination of a very low power laser diode, neutral density filter and the beam passage through two beam splitters sufficiently reduces the laser beam intensity rendering it completely "eye safe".

Figure 21:
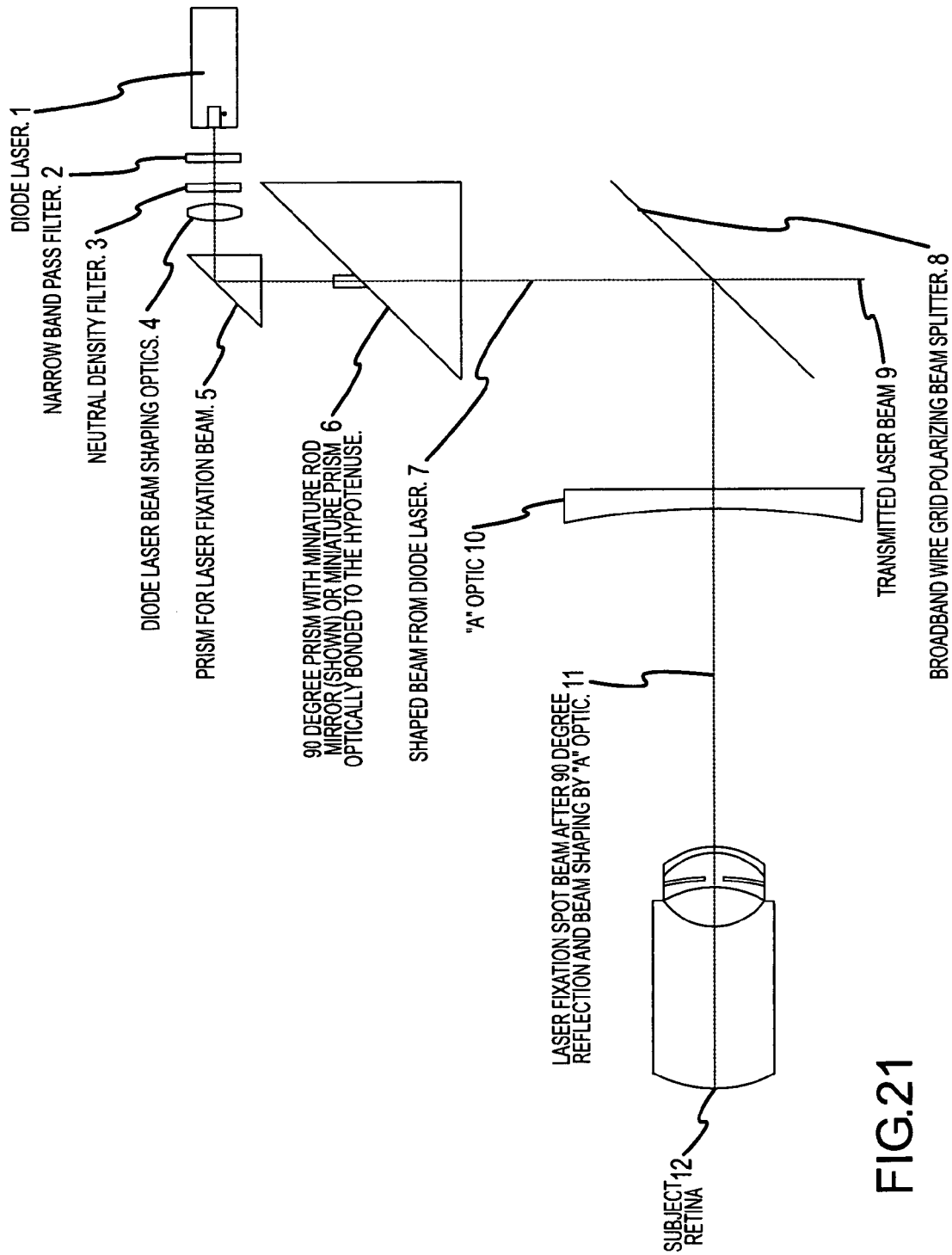
FIG. 21 illustrates another method for creating a fixation spot within a hand held device, in accordance with one embodiment of the present invention.

In FIG. 21, another spot fixation method may be implemented. As in FIG. 20, a diode laser (1), band pass filter (2), ND filter (3) and prism (5) are present with a similar embodiment. After passage through prism (5) with subsequent 90 degree beam rotation the beam enters the non-reflective, thin film coated face of a miniature rod mirror. This miniature rod mirror (with non-aluminized 45 degree surface) or prism is optically bonded to the geometric center of the 90 degree prism. The laser beam passes through the 90 degree prism due to the optical coupling between the rod mirror and hypotenuse face. The shaped laser beam (7) then reflects from (8) and is incident upon (12) in a fashion similar to FIG. 20.

Figure 22:
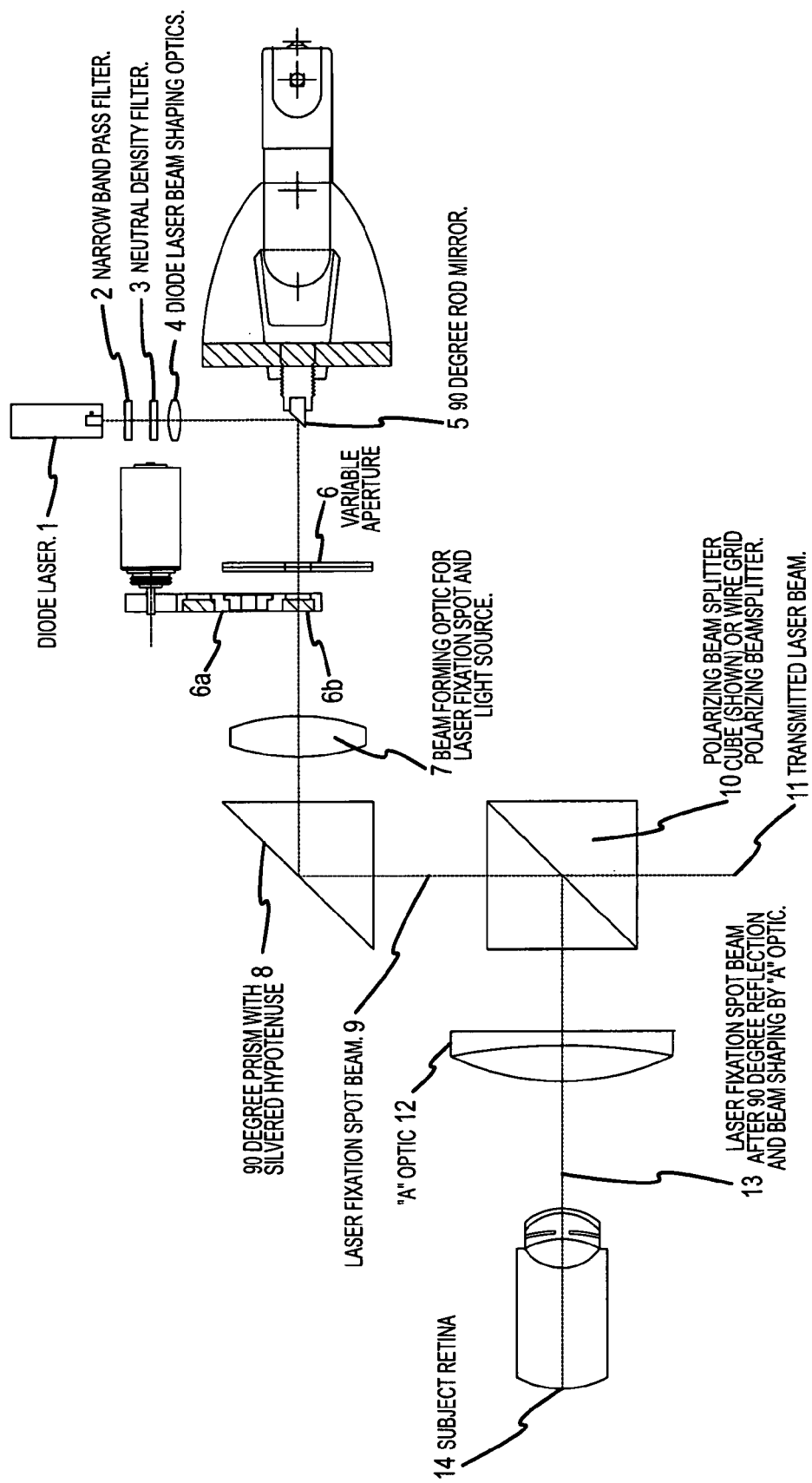
FIG. 22 illustrates another method for creating a fixation spot within a hand held device, in accordance with one embodiment of the present invention.

In FIG. 22, another spot fixation method is shown. Diode laser (1) through component (4) are similar to the two previous embodiments. The laser beam is reflected at 90 degrees by rod mirror (5) and is coaxial with the illuminating beam (not shown). The beam then transits through clear aperture (6) and filter (6b) where it is further shaped by optic (7) which is a dual purpose optic also refracting the illuminating beam. The shaped Gaussian beam is then reflected at 90 degrees from the silvered hypotenuse face of (8) and subsequently transit's the other components shown arriving at subject retina (14) in a manner similar to FIGS. 20-21.

In FIG. 23, optic (1) is bonded to retarder (2) using an index matching clear optical cement. (2) is further bonded to polarizer (3) in the same fashion which is also bonded to (4), the second retarder in a similar fashion which is then bonded to face of prism (12) in a like manner. The hypotenuse of prism (5) is optically bonded to wire grid polarizer (6) which in turn is bonded to the hypotenuse of prism (12) from the aforementioned bonded assembly. The faces of prism (12) and beam splitter (7) are optically bonded as are the faces of prism (9) and the geometric center of beam splitter (7) at point (8). Optic (10) may possess a planar surface (11) which is then bonded to the face of prism (5). Producing an assembly in such a manner creates a mechanically and optically integrated system which is highly advantageous from a stand point of mechanical ruggedness and efficiency of optical coupling by virtue of the reduction of intervening glass air interfaces. It should further be emphasized that a higher degree of optical precision can be achieved in such a manner by the reduction of mechanical mounting components and their introduction of cumulative tolerance error.

As to FIGS. 25A-C and 26A-C, the states of polarization which have been discussed in some embodiments above can be visualized by reference to these FIGS. 25A-C, 26A-C. All of the Stoke's vectors shown represent idealized states of polarization. The Mueller calculus to derive the states of polarization includes mathematics which represent altered states of polarization incurred by certain polarization components. These modified states of polarization are not included in FIGS. 25A-C, 26A-C in order to clarify polarization effects created by the various components present.

Figure 24:
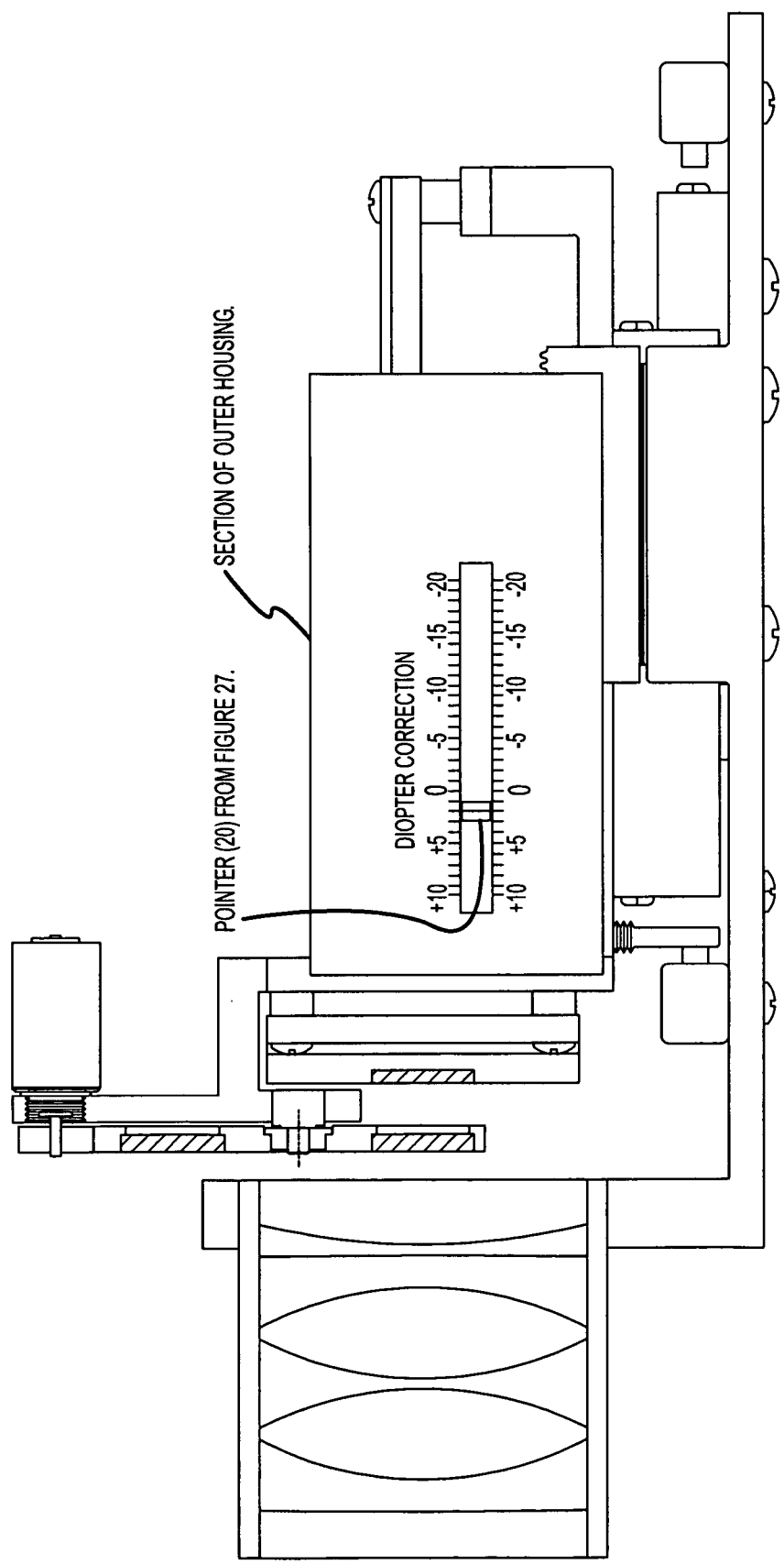
FIG. 24 illustrates an example of a hand held device having a diopter correction scale, in accordance with one embodiment of the present invention.
Figure 28:
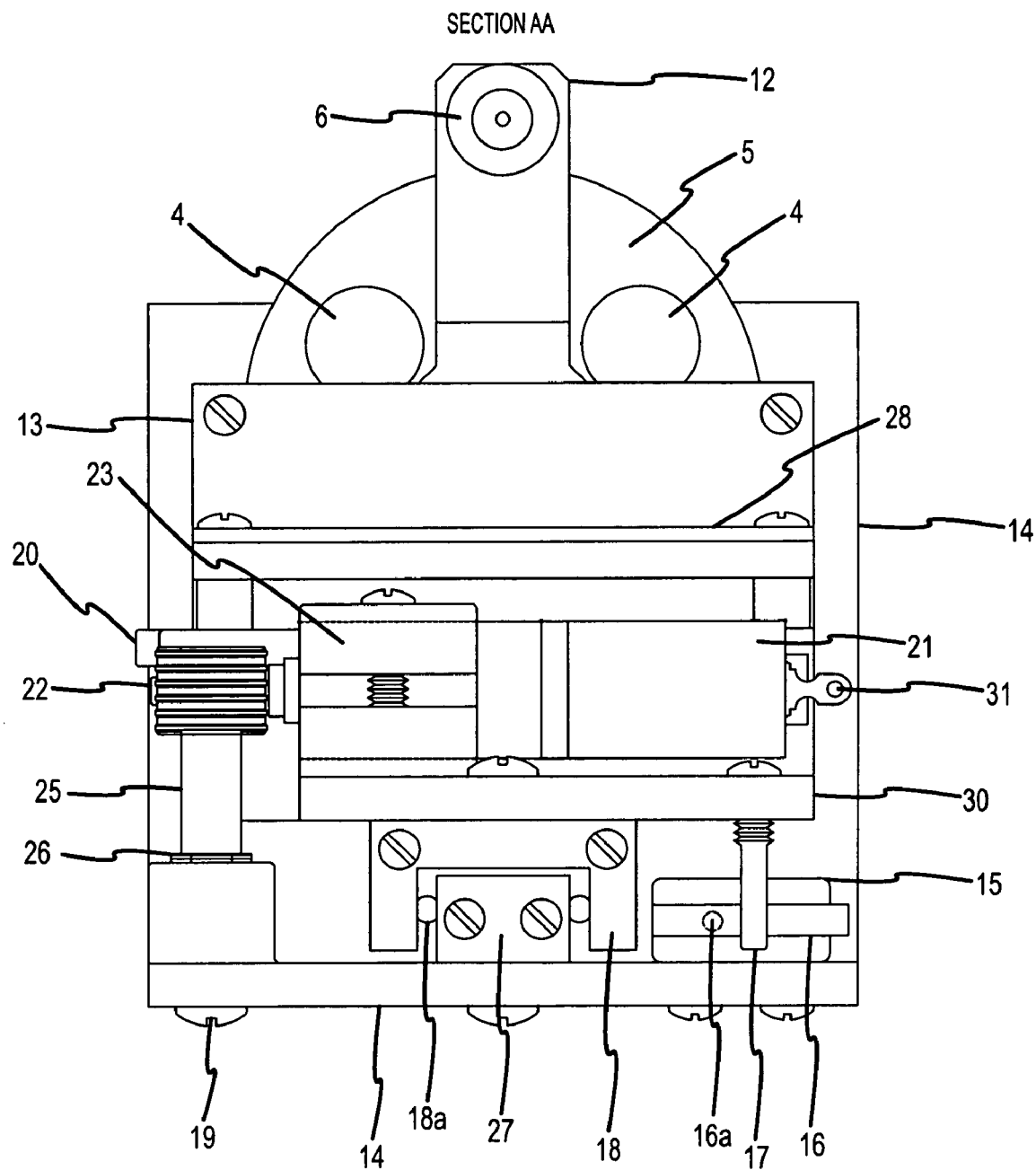
FIG. 28 is a sectional view taken along section lines AA-AA of FIG. 27, in accordance with one embodiment of the present invention.

In FIG. 27, optics (1) are incorporated into housing (2) and present a real image through filter (4) to CCD or CMOS detector (3). A filter wheel (5), analogous to the one previously discussed in the illuminating path, is rotated by spur gear (9) around shaft (8) by stepper motor (6) fixed to mounting (12) by thread (7). Filter wheel (5) rotates around ball bearing (10) fixed to mounting (12) by shaft adaptor (11). (3) is attached to mounting (12) through carrier (13). Stepper motor (21) is clamped to carrier assembly (30) by split coupling (23) and clamping screw (24). By rotation of spur gear (20) carrier assembly (30) is caused to move along rack gear (25). This movement is controlled in a linear fashion by ball slide assembly (27) and (18). Carrier assembly (30) also retains circuit board (28) and diopter pointer (20). Ball slide base (27) is fixed to mounting housing (14) by screws along the base of (14), typically identified by (19). Slide (18) moves in a precision manner along (27) controlled by balls (18) (not shown in this view). The limits of travel of carrier assembly (30) are fixed by stop pin (17) which contacts limit switch actuator (16) tripping limit switch (15), interrupting travel of (30). A second stop pin which is not seen in this view limit's the travel of (30) in the opposite direction by actuating limit switch (15) located on the right hand side of this view. Linear movement of (3) through the aforementioned assembly is necessary for diopter correction adjustment as shown in FIG. 24. In FIG. 28, section AA is shown.

Figure 29:
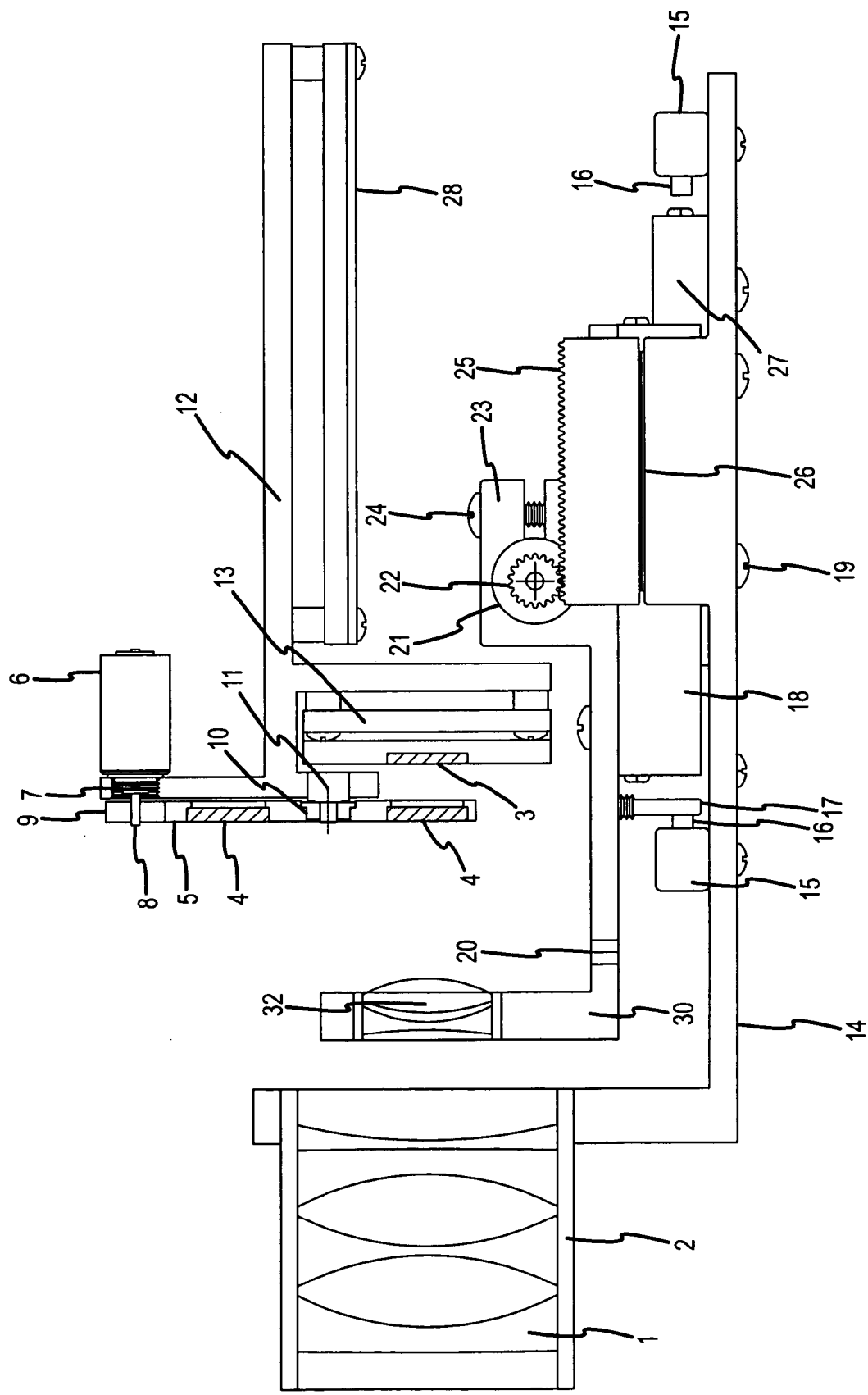
FIG. 29 illustrates another example of a hand held device having a mechanically moving optic, in accordance with one embodiment of the present invention.

In FIG. 29, this embodiment utilizes many of the components previously described in FIGS. 27-28. However, in this case CCD CMOS detector (3), filter wheel assembly (5) and mounting (12) remain stationary. Carrier assembly (30) moves correcting optic (32) in a linear fashion. The limits of travel, ball slide assembly, stepper motor and mounting and diopter position indicator function in a manner similar to that previously described in FIG. 27.

Figure 30:
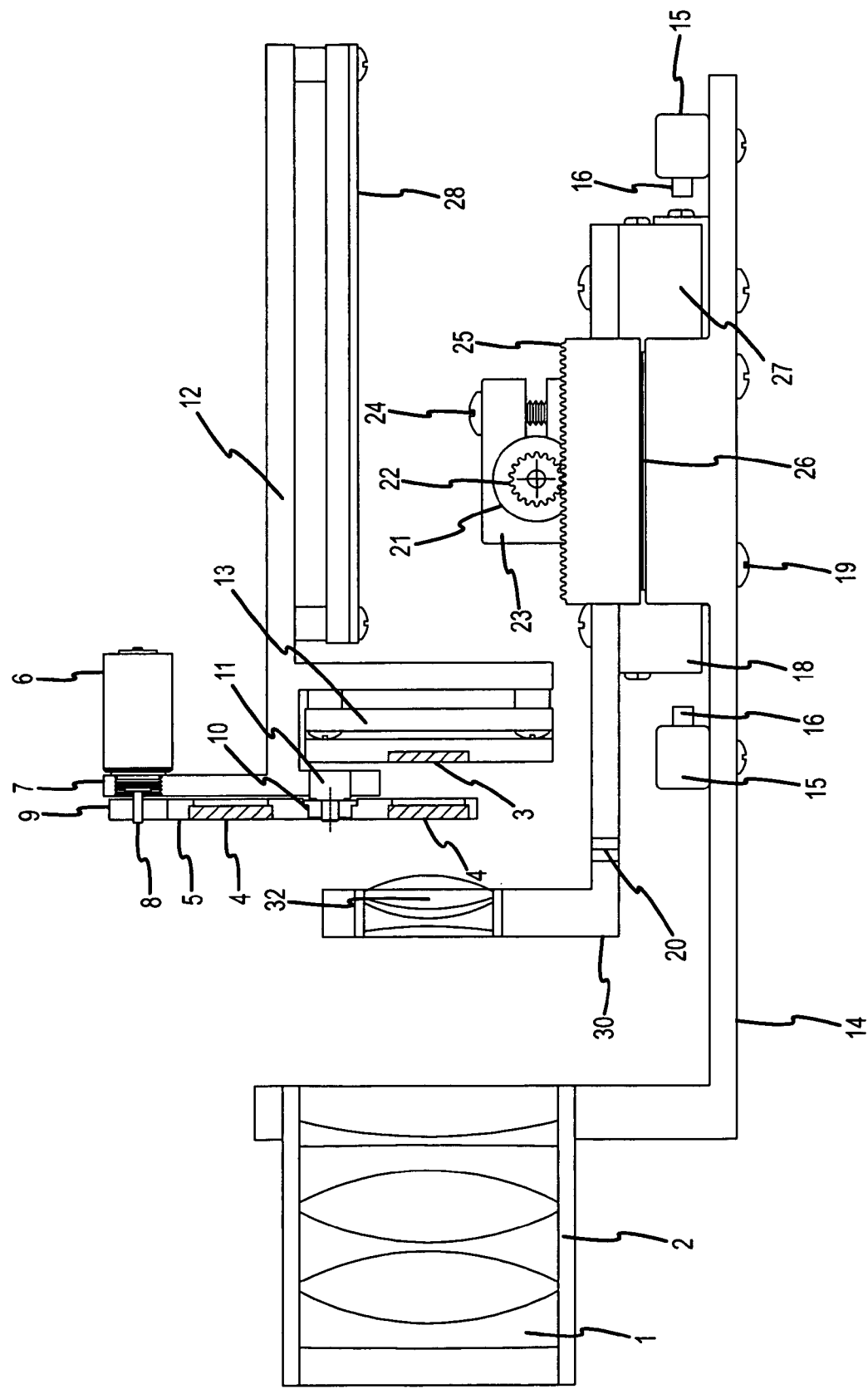
FIG. 30 illustrates the optical device of FIG. 29, wherein a portion of the lenses has been linearly moved, in accordance with one embodiment of the present invention.
Figures 31, 32:
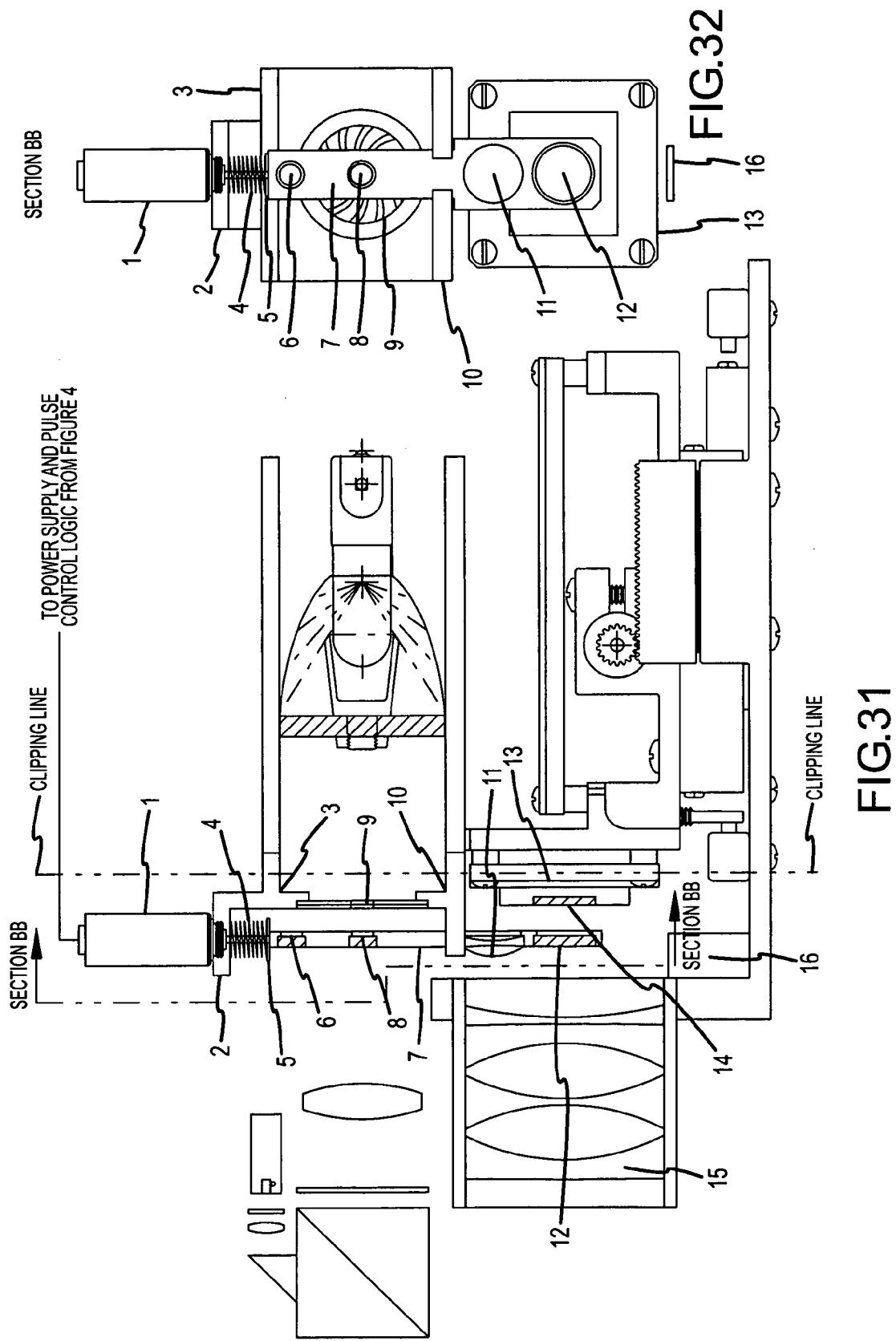
FIG. 31 illustrates another example of a hand held device having a solenoid controlling the position of a two position, dual element filter, in accordance with one embodiment of the present invention.
FIG. 32 illustrates a sectional view of FIG. 31 taken along section lines BB-BB, in accordance with one embodiment of the present invention.

In FIG. 30, this figure represents the motion of carrier assembly (30) and the alternate positioning of optic (32). In FIG. 31, this embodiment illustrates a simplified instrument using an electromagnetic actuator (1) to move filter and optic assembly (7) in a linear manner. This is useful for an instrument to shift between IR examination mode and visible light mode. As shown in both views electromagnetic actuator (1) is in its actuated position, pulling in spring (4) and spring plate (5) which are fixed to carrier assembly (7). In this actuated position, clear aperture (8) is located to allow visible light illumination to pass through (8) and (9), illuminating the retina as previously illustrated and returning through optics (15) and passing through IR cut filter (12) to create a real image at (14). When (1) is de-energized, coil spring (4) forces carrier (7) to move to its opposite limit of travel at stop (16) (not shown). This linear motion places IR filter (6) in the illuminating beam path and IR correction optic (11) in the image path, correcting for the infrared focal plane shift. The practitioner can alternate between the two states of illumination to either view the subject retina in infrared light or capture images in visible light. The transition between the two states of illumination is controlled by applying a pulse current to (1) of sufficient duration to cause carrier (7) to change position rapidly allowing alternate visible light and IR illumination to occur within the response time limitations imposed by the response of the pupil to the brief, visible light pulse necessary for image capture.

Figure 35:
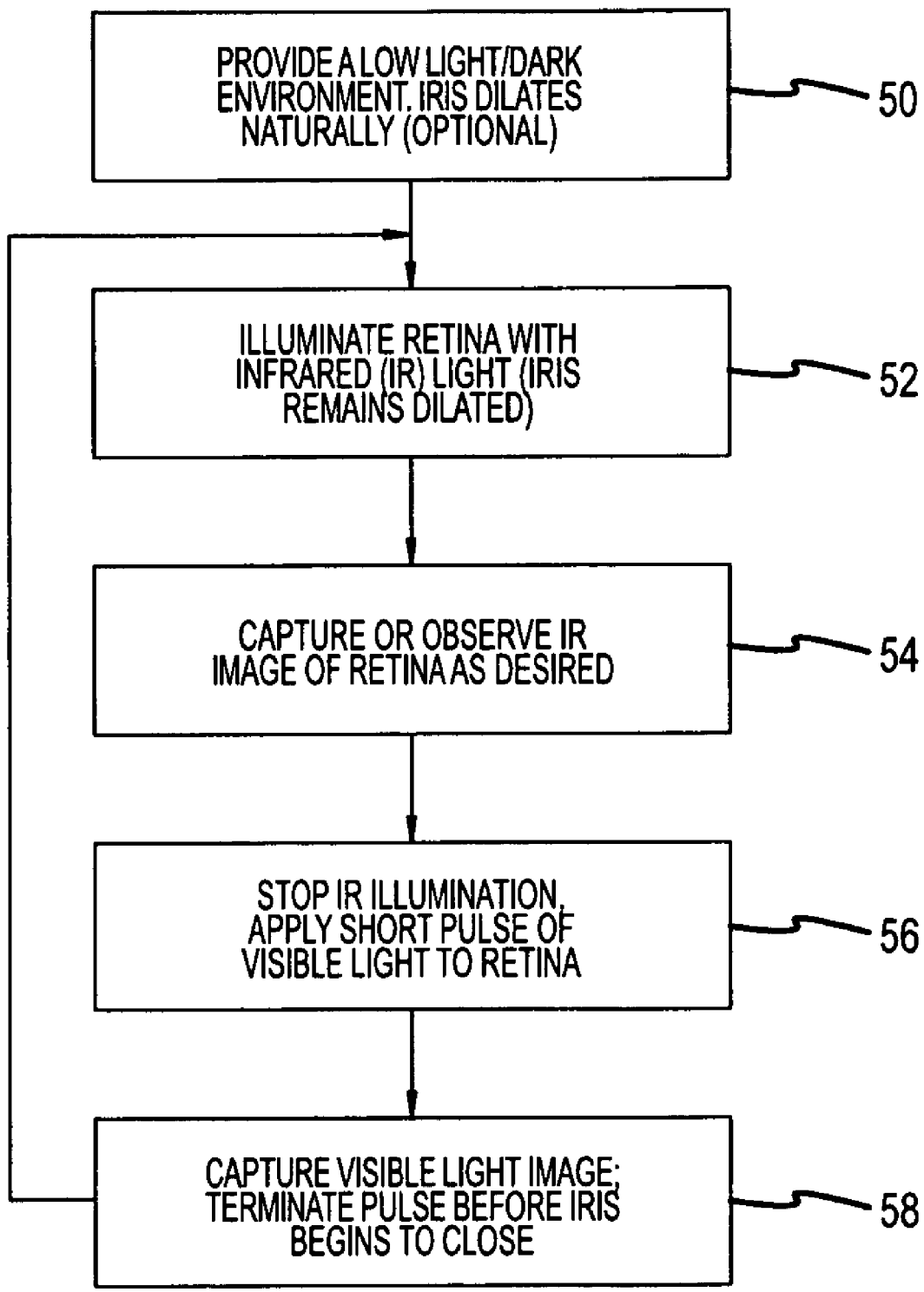
FIG. 35 illustrates an example of logical operations for imaging a retina, in accordance with one embodiment of the present invention.

Referring to FIG. 35, a method for imaging the retina is shown in accordance with one embodiment of the present invention. At operation 50 (which is optional), a low light or dark environment may be provided for performing the eye examination. Such a low light/dark environment has the tendency to open the patient's iris widely. At operation 52, infrared light is applied to the patient's pupil. It has been found that the human iris is generally non-responsive to infrared light, and accordingly, operation 52 does not generally affect the degree to which the patient's iris is opened. At operation 54, an infrared image of the retina is captured. In one example, operation 54 captures the infrared image of the retina using a CCD or CMOS sensor capable of capturing an infrared image, and the image may be a black and visible image. The infrared light of operation 52 may be continually applied and various images of the retina may be obtained by operation 54. In one example, a digital display is provided so that the eye doctor may view various images in real-time of the patient's retina.

At operation (56), a short pulse of visible light may be applied to the patient's pupil, preferably, after the infrared light of operation (52) has been removed from the patient's pupil. The short pulse of visible light is of a time period short enough such that the patient's iris does not begin to close in reaction to the visible light. In one example, the short pulse of visible light is preferably 10 milliseconds or less. During the visible light pulse, operation (58) captures a color image of the retina. Operations (52), (54), (56) and (58) can be repeated as much as desired to obtain as many images (IR images or visible light images) of the retina as needed for the particular eye examination.

Hence, in this manner, the retina can be examined and imaged without the use of mydriatic eye drops. Further, the images can be digitally stored or manipulated in a computer system, and may be associated with a patient's file or electronically transferred or shared by various eye doctors.

Figure 36:
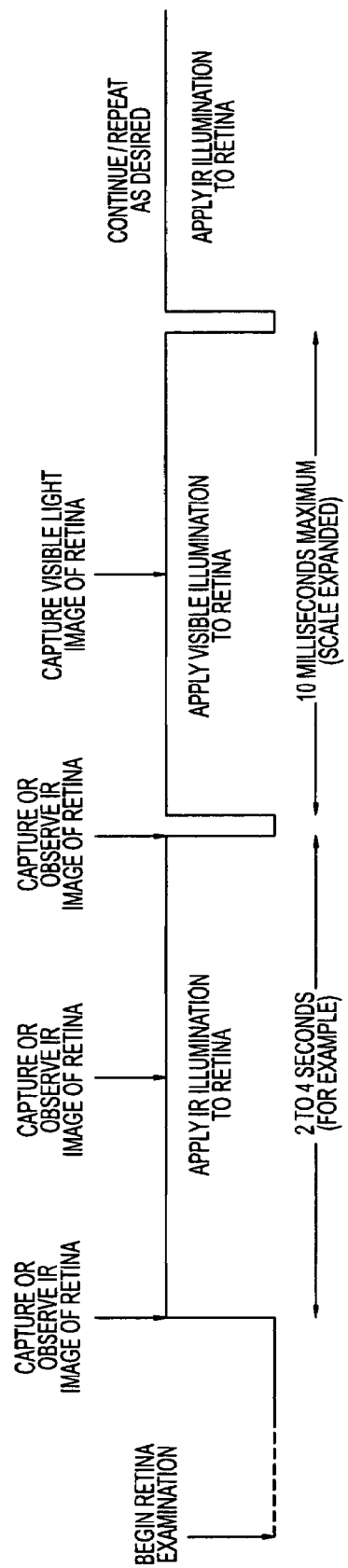
FIG. 36 illustrates an example of a timing diagram for imaging a retina, in accordance with one embodiment of the present invention.

FIG. 36 illustrates a timing diagram in accordance with one embodiment of the present invention. Upon beginning the eye examination, infrared light is applied to the pupil and one or more infrared images of the retina may be obtained. In one example, the infrared light is removed from the pupil, and a visible light pulse is applied to the pupil, the visible light pulse being preferably 10 milliseconds or less. During this visible light pulse, one or more images of the retina may be obtained. After the visible light pulse has terminated, infrared light may be applied to the pupil for additional examination and imaging of the retina, as desired.

Figure 37:
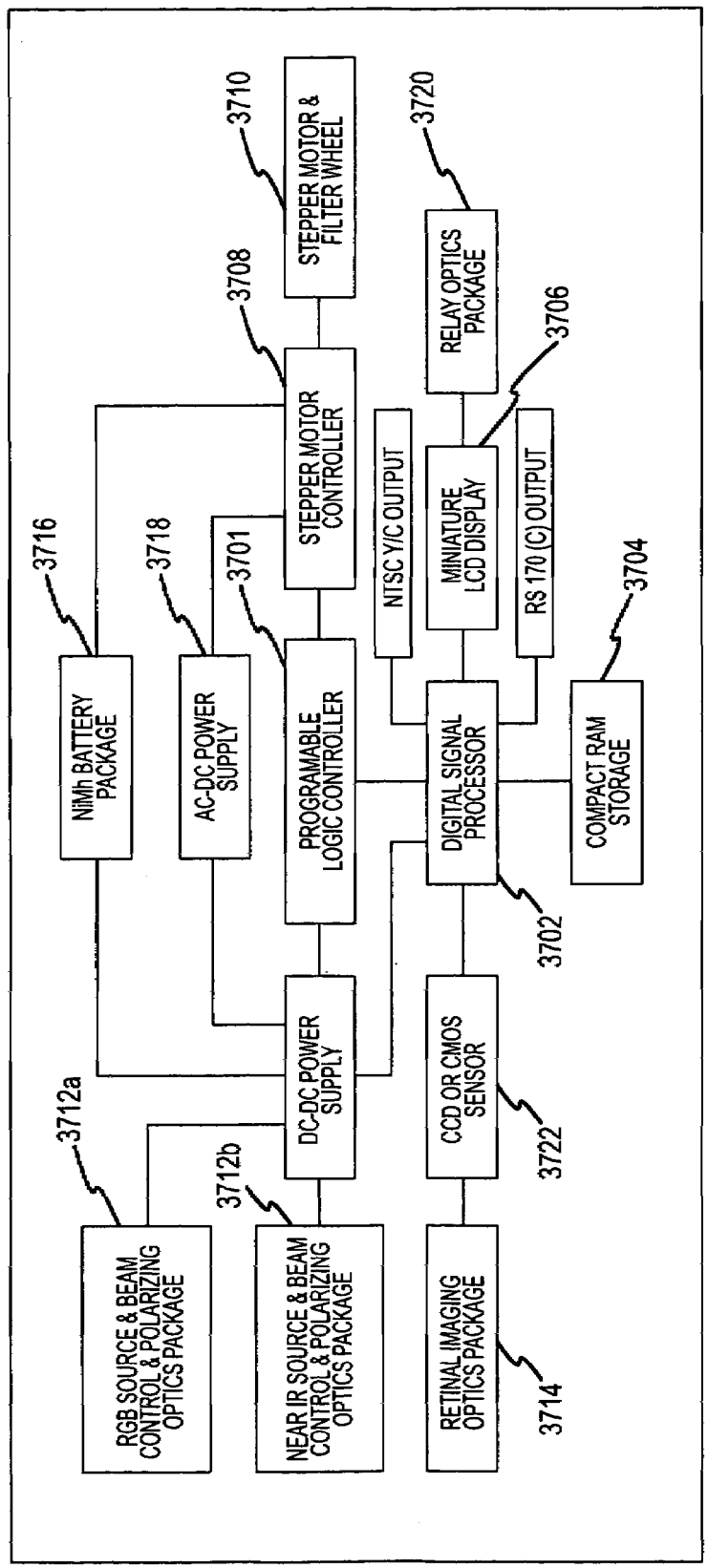
FIG. 37 illustrates a block diagram of an example of a hand held optical device, in accordance with one embodiment of the present invention.

FIG. 37 is a block diagram of one embodiment of a hand-held device including a programmable logic controller (PLC) or other processor or microcontroller (3701), a digital signal processor (DSP) (3702) if desired, memory (3704), a display (3706), a motor controlling a filter wheel (3710), a light source (3712a), (3712b), and optics for processing light from the light source. In one example, the device includes transmitting optics for selectively transmitting IR (3712b) and visible light (3712a) to the patient's retina; and receiving optics (3714) for receiving the IR and visible light reflected from the patient's retina. The device may be powered by a rechargeable battery (3716) or AC line voltage (3718) if desired.

The device may be implemented in a form factor or housing such that the device can be used by hand and in a portable manner. The transmitting optical components may include a light source (capable of emitting a full spectrum of light including IR light), beam control components including focusing optics, and a motor driving the position of a filter wheel having filtering elements therein. In one example, the filter wheel may have a plurality of filtering elements which selectively permit infrared light to pass therethrough; visible light to pass therethrough; fluorescein green light to pass therethrough for examining a diabetic's retina; and indocyanine green light to pass therethrough to permit examination of the deeper choroidal blood vessels.

The control components include a programmable logic controller (3701), and one or more pushbuttons (not shown) to permit the eye doctor to control the modes of operation of the device. The image processing components include a digital signal processor (DSP) (3702), an LCD display (3706), and a storage device (3704). The eye doctor may view the image of the patient's retina on LCD display (3702) through optics (3720).

In operation in one example, when examining a patient's retina, the device is activated so that the light source generates light which is focused through focusing optics and passed through a selected filtering elements of filter wheel (3710). For example, during infrared imaging of the retina, the filter wheel is positioned such that a particular filtering element is placed in the light path which permits only infrared light to pass therethrough.

A simplified filter arrangement can be substituted for parts. This would be an electromagnetic actuator (solenoid) with an infrared filter attached to an intermediate member that can be selectively inserted in the light path to provide a visible light or infrared pass band providing the practitioner a more basic instrument.

The received light signal is processed as a digital signal and manipulated and/or stored by the digital signal processor (3702). In one example, the infrared images captured are displayed by the display in real-time on device so that the eye doctor performing the retinal examination can view the images of the retina.

During the examination procedure, when the eye doctor wishes to obtain a color image of the retina using visible light, the motor rotates the filter wheel into a position which permits visible light to pass through the filter wheel, and this visible light is delivered to the patient's retina, preferably for no more than 10 milliseconds as described above. Simultaneously, the second filter wheel in the image path brings an optic into the path to compensate for the wavelength shift. During the time that the visible light is being used, the CCD/LCD sensor (3722) captures the retinal image and manipulates and/or stores the color image(s).

As described in other embodiments below, some other features include the use of the device to permit laser treatment of the retina. In one embodiment, an external laser may be connected to the device and the filter wheel may be provided with a reflecting mirror for one of its positions such that if desired, a laser beam from the external laser may be directed and delivered to the patient's retina to treat or cauterize bleeding blood vessels of the retina. Furthermore, the device could be adapted with a USB or other data link, or a digital memory card, in order to permit data (real-time or otherwise) to be transmitted to a computer system to store patient retinal profiles obtained from the eye exam.

Various other embodiments of a hand held device, and related methods, in accordance with the present invention will now be described.

FIG. 8 shows a means to illuminate the retina through a small diameter pupil without the use of a pupil-dilating mydriatic solution. A light source producing visible non-polarized light is refracted by a beam-forming optic, producing a parallel non-polarized beam; said beam is then linearly S polarized and subsequently right-hand circularly polarized and refracted by a second optic to produce a converging beam. The converging beam is designed to create a focal point located in such a manner as to fully illuminate the retina through a small pupil diameter. The illumination of the retina by means of a small pupil precludes the need for a mydriatic pupil dilating solution.

In FIG. 10, a method may be implemented to transmit depolarized reflected rays of the retinal image in a diverging beam to the eye of an observer or CCD or CMOS imaging circuit. Said randomly polarized beam is refracted by the objective optic, becoming randomly polarized retinal image rays parallel to the optical axis. Said rays pass through the quarter wave retarder and are minimally affected, and are polarized by the broad band linear polarizer. The rays exit the polarizer as horizontal linearly polarized rays. The rays then enter the wire grid polarizing beam splitter, (or a broad-band polarizing beam splitter cube), with its axis aligned with the transmission axis of the linear polarizer. (Alternatively, a non-polarizing beam splitter cube could be substituted for the polarizing beam splitter cube). The polarized rays of the retinal image are then refracted by the image-forming optics to create a real image of the retina at the eye of the observer or the face of a CCD or CMOS or other imager.

FIGS. 8, 9 show an example of a method of extinguishing corneal specular reflection based on circular polarization. The method utilizes the illumination and polarization methodology described above with regard to FIG. 8, together with a circularization polarization components to eliminate the corneal specular reflection, as follows: The use of a broad-band linear polarizer in conjunction with an achromatic quarter wave plate retarder oriented at −45 degrees relative to the circularly polarized reflected beam serves to eliminate corneal specular reflection by rotating the reflected rays 90 degrees from the input polarization plane.

In FIG. 10, an alternate method may be implemented for illuminating the retina utilizing doubly polarized light. The method utilizes a broad-band polarizing beam splitter in conjunction with a broad-band linear polarizer, for which the transmission axes of both polarizers are aligned, in combination with a broadband quarter wave retarder with its S axis oriented at 45 degrees relative to the aligned planes of polarization for both polarizers.

In FIG. 14, another method may be implemented for illuminating the retina utilizing doubly polarized light. The method utilizes a broad-band polarizing beam splitter in conjunction with 2 broad-band linear polarizers, for which the transmission axes of both polarizers are aligned, in combination with 2 broadband quarter wave retarder with their S axes oriented at 45 degrees relative to the aligned planes of polarization for both polarizers.

In FIG. 12, an alternate method may be implemented for extinguishing specular corneal reflections by using circularly polarized light. The method makes the focal point of the converging circularly polarized illuminating rays coincident with the point of specular reflection on the cornea. As a result, the return diverging circularly polarized rays are a mirror-image of the initial converging illuminated rays. This allows the optic (7 in FIG. 11) to refract the diverging beam into parallel light which then reaches the quarter wave plate retarder as parallel light, which is necessary for optimum performance of the quarter wave retarder and the beam splitter.

In FIG. 12, a method may be implemented to improve the method for extinguishing specular corneal reflections by using circularly polarized light, as described with reference to FIGS. 8, 9. The method makes the focal point of the converging circularly polarized illuminating rays coincident with the focal point of specular reflection on the cornea. As a result, the return diverging circularly polarized rays are a mirror-image of the initial converging illuminated rays. This allows the optic, (18) in FIG. 12, to refract the diverging beam into parallel light which then reaches the quarter wave plate retarder as parallel light, which is necessary for optimum performance of the quarter wave retarder and the beam splitter.

In FIG. 14, a method may be implemented to eliminate stray light that might otherwise interfere with the optical path or the image on the image capture device. The method utilizes two circular knife edge baffles: One captures the transmitted rays through the broadband non-polarizing beam splitter following the beam forming optic for the light source. The other captures the transmitted rays from the broadband polarizing beam splitter in the optical return path.

In FIG. 13, a method may be implemented for minimizing wavefront aberration of the retinal image. By refracting the diverging beam containing the image of the retina (which is depolarized after its reflection from the retina) into a parallel beam prior to its arrival at the polarizing beam splitter cube, the passage through the beam splitter will create a P plane polarized image with minimum wavefront distortion and geometric aberration. The image of the retina is refracted by optics (10) to create a real image at (11), which may be the observer's eye or a CCD or CMOS chip or any imaging device.

Further, embodiments can be made incorporating the method of extinguishing corneal specular reflectance and/or using doubly polarized light described above, and the method for minimizing wavefront aberration of the retinal image described above, or any combination of them.

In FIG. 14, a method may be implemented for creating a point of focus in space from a halogen, incandescent or discharge lamp source, free from stray light rays. A light source is chosen whose polar distribution is most advantageous for the collection angle of the ellipsoidal optic. The rays emanating from the light source are specularly reflected by an ellipsoidal reflector and arrive at the second focal point. The ellipsoidal reflector has the property of containing two focal points whereby rays at the first focal point will be brought to a point focus at the second focal point. By placing a light shield to interrupt the stray light rays emitted by the lamp, a greater uniformity of ray focus can be achieved at the second focal point.

Further in FIG. 14, a method may be implemented for controlling beam intensity utilizing a variable circular aperture critically placed relative to the second focal point. In order not to change the color temperature or block body radiation characteristics of the light source, a variable circular aperture is used instead to control beam intensity. This is most efficiently accomplished by placing said aperture exactly at the second focal point of the elliptical optic.

In FIG. 16, a method may be implemented for correcting both depolarizations and optical aberrations in the light beam prior to the beam's reaching the image capture device. The method includes using a polarizing element which is a custom fractional wave plate retarder designed to compensate for aberrations and/or depolarization resulting from the birefringence of the optics through which the rays have passed prior to reaching this custom element.

In FIG. 17, a method may be implemented for automatically synchronizing the beam intensity required by moving the beam forming optic with the beam intensity generated from the light source, as an a alternative, to manually adjusting the beam intensity required by moving the beam forming optic with the beam intensity generated from the light source. Movement of the beam forming optic in order to fill the pupil with light, as elaborated below with regard to FIG. 23), requires increasing or decreasing the intensity of light that is refracted through the objective optic. In order to provide that variability automatically, movement of the beam forming optic automatically generates a control signal which is appropriate to vary the circular aperture placed at the second focal point.

In FIG. 11, a method may be implemented for providing rapidly changeable multi-spectral filters in the illumination path. It is desirable to use various light frequencies for examining the retina. For example, infrared light has the advantages of being invisible (and therefore not irritating to the patient), not changing the pupillary response, passing through blood and other opacities better than visible light, and preferentially highlighting the choroid and deeper layers of the eye. Green light preferentially highlights the anterior layers of the retina. Other light frequencies have the ability to excite dyes such as fluorescein or indocyanine green which may have been injected into the retinal and/or choroidal circulation.

Therefore, by placing a filter wheel adjacent to the second focal point, where the diverging beam diameter remains small, a miniature filter will intercept the entire cone angle of the beam. By virtue of using a small diameter filter, the diameter of the filter wheel can be minimized, thereby greatly reducing the polar moment of inertia, therefore allowing rapid rotational motion while maintaining precise placement of the individual filters within the beam path. Very rapid and accurate transition from one filter to another is therefore possible, allowing multiple modes of examination nearly simultaneously. Two simultaneously injected dyes could be excited in rapid succession allowing both to be subsequently and recorded nearly simultaneously.

Also, it would be possible to switch between infra-red and visible light so rapidly that the pupil does not have time to respond, allowing a visible light image to be captured with the least amount of perception of the visible light illumination.

In FIG. 11, methods may be implemented for rapid rotation of the filter wheels discussed above with regard to FIG. 11, while maintaining precision placement of the filters within the light path. A. A stepper motor is used in open loop or closed loop control mode to mechanically rotate the filter wheel by gear or belt. B. The filter wheel would be incorporated into a spur gear that would driven by the stepper motor. C. The filter wheel would be incorporated into the armature of a motor and driven by the stator coils of the motor which would be selectively energized to precisely place the filters of the wheel in the beam path for the appropriate intervals.

In FIG. 12, a method may be implemented for removal of the filament image and presenting a very uniform illuminated beam to the subsequent optics. In order to remove the filament image and present a very uniform illuminated beam to the subsequent optics, a diffuser is placed in the parallel ray path section immediately subsequent to the illuminating beam forming optic. The diffuser is placed in the parallel ray path so that the angle of incidence is minimized, thereby optimizing the output beam divergence (minimizing the exit angle) through the diffuser.

In FIG. 12, a method may be implemented for removal of the filament image and presenting a very uniform illuminated beam to the subsequent optics, as described above with reference to FIG. 12. However, a holographic diffuser is substituted for an ordinary diffuser. The beam transmission efficiency is thereby increased and the exit angle is better controlled.

In FIG. 20, a method may be implemented to introduce a fixation spot to be viewed by the patient. By placing an optically bonded prism directly onto the beam splitter, it provides an optical port through which a fixation laser beam can be introduced into the center of the main illuminating beam without introducing significant aberrancy of the fixation beam. The use of a laser beam shaping optic in conjunction with the objective lens provides for a tightly collimated beam for the fixation point. By selectively applying thin film coatings with specific reflective and transmissive characteristics, the reflected illumination rays are selectively reflected over an angle of 90 degrees with minimal loss, and the intensity of the laser beam is reduced by the selective reduction of transmission through the beam splitter, based on the coating chosen.

In another embodiment, a method may be implemented for varying the fixation spot so that it is seen by both the patient and the observer (or image capture device), by neither the patient nor the observer (or image capture device), or only by the patient, so as to not interfere with the image seen by the observer (or image capture device). A) The fixation spot is seen by both the patient and the observer (or image capture device). The method described in FIG. 20 may be employed. A narrow band pass filter may be also substituted or used in conjunction with the neutral density filter present in the fixation beam path. B) The fixation spot is seen by neither the patient nor the observer (or image capture device). The method described in FIG. 20 may be employed, and the laser is turned off. A narrow band pass filter may be also substituted or used in conjunction with the neutral density filter present in the fixation beam path. C) The fixation spot is seen by the patient but not by the observer (or image capture device). The method described in FIG. 20 may be employed. A narrow band pass filter may be also substituted or used in conjunction with the neutral density filter present in the fixation beam path. A filter is introduced in the return path that will attenuate the frequency chosen by the narrow band pass filter. By virtue of using narrow band pass filters, the possibility for losing image data by filtering out the central fixation spot is minimized. D) The fixation spot is seen by the patient but not by the image capture device—alternative method. The method described in FIG. 20 may be employed. Electronic synchronization of the laser beam and image capture device is such that the laser is turned off for an interval, e.g., a ⅟₆₀th of a second, during which time the image capture device records the retinal image without the image of the fixation beam. Because of the persistence of retinal imagery for at least 40 milliseconds, the patient would be unaware of the interval during which the fixation laser was turned off and would appreciate the fixation image as a steady image.

In FIG. 21, an alternate method may be implemented to introduce a fixation spot to be viewed by the patient. By placing an optically bonded 45 degree glass surface directly onto the hypotenuse of a prism, it provides an optical port through which a fixation laser beam can be introduced into the center of the main illuminating beam without introducing significant aberrancy of the fixation beam. The use of a laser beam shaping optic in conjunction with the objective lens provides for a tightly collimated beam for the fixation point. By selectively applying thin film coatings to the optically bonded 45 degree glass surface with specific reflective and transmissive characteristics, the reflected illumination rays are selectively reflected over an angle of 90 degrees with minimal loss, and the intensity of the laser beam is reduced by the selective reduction of transmission through the optically bonded 45 degree glass surface, based on the coating chosen.

In FIG. 22, an alternate method may be implemented to introduce a fixation spot to be viewed by the patient. By placing a 90 degree mirror fixed directly onto the filament shield, it provides an optical port through which a fixation laser beam can be introduced into the center of the main illuminating beam without introducing significant aberrancy of the fixation beam. By placing the mirror prior to the second focal point of the illuminating beam, it can occupy a space that will not shadow the beam. The use of a laser beam shaping optic in conjunction with the objective lens provides for a tightly collimated beam for the fixation point. By selectively applying thin film coatings to the optically bonded 45 degree glass surface with specific reflective and transmissive characteristics, the reflected illumination rays are selectively reflected over an angle of 90 degrees with minimal loss, and the intensity of the laser beam is reduced by the selective reduction of transmission through the optically bonded 45 degree glass surface, based on the coating chosen.

In another embodiment, a method for providing rapidly changeable multi-spectral filters in the image path is disclosed. It is desirable to be able to have various selected light frequencies fall on the retina of the observer or on the image capture device. For example, to selectively attenuate the fixation image, as discussed above. Another example: if the illumination beam is visible light, it would be desirable to interpose a IR cut filter before the image capture device. Other select filters may be chosen for specific applications.

By placing a filter wheel in front of the image capture device where the image beam is already converging towards its minimum diameter, a small filter will intercept the entire cone angle of the beam. By virtue of using a small diameter filter, the diameter of the filter wheel can be minimized, thereby greatly reducing the polar moment of inertia, therefore allowing rapid rotational motion while maintaining precise placement of the individual filters within the beam path. Very rapid and accurate transition from one filter to another is therefore possible, allowing multiple modes of examination nearly simultaneously.

In another embodiment of the invention, a method for providing rapidly interchangeable optics in the illumination and/or the image path is disclosed. The filter wheels discussed above can also carry optical elements either in the recesses specified for filters, or bonded to the filters. Utilizing the electromechanical arrangements discussed above with reference to FIG. 11, the very rapid and accurate transition from one optic to another is therefore possible, allowing multiple modes of examination nearly simultaneously.

In FIG. 31-32, an alternative simplified method may be implemented for providing rapidly interchangeable optics and/or filters in the illumination and/or the image path. A linear electromagnetic actuator is employed to rapidly and accurately move the optics and or filters in and out of the optical pathways.

In another embodiment, a method to maximize the efficiency of illumination of the retina through various pupillary diameters is disclosed. Movement of the beam forming optic can fill the pupil with light. Movement of the beam forming optic results in manipulation of the conjugate ratio of the second focal point of the ellipsoidal reflector, resulting in variation of the cone angle of the converging illumination beam as it enters the eye.

Such manipulation of the conjugate ratio is made possible through the selection of materials for the polarizer(s) and quarter wave retarder(s) which have a large enough acceptance angle to allow for such ray manipulation while still performing their intended functions efficiently. The means for synchronizing the beam intensity required by moving the beam forming with the beam intensity generated from the light source has already been discussed above with reference to FIG. 17.

As shown in FIGS. 27-32, a method for focusing the retinal image on the observer's retina or image capturing device may be implemented.

Focusing the retinal image may be accomplished by either: A) moving an optic in front of the observer's retina or image capturing device, or B) moving the observer's retina relative to the instrument, or moving the image capture device. The movement in method A is accomplished by means of a controlled motor operating either a gear or belt system, or by a manual gear or belt system. In another embodiment, a method for automatically focusing the retinal image on the observer's retina or image capturing device is disclosed. Either method A or B as described above can be utilized. The motor control signal necessary to achieve optimum focus on the image capture device is generated by capturing and processing a portion of the image rays, or by capturing and processing a portion of the signal generated by the image capturing device.

In another embodiment, a method to vary the light intensity so as to maximize the efficiency of the image capture device is disclosed. The image capture device will generate a control signal, based on the intensity of the image, which will adjust the aperture with a feedback loop to bring the image intensity falling on the capture device into the optimal operating range for the latter.

In another embodiment, a method may be implemented to pre-set functions on the hand held device, enter data to go with captured images, recharge the batteries of the hand-held device, and furnish an additional image screen for viewing by others. Two or more of the above functions are incorporated into the docking device on which the hand-held device sits when not in use. A keyboard, recharging circuitry, and an additional screen are inherent parts of that device. The device may also contain radio frequency data link (or hard wired in another embodiment) circuitry to provide data transfer and real time images which could be shown on the screen of the device (or an auxiliary computer or monitor) in addition to those seen directly by the operator. Similarly, the data could be manipulated by the docking device and/or an auxiliary computer, e.g., for making composite multiple images into a single panoramic image, and/or for storage and/or retransmission. Such panoramic (or otherwise processed) images could even be retransmitted to the viewing screen in the hand held device, e.g., to alert the operator for the need and location of additional images to taken. Of course, all data from the docking device could be sent by radio frequency data link (or hard wired in another embodiment) to the hand held device.

In FIG. 17, a method may be implemented for fixation of the eye contralateral to that being viewed utilizing an array of point light sources. An array consisting of point light sources such as LED's, optical fibers, or similar point light sources can fold out from each side of the instrument (or a single array may be rotated to the desired position). Individual points can be illuminated manually or by an automated sequence in order to bring the portion of the eye being viewed into the desired position for viewing.

In another embodiment, a method for recording panoramic/composite images in a standardized fashion is disclosed. Utilizing the automated sequence of fixation points described above with reference to FIG. 17, multiple images of the retina are recorded and software is used to combine those images into a single large image.

In another embodiment, a method is disclosed for achieving fixation when the eye contralateral to that being viewed has a central scotoma which prevents central fixation. Utilizing the array described with regard to FIG. 17, points are illuminated outside the central scotoma. The patient is asked to view those points and to fixate at the center of those points, even if he cannot see that central spot.

If desired, one or more of the components shown and described herein may be obtained commercially as follows, depending upon the particular implementation of an embodiment of the present invention. It is understood that this list is provided by way of example only, and does not limit the scope of the invention. Lenses may be obtained from Melles Griot, Irvine, Calif.; Spectra-Physics/Oriel Instruments, Stratford, Conn. 90 degree prisms (large & small) may be obtained from Melles Griot, (large) Part #:01 PRT 029, (ssmall) Part #:01 PRT 003. A miniature 90 degree rod mirror may be supplied by Edmund Industrial Optics, Barrington, N.J., such as Part #:H54-095. Broadband non-polarizing beam splitter cube may be supplied by Rolyn Optics Company Covina, Calif., such as Part#47.0350. Custom Broadband polarizing beam splitter may be supplied by Moxtek Inc., Orem, Utah. An achromatic linear polarizer may be supplied by Meadowlark Optics, Fredrick, Colo. Achromatic quarter wave & custom fractional wave plate retarders may be supplied by Meadowlark Optics, Fredrick, Colo. Near infrared band pass filter may be supplied by Schott North America, Elmsford, N.Y., such as Part# Glass type RG9. Holographic Diffuser may be supplied by Edmund industrial optics, such as Part # H55-848. Miniature stepper motors may be supplied by MicroMo Electronics Inc., Clearwater, Fla., such as Series part number AM 0820. Halogen light source (miniature lamp) may be supplied by Chicago Miniature Lamp Inc., Hackensack, N.J., such as Part # CM2059. Miniature linear ball bearing slide may be supplied by Del-Tron Precision Inc., Bethel, Conn., such as Part # S1-1. Variable Apertures (also called iris diaphragm) may be supplied by Melles Griot, such as Part #04 IDC 005. A CCD imager (board level CCD video camera) may be supplied by Cohu Inc., Electronics Division, San Diego, Calif., such as Part #1100 Series.

It should be appreciated that reference throughout this specification to "one embodiment" or "an embodiment" or "one example" or "an example" means that a particular feature, structure or characteristic described in connection with the embodiment may be included, if desired, in at least one embodiment of the present invention. Therefore, it should be appreciated that two or more references to "an embodiment" or "one embodiment" or "an alternative embodiment" or "one example" or "an example" in various portions of this specification are not necessarily all referring to the same embodiment. Furthermore, the particular features, structures or characteristics may be combined as desired in one or more embodiments of the invention.

Similarly, it should be appreciated that in the foregoing description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed inventions require more features than are expressly recited in each claim. Rather, as the following claims reflect, inventive aspects lie in less than all features of a single foregoing disclosed embodiment, and each embodiment described herein may contain more than one inventive feature.

While the methods disclosed herein have been described and/or shown with reference to particular operations performed in a particular order, it will be understood that these operations may be combined, sub-divided, or re-ordered to form a equivalent methods without departing from the teachings of the present invention. Accordingly, unless specifically indicated herein, the order and grouping of the operations is not a limitation of the present invention.

While the invention has been particularly shown and described with reference to various embodiments thereof, it will be understood by those skilled in the art that various other changes in the form and details may be made without departing from the spirit and scope of the invention.

The invention claimed is:

1. A hand held device for examining a retina through a pupil, comprising:
   a light source generating light;
   a first lens refracting the light to form a refracted beam;
   a first polarizer receiving the refracted beam and forming a linear polarized beam;
   a second polarizer for reflecting linearly polarized light, the second polarizer receiving the linear polarized beam and reflecting the linear polarized beam;
   a second lens refracting the linear polarized beam from the second polarizer, the second lens converging the linear polarized beam for passage through the pupil to illuminate the retina; and
   a beam splitter positioned between the first lens and the first polarizer, the beam splitter receiving the refracted beam, the beam splitter reflecting the refracted beam to the first polarizer.

2. The hand held device of claim 1, wherein the light generated by the light source includes infrared (IR) light.

3. The hand held device of claim 1, wherein the light source includes a first lamp in series with an infrared (IR) filter to generate the light.

4. The hand held device of claim 1, wherein the light generated by the light source includes visible light.

5. The hand held device of claim 1, further comprising:
   a reflector reflecting the light to form a reflected converging beam for coupling into the first lens.

6. The hand held device of claim 1, further comprising:
   a variable diaphragm located between the light source and the first lens for controlling the intensity of the light.

7. The hand held device of claim 1, wherein the first polarizer is a wire grid polarizer.

8. The hand held device of claim 1, wherein the second polarizer is a wire grid polarizer, the second polarizer is substantially disposed at an angle of 45 degrees relative to linear polarized beam.

9. The hand held device of claim 1, wherein the pupil is undilated during examination of the retina.

10. A hand held device for examining a retina through a pupil, comprising:
    a light source generating light;
    a reflector reflecting the light to form a reflected converging beam;
    a polarizer receiving the reflected converging beam and forming a linear polarized converging beam;
    a second polarizer for reflecting linearly polarized light, the second polarizer receiving the linear polarized converging beam and reflecting the linear polarized converging beam through the pupil to illuminate the retina and thereby creating a reflected image of the retina, a portion of said reflected image passing through the second polarizer,
    a first lamp in series with an infrared (IR) bandpass filter to generate IR light; and
    a second lamp in series with a visible light bandpass filter to generate visible light, wherein when the first lamp is on, the second lamp is off.

11. The hand held device of claim 10, further comprising:
    a lens refracting said portion of the reflected image of the retina to create a real image of the retina.

12. The hand held device of claim 10, further comprising:
    a detector receiving the real image of the retina.

13. The hand held device of claim 12, wherein the detector is a charged coupled device (CCD) detector.

14. A hand held device for examining a retina through a pupil, comprising:
    a light source generating light;
    a reflector reflecting the light to form a reflected beam;
    a polarizer receiving the reflected beam and forming a linear polarized beam;
    a second polarizer for reflecting linearly polarized light, the second polarizer receiving the linear polarized beam and reflecting the linear polarized beam through the pupil to illuminate the retina and thereby creating a reflected image of the retina, a portion of said reflected image passing through the second polarizer,
    a first lamp in series with an infrared (IR) bandpass filter to generate IR light; and
    a second lamp in series with a visible light bandpass filter to generate visible light, wherein when the first lamp is on, the second lamp is off.

15. The hand held device of claim 14, further comprising:
    a lens refracting said portion of the reflected image of the retina to create a real image of the retina.

16. The hand held device of claim 14, further comprising:
    a detector receiving the real image of the retina.

17. The hand held device of claim 10, wherein the detector is a charged coupled device (CCD) detector.

* * * * *